(12) United States Patent
Dumont et al.

(10) Patent No.: US 7,220,747 B2
(45) Date of Patent: May 22, 2007

(54) METHOD FOR PREVENTING DAMAGE TO OR REJUVENATING A CELLULAR BLOOD COMPONENT USING MITOCHONDRIAL ENHANCER

(75) Inventors: Larry Joe Dumont, Arvada, CO (US); Raymond P. Goodrich, Jr., Lakewood, CO (US)

(73) Assignee: Gambro, Inc., Lakewood, CO (US)

( * ) Notice: Subject to any disclaimer, the term of this patent is extended or adjusted under 35 U.S.C. 154(b) by 298 days.

(21) Appl. No.: 10/430,896

(22) Filed: May 6, 2003

(65) Prior Publication Data

US 2003/0216285 A1 Nov. 20, 2003

Related U.S. Application Data

(63) Continuation-in-part of application No. 09/586,147, filed on Jun. 2, 2000, now abandoned, which is a continuation-in-part of application No. 09/357,188, filed on Jul. 20, 1999, now Pat. No. 6,277,337, which is a continuation-in-part of application No. 09/119,666, filed on Jul. 21, 1998, now Pat. No. 6,258,577, application No. 10/430,896, which is a continuation-in-part of application No. 09/777,727, filed on Feb. 5, 2001, now Pat. No. 6,828,323, which is a continuation of application No. 09/420,652, filed on Oct. 19, 1999, now Pat. No. 6,268,120.

(60) Provisional application No. 60/378,374, filed on May 6, 2002.

(51) Int. Cl.
*A01N 43/60* (2006.01)
*C07D 239/00* (2006.01)

(52) U.S. Cl. .......................... 514/251; 544/251; 435/2

(58) Field of Classification Search ............ 435/173.3, 435/2; 514/457
See application file for complete search history.

(56) References Cited

U.S. PATENT DOCUMENTS

| | | | |
|---|---|---|---|
| 683,690 A | 10/1901 | Johnson | |
| 1,733,239 A | 10/1929 | Roberts | |
| 1,961,700 A | 6/1934 | Moehler | 167/3 |
| 2,056,614 A | 10/1936 | Moehler | 21/18 |
| 2,111,491 A | 3/1938 | Kuhn et al. | 260/29 |
| 2,212,230 A | 8/1940 | Goldman | 250/11 |
| 2,212,330 A | 8/1940 | Thomas | 250/52 |
| 2,340,890 A | 2/1944 | Lang et al. | |
| 2,654,753 A | 10/1953 | Funk et al. | 260/211.3 |
| 2,786,014 A | 3/1957 | Tullis | |
| 2,825,729 A | 3/1958 | Petering et al. | 260/251.5 |
| 3,189,598 A | 7/1965 | Yagi et al. | 260/211.3 |
| 3,456,053 A | 7/1969 | Crawford | 424/89 |
| 3,629,071 A | 12/1971 | Sekhar | 195/1.8 |
| 3,683,177 A | 8/1972 | Veloz | 250/43 |
| 3,683,183 A | 8/1972 | Vizzini et al. | 250/44 |
| 3,705,985 A | 12/1972 | Manning et al. | 250/106 S |
| 3,776,694 A | 12/1973 | Leird | 21/102 R |
| 3,852,032 A | 12/1974 | Urbach | 21/54 |
| 3,864,081 A | 2/1975 | Logrippo | 21/102 R |
| 3,874,384 A | 4/1975 | Deindoerfer et al. | 128/272 |
| 3,894,236 A | 7/1975 | Hazelrigg | 250/435 |
| 3,920,650 A | 11/1975 | Spencer et al. | 260/251.5 |
| 3,926,556 A | 12/1975 | Boucher | 21/54 R |
| 3,927,325 A | 12/1975 | Hungate et al. | 250/435 |
| 4,061,537 A | 12/1977 | Seiler et al. | |
| 4,112,070 A | 9/1978 | Harmening | |
| 4,124,598 A | 11/1978 | Hearst et al. | 260/343.21 |
| 4,139,348 A | 2/1979 | Swartz | 23/232 E |
| 4,169,204 A | 9/1979 | Hearst et al. | 546/270 |
| 4,173,631 A | 11/1979 | Graham et al. | 424/180 |
| 4,181,128 A | 1/1980 | Swartz | 128/207.21 |
| 4,196,281 A | 4/1980 | Hearst et al. | 536/28 |
| 4,267,269 A | 5/1981 | Grode et al. | 435/2 |
| 4,312,883 A | 1/1982 | Baccichetti et al. | 424/279 |
| 4,321,918 A | 3/1982 | Clark, II | 128/124 R |
| 4,321,919 A | 3/1982 | Edelson | 128/124 R |

(Continued)

FOREIGN PATENT DOCUMENTS

EP     0 066 886     6/1982

(Continued)

OTHER PUBLICATIONS

Kampa et al., BioMed C. Clinical pathology, 2002(2) pp. 1-16.*

(Continued)

*Primary Examiner*—Ardin H. Marschel
*Assistant Examiner*—Shirley V. Gembeh
(74) *Attorney, Agent, or Firm*—Greenlee Winner and Sullivan PC

(57) ABSTRACT

This invention provides methods for treating cellular blood components and other cells containing mitochondria to improve vital qualities of the cells by contacting the cells with a mitochondrial enhancer to the cells. Mitochondrial enhancers prevent damage to and rejuvenate mitochondria and cells containing mitochondria. Mitochondrial enhancers include alloxazines and related compounds, such as riboflavin. Cells are optionally treated with photoradiation to reduce pathogens with may be present, before, after, and/or during treatment with mitochondrial enhancer. Treating with mitochondrial enhancer enables utilization of higher photoradiation energies, which achieves better pathogen reduction. When platelets are treated with mitochondrial enhancer, treated platelets may be stored for longer times than untreated platelets before they are administered to patients.

39 Claims, 14 Drawing Sheets

U.S. PATENT DOCUMENTS

| | | | |
|---|---|---|---|
| 4,336,809 A | 6/1982 | Clark | 128/665 |
| 4,386,069 A | 5/1983 | Estep | 424/101 |
| 4,390,619 A | 6/1983 | Harmening-Pittiglio | 435/2 |
| 4,398,031 A | 8/1983 | Bender et al. | 549/282 |
| 4,398,906 A | 8/1983 | Edelson | 604/6 |
| 4,402,318 A | 9/1983 | Edelson | 604/6 |
| 4,407,282 A | 10/1983 | Swartz | 604/20 |
| 4,421,987 A | 12/1983 | Herold | 250/492.1 |
| 4,424,201 A | 1/1984 | Valinsky et al. | 424/3 |
| 4,428,744 A | 1/1984 | Edelson | 604/6 |
| 4,432,750 A | 2/1984 | Estep | 604/4 |
| 4,456,512 A | 6/1984 | Bieler et al. | 204/162 R |
| 4,464,166 A | 8/1984 | Edelson | 604/6 |
| 4,467,206 A | 8/1984 | Taylor et al. | 250/435 |
| 4,481,167 A | 11/1984 | Ginter et al. | 422/29 |
| 4,493,981 A | 1/1985 | Payne | 219/450 |
| 4,568,328 A | 2/1986 | King | 604/6 |
| 4,572,899 A | 2/1986 | Walker et al. | 436/18 |
| 4,573,960 A | 3/1986 | Goss | 604/6 |
| 4,573,961 A | 3/1986 | King | 604/6 |
| 4,573,962 A | 3/1986 | Troutner | 604/6 |
| 4,576,143 A | 3/1986 | Clark, III | 128/1 R |
| 4,578,056 A | 3/1986 | King et al. | 604/6 |
| 4,585,735 A | 4/1986 | Meryman et al. | 435/2 |
| 4,596,547 A | 6/1986 | Troutner | 604/4 |
| 4,604,356 A | 8/1986 | Blake, II | 435/194 |
| 4,608,255 A | 8/1986 | Kahn et al. | 424/101 |
| 4,609,372 A | 9/1986 | Carmen et al. | 604/262 |
| 4,612,007 A | 9/1986 | Edelson | 604/5 |
| 4,613,322 A | 9/1986 | Edelson | 604/6 |
| 4,614,190 A | 9/1986 | Stanco et al. | 128/395 |
| 4,623,328 A | 11/1986 | Hartranft | 604/4 |
| 4,626,431 A | 12/1986 | Batchelor et al. | 424/101 |
| 4,642,171 A | 2/1987 | Sekine et al. | 204/298 |
| 4,645,649 A | 2/1987 | Nagao | 422/186.3 |
| 4,648,992 A | 3/1987 | Graf et al. | 540/124 |
| 4,649,151 A | 3/1987 | Dougherty et al. | 514/410 |
| 4,651,739 A | 3/1987 | Oseroff et al. | 128/395 |
| 4,675,185 A | 6/1987 | Kandler et al. | 424/101 |
| 4,683,195 A | 7/1987 | Mullis et al. | 435/6 |
| 4,683,202 A | 7/1987 | Mullis | 435/91 |
| 4,683,889 A | 8/1987 | Edelson | 128/395 |
| 4,684,521 A | 8/1987 | Edelson | 424/101 |
| 4,693,981 A | 9/1987 | Wiesehahn et al. | 435/238 |
| 4,695,460 A | 9/1987 | Holme | 424/101 |
| 4,704,352 A | 11/1987 | Miripol et al. | 435/2 |
| 4,708,715 A | 11/1987 | Troutner et al. | 604/6 |
| 4,726,949 A | 2/1988 | Miripol et al. | 424/101 |
| 4,727,027 A | 2/1988 | Wiesehahn et al. | 435/173 |
| 4,737,140 A | 4/1988 | Lee et al. | 604/4 |
| 4,748,120 A | 5/1988 | Wiesehahn | 435/173 |
| 4,769,318 A | 9/1988 | Hamasaki et al. | 435/2 |
| 4,775,625 A | 10/1988 | Sieber | 435/238 |
| 4,788,038 A | 11/1988 | Matsunaga | 422/22 |
| RE32,874 E | 2/1989 | Rock et al. | 424/101 |
| 4,828,976 A | 5/1989 | Murphy | 435/2 |
| 4,831,268 A | 5/1989 | Fisch et al. | 250/432 R |
| 4,833,165 A | 5/1989 | Louderback | 514/694 |
| 4,861,704 A | 8/1989 | Reemtsma et al. | 435/1 |
| 4,866,282 A | 9/1989 | Miripol et al. | 250/455.1 |
| 4,878,891 A | 11/1989 | Judy et al. | 604/5 |
| 4,880,788 A | 11/1989 | Moake et al. | 514/150 |
| 4,915,683 A | 4/1990 | Sieber | 604/4 |
| 4,921,473 A | 5/1990 | Lee et al. | 494/27 |
| 4,925,665 A | 5/1990 | Murphy | 424/532 |
| 4,930,516 A | 6/1990 | Alfano et al. | 128/665 |
| 4,946,438 A | 8/1990 | Reemtsma et al. | 604/53 |
| 4,948,980 A | 8/1990 | Wedekamp | 250/504 R |
| 4,950,665 A | 8/1990 | Floyd | 514/222.8 |
| 4,952,812 A | 8/1990 | Miripol et al. | 250/455.1 |
| 4,960,408 A | 10/1990 | Klainer et al. | 604/4 |
| 4,961,928 A | 10/1990 | Holme et al. | 424/533 |
| 4,978,688 A | 12/1990 | Louderback | 514/722 |
| 4,986,628 A | 1/1991 | Lozhenko et al. | 350/96.29 |
| 4,992,363 A | 2/1991 | Murphy | 435/2 |
| 4,994,367 A | 2/1991 | Bode et al. | 435/2 |
| 4,998,931 A | 3/1991 | Slichter et al. | 604/20 |
| 4,999,375 A | 3/1991 | Bachynsky et al. | 514/455 |
| 5,011,695 A | 4/1991 | Dichtelmuller et al. | 424/529 |
| 5,017,338 A | 5/1991 | Surgenor | 422/41 |
| 5,020,995 A | 6/1991 | Levy | 433/215 |
| 5,030,200 A | 7/1991 | Judy et al. | 604/5 |
| 5,039,483 A | 8/1991 | Sieber et al. | 422/28 |
| 5,041,078 A | 8/1991 | Matthews et al. | 604/4 |
| 5,089,146 A | 2/1992 | Carmen et al. | 210/782 |
| 5,089,384 A | 2/1992 | Hale | 435/2 |
| 5,092,773 A | 3/1992 | Levy | 433/224 |
| 5,095,115 A | 3/1992 | Grimmer et al. | 544/244 |
| 5,114,670 A | 5/1992 | Duffey | 422/24 |
| 5,114,957 A | 5/1992 | Hendler et al. | 514/356 |
| 5,120,649 A | 6/1992 | Horowitz et al. | 435/173 |
| 5,123,902 A | 6/1992 | Müller et al. | 604/21 |
| 5,133,932 A | 7/1992 | Gunn et al. | 422/24 |
| 5,147,776 A | 9/1992 | Koerner, Jr. | 435/2 |
| 5,149,718 A | 9/1992 | Meruelo et al. | 514/732 |
| 5,150,705 A | 9/1992 | Stinson | 128/396 |
| 5,166,528 A | 11/1992 | Le Vay | 250/455.11 |
| 5,184,020 A | 2/1993 | Hearst et al. | 250/455.11 |
| 5,185,532 A | 2/1993 | Zabsky et al. | 250/455.11 |
| 5,192,264 A | 3/1993 | Fossel | 604/4 |
| 5,211,960 A | 5/1993 | Babior | |
| 5,216,251 A | 6/1993 | Matschke | 250/455.11 |
| 5,229,081 A | 7/1993 | Suda | 427/186 |
| 5,232,844 A | 8/1993 | Horowitz et al. | 435/173.1 |
| 5,234,808 A | 8/1993 | Murphy | 435/2 |
| 5,236,716 A | 8/1993 | Carmen et al. | 424/532 |
| 5,247,178 A | 9/1993 | Ury et al. | 250/438 |
| 5,248,506 A | 9/1993 | Holme et al. | 424/533 |
| 5,250,303 A | 10/1993 | Meryman et al. | 424/533 |
| 5,258,124 A | 11/1993 | Bolton et al. | 210/748 |
| 5,269,946 A | 12/1993 | Goldhaber et al. | 210/767 |
| 5,273,713 A | 12/1993 | Levy | 422/22 |
| 5,281,392 A | 1/1994 | Rubinstein | |
| 5,288,605 A | 2/1994 | Lin et al. | 435/902 |
| 5,288,647 A | 2/1994 | Zimlich, Jr. et al. | 436/174 |
| 5,290,221 A | 3/1994 | Wolf, Jr. et al. | 604/4 |
| 5,300,019 A | 4/1994 | Bischof et al. | 604/4 |
| 5,304,113 A | 4/1994 | Sieber et al. | 604/4 |
| 5,318,023 A | 6/1994 | Vari et al. | 128/633 |
| 5,340,716 A | 8/1994 | Ullman et al. | 435/6 |
| 5,342,752 A | 8/1994 | Platz et al. | 435/2 |
| 5,344,752 A | 9/1994 | Murphy | 435/2 |
| 5,344,918 A | 9/1994 | Dazey et al. | 530/381 |
| 5,358,844 A | 10/1994 | Stossel et al. | 435/2 |
| 5,360,734 A | 11/1994 | Chapman et al. | 435/238 |
| 5,366,440 A | 11/1994 | Fossel | 604/4 |
| 5,376,524 A | 12/1994 | Murphy et al. | 435/2 |
| 5,378,601 A | 1/1995 | Gepner-Puszkin | 435/2 |
| 5,418,130 A | 5/1995 | Platz et al. | 435/2 |
| 5,419,759 A | 5/1995 | Naficy | 604/5 |
| 5,427,695 A | 6/1995 | Brown | 210/805 |
| 5,433,738 A | 7/1995 | Stinson | 607/92 |
| 5,459,030 A | 10/1995 | Lin et al. | 435/2 |
| 5,466,573 A | 11/1995 | Murphy et al. | 435/2 |
| 5,474,891 A | 12/1995 | Murphy | 435/2 |
| 5,482,828 A | 1/1996 | Lin et al. | 435/2 |
| 5,487,971 A | 1/1996 | Holme et al. | 435/2 |
| 5,494,590 A | 2/1996 | Smith et al. | 210/782 |
| 5,503,721 A | 4/1996 | Hearst et al. | 204/157.6 |
| 5,512,187 A | 4/1996 | Buchholz et al. | |
| 5,516,629 A | 5/1996 | Park et al. | 435/2 |
| 5,527,704 A | 6/1996 | Wolf, Jr. et al. | 435/283.1 |
| 5,536,238 A | 7/1996 | Bischof | 604/6 |
| 5,545,516 A | 8/1996 | Wagner | 435/2 |

| | | | |
|---|---|---|---|
| 5,547,635 A | 8/1996 | Duthie, Jr. ............... 422/24 |
| 5,550,111 A | 8/1996 | Suhadolnik et al. ........ 514/44 |
| 5,556,958 A | 9/1996 | Carroll et al. ............ 536/25.3 |
| 5,556,993 A | 9/1996 | Wollowitz et al. ......... 549/282 |
| 5,557,098 A | 9/1996 | D'Silva ................... 250/222.1 |
| 5,569,579 A | 10/1996 | Murphy ..................... 435/2 |
| 5,571,666 A | 11/1996 | Floyd et al. ................ 435/2 |
| 5,587,490 A | 12/1996 | Goodrich, Jr. et al. ...... 549/282 |
| 5,593,823 A | 1/1997 | Wollowitz et al. ............. 435/2 |
| 5,597,722 A | 1/1997 | Chapman et al. ........... 435/238 |
| 5,607,924 A | 3/1997 | Magda et al. ................ 514/44 |
| 5,622,867 A | 4/1997 | Livesey et al. ............... 436/18 |
| 5,624,435 A | 4/1997 | Furumoto et al. ............ 606/10 |
| 5,624,794 A | 4/1997 | Bitensky et al. .............. 435/2 |
| 5,628,727 A | 5/1997 | Hakky et al. ................. 604/6 |
| 5,639,376 A | 6/1997 | Lee et al. .................... 210/645 |
| 5,639,382 A | 6/1997 | Brown ....................... 210/739 |
| 5,643,334 A | 7/1997 | Eckhouse et al. ............. 607/88 |
| 5,652,096 A | 7/1997 | Cimino ......................... 435/6 |
| 5,653,887 A | 8/1997 | Wahl et al. .................. 210/745 |
| 5,654,443 A | 8/1997 | Wollowitz et al. .......... 549/282 |
| 5,656,154 A | 8/1997 | Meryman |
| 5,656,498 A | 8/1997 | Iijima et al. |
| 5,658,530 A | 8/1997 | Dunn ......................... 422/24 |
| 5,658,722 A | 8/1997 | Margolis-Nunno et al. .... 435/2 |
| 5,683,661 A | 11/1997 | Hearst et al. ............ 422/186.3 |
| 5,683,768 A | 11/1997 | Shang et al. ................ 428/35.2 |
| 5,686,436 A | 11/1997 | Van Dyke ................... 514/171 |
| 5,688,475 A | 11/1997 | Duthie, Jr. ............... 422/186.3 |
| 5,691,132 A | 11/1997 | Wollowitz et al. ............. 435/2 |
| 5,698,524 A | 12/1997 | Mach ........................... 514/22 |
| 5,698,677 A | 12/1997 | Eibl et al. ................... 530/381 |
| 5,702,684 A | 12/1997 | McCoy et al. ............. 424/10.3 |
| 5,707,401 A | 1/1998 | Talmore ....................... 607/88 |
| 5,709,653 A | 1/1998 | Leone ......................... 604/20 |
| 5,709,991 A | 1/1998 | Lin et al. ....................... 435/2 |
| 5,709,992 A | 1/1998 | Rubinstein |
| 5,712,085 A | 1/1998 | Wollowitz et al. .......... 465/148 |
| 5,712,086 A | 1/1998 | Horowitz et al. .............. 435/2 |
| 5,714,328 A | 2/1998 | Magda et al. .................. 435/6 |
| 5,736,313 A | 4/1998 | Spargo et al. ................. 435/2 |
| 5,739,013 A | 4/1998 | Budowsky et al. ......... 435/91.1 |
| 5,753,428 A | 5/1998 | Yuasa et al. ................... 435/2 |
| 5,756,553 A | 5/1998 | Iguchi et al. ............. 514/772.3 |
| 5,769,839 A | 6/1998 | Carmen et al. ............. 604/408 |
| 5,772,960 A | 6/1998 | Ito et al. ........................ 422/41 |
| 5,783,093 A | 7/1998 | Holme ........................ 210/767 |
| 5,789,150 A | 8/1998 | Margolis-Nunno et al. .... 435/2 |
| 5,789,151 A | 8/1998 | Bitensky et al. ............... 435/2 |
| 5,789,601 A | 8/1998 | Park et al. ................... 549/283 |
| 5,798,238 A | 8/1998 | Goodrich, Jr. et al. ... 435/173.3 |
| 5,798,523 A | 8/1998 | Villenueve et al. ......... 250/234 |
| 5,811,144 A | 9/1998 | Bordeleau et al. ........ 426/330.4 |
| 5,817,519 A | 10/1998 | Zelmanovic et al. ......... 436/63 |
| 5,827,644 A | 10/1998 | Floyd et al. .................... 435/2 |
| 5,834,198 A | 11/1998 | Famulok et al. ............... 435/6 |
| 5,840,252 A | 11/1998 | Giertych ....................... 422/40 |
| 5,843,459 A | 12/1998 | Wang et al. .............. 424/231.1 |
| 5,846,961 A | 12/1998 | Van Dyke ................... 514/171 |
| 5,854,967 A | 12/1998 | Hearst et al. ............. 422/186.3 |
| 5,858,643 A | 1/1999 | Ben-Hur et al. ............... 435/2 |
| 5,866,074 A | 2/1999 | Chapman et al. ........ 422/82.09 |
| 5,869,701 A | 2/1999 | Park et al. ................... 549/283 |
| 5,871,900 A | 2/1999 | Wollowitz et al. ............. 435/2 |
| 5,876,676 A | 3/1999 | Stossel et al. ................ 422/12 |
| 5,891,705 A | 4/1999 | Budowsky et al. ......... 435/238 |
| 5,899,874 A | 5/1999 | Jonsson ......................... 604/4 |
| 5,906,915 A | 5/1999 | Payrat et al. ................... 435/2 |
| 5,908,742 A | 6/1999 | Lin et al. ....................... 435/2 |
| 5,919,614 A | 7/1999 | Livesey et al. |
| 5,922,278 A | 7/1999 | Chapman et al. ............. 422/22 |
| 5,935,092 A | 8/1999 | Sun et al. ....................... 604/4 |
| 5,955,256 A | 9/1999 | Sowemimo-Coker et al. . 435/2 |
| 5,955,257 A | 9/1999 | Burger et al. ................... 435/2 |
| 5,965,349 A | 10/1999 | Lin et al. ....................... 435/2 |
| 5,976,884 A | 11/1999 | Chapman et al. ............ 436/34 |
| 5,981,163 A | 11/1999 | Horowitz et al. ............... 435/4 |
| 6,017,691 A | 1/2000 | Wollowitz et al. ............. 435/2 |
| 6,020,333 A | 2/2000 | Berque ....................... 514/251 |
| 6,060,233 A | 5/2000 | Wiggins |
| 6,063,624 A | 5/2000 | Kandler et al. |
| 6,077,659 A | 6/2000 | Ben-Hur et al. ............... 435/2 |
| 6,087,141 A * | 7/2000 | Margolis-Nunno et al. .................... 435/173.3 |
| 6,214,534 B1 | 4/2001 | Horowitz et al. ............... 435/2 |
| 6,232,434 B1 | 5/2001 | Stamler et al. .............. 528/373 |
| 6,251,644 B1* | 6/2001 | Sowemimo-Coker et al. ........................ 435/173.3 |
| 6,268,120 B1* | 7/2001 | Platz et al. ..................... 435/2 |
| 6,270,952 B1 | 8/2001 | Cook et al. .................... 435/2 |
| 6,294,361 B1 | 9/2001 | Horowitz et al. ......... 435/173.3 |
| 6,548,241 B1 | 4/2003 | McBurney et al. ............ 435/2 |
| 2001/0024781 A1 | 9/2001 | Platz et al. ..................... 435/2 |
| 2003/0073650 A1 | 4/2003 | Reddy et al. ................. 514/43 |
| 2003/0077264 A1 | 4/2003 | Goodrich .................. 424/93.72 |

FOREIGN PATENT DOCUMENTS

| | | |
|---|---|---|
| EP | 0 066886 | 6/1982 |
| EP | 0 124 363 | 4/1984 |
| EP | 0108588 | 5/1984 |
| EP | 0 196 515 A1 | 3/1986 |
| EP | 0 184 331 A2 | 6/1986 |
| EP | 0196515 | 10/1986 |
| EP | 196515 | 10/1986 |
| EP | 0 491/757 | 9/1990 |
| EP | 0 491 757 B1 | 9/1990 |
| EP | 0 525 138 B1 | 12/1991 |
| EP | 0590514 A1 | 4/1994 |
| EP | 0 679 398 A | 11/1995 |
| EP | 0 679 398 A1 | 11/1995 |
| EP | 0679398 | 11/1995 |
| EP | 0 510 185 B1 | 12/1996 |
| EP | 0510185 B1 | 12/1996 |
| EP | 0754461 A2 | 1/1997 |
| EP | 0 801 072 A2 | 3/1997 |
| EP | 0 801 072 A2 | 10/1997 |
| FR | 2674753 | 10/1992 |
| FR | 2715303 | 7/1995 |
| FR | 2718353 | 10/1995 |
| GB | 2034463 A | 6/1980 |
| WO | WO 83/02328 | 7/1983 |
| WO | WO 85/02116 | 5/1985 |
| WO | WO 89/06702 | 7/1989 |
| WO | WO 90/00059 | 1/1990 |
| WO | WO 91/02529 | 3/1991 |
| WO | WO 92/08348 | 5/1992 |
| WO | WO 92/08349 | 5/1992 |
| WO | WO 92/11057 | 7/1992 |
| WO | WO 92/17173 | 10/1992 |
| WO | WO 93/00005 | 1/1993 |
| WO | WO 94/07426 | 4/1994 |
| WO | WO94/07426 | 4/1994 |
| WO | WO 94/07499 | 4/1994 |
| WO | WO 95/02325 | 1/1995 |
| WO | WO 95/11028 | 4/1995 |
| WO | WO 95/12973 | 5/1995 |
| WO | WO 95/16348 | 6/1995 |
| WO | WO 96/14740 | 5/1996 |
| WO | WO96/14740 | 5/1996 |
| WO | WO 96/14741 | 5/1996 |
| WO | WO 96/39816 | 12/1996 |
| WO | 97/07674 | 3/1997 |
| WO | WO 97/07674 | 3/1997 |
| WO | WO 97/18844 | 5/1997 |
| WO | WO 97/22245 | 6/1997 |

| WO | WO 97/36581 | 10/1997 |
| WO | WO 97/36634 | 10/1997 |
| WO | WO 98/30545 | 7/1998 |
| WO | WO 98/31219 | 7/1998 |
| WO | WO 98/41087 | 9/1998 |
| WO | WO 98/51147 | 11/1998 |
| WO | WO 98/56247 | 12/1998 |
| WO | WO 99/11305 | 3/1999 |
| WO | WO99/11305 | 9/1999 |
| WO | WO 99/11305 | 11/1999 |
| WO | WO 99/59645 | 11/1999 |
| WO | WO 00/04930 | 2/2000 |
| WO | WO00/04930 | 2/2000 |
| WO | WO 00/11946 | 3/2000 |
| WO | WO 01/23413 | 4/2001 |
| WO | WO 01/28599 | 4/2001 |
| WO | WO 01/66172 | 9/2001 |
| WO | WO 01/94349 | 12/2001 |
| WO | WO 01/96340 | 12/2001 |
| WO | WO 02/26270 | 4/2002 |
| WO | WO 02/32469 | 4/2002 |
| WO | WO 02/43485 | 6/2002 |

OTHER PUBLICATIONS

Bar-Meir M. et al, "Effect of various agents on adenosine triphosphate synthesis in mitochondrial complex I deficiency," (Dec. 2001) Biosis Database Accession No. PREV200200100727 (abstract only).

Bauer et al., "Nitric oxide donors: biochemical pharmacology and therapeutics," (1995) *Advances in Pharmacology* 34:361.

Cadet, J. et al., "Mechanisms and products of photosensitized degradation of nucleic acids and related model compounds," (1983) *Israel J. Chem.* 23:420-429.

Chávez, E. et al., "Oxygen free-radicals mediate the damaging effect of ultraviolet light on membrane mitochondria," (Sep. 1998) *Biochem. Mol. Int.* 46(1):207-214.

Dumont, L.J. et al., "Seven-day storage of single-donor platelets: recovery and survival in an autologous transfusion study,"(Jul. 2002) *Transfusion* 42:847-854.

Dumont, L.J. et al., "Autologous transfusion recovery of WBC-reduced high-concentration platelet concentrates," (Oct. 2002) *Transfusion* 42:1333-1339.

Goodrich, R.P. et al., "The design and development of selective, photoactivated drugs for sterilization of blood products," (1997) *Drugs of the Future* 22(2):159-171.

Grossman, B.J. et al., "Screening blood donors for gastrointestinal illness: a strategy to eliminate carriers of *Yersinia enterocolitica*," (1991) *Transfusion* 31:500-501.

Heal, J.M. et al., "Fatal *Salmonella* septicemia after platelet transfusion," (1987) *Transfusion* 27(1):2-5.

Hoffman, M.E. et al., "DNA strand breaks in mammalian cells exposed to light in the presence of riboflavin and tryptophan," (1979) *Photochemistry and Photobiology* 29:299-303.

Korycka-Dahl, M. and Richardson, T. (1980), "Photodegradation of DNA with fluorescent light in the presence of riboflavin and photoprotection by flavin triplet-state quenchers," *Biochimica et Biophysica Acta* 610:229-234.

Kuratomi, K. and Kobayashi, Y., "Studies on the interactions between DNA and flavins," (1977) *Biochimica et Biophisica Acta* 476:207-217.

Lozinova T.A. et al., "ADP effect on light-induced oxygen absorption by flavins," (1986) Biosis Database Accession No. PREV198682038493 (abstract only).

Masaki, H. and Sakurai, H., "Increased generation of hydrogen peroxide possibly from mitochondrial respiraotry chain after UVB irradiation of murine fibroblasts," (Mar. 1997) *J. Dermatol. Sci.* 14(3):207-216.

Murphy, S. and Gardner, F.H., "Platelet preservation. Effect of storage temperature on maintenance of platelet viability—deleterious effect of refrigerated storage," (1969), *New Eng. J. Med.* 280(20):1094-1098.

Myhre, B.A., "Fatalities from blood transfusion," (1980) *JAMA* 244(12):13331335.

Peak, J.G. et al., "DNA breakage caused by 334-nm ultraviolet light is enhanced by naturally occurring nucleic acid components and nucleotide coenzymes," (1984) *Photochemistry and Photobiology* 39(5):713-716.

Piette, J. et al., "Alteration of guanine residues during proflavine mediated photosensitization of DNA," (1981) *Photochemistry and Photobiology* 33:325-333.

Piette, J. et al., "Production of breaks in single- and double-stranded forms of bacteriophage ΦX174 DNA by proflavine and light treatment," (1979) *Photochemistry and Photobiology* 30:369-378.

Saijo, T. "Isoalloxazine Ring of FAD is required for the formation of the core in the Hsp60-assisted folding of medium chain Acyl-CoA dehydrogenase subunit into the assembly competent conformation in mitochondria," (1995) *Journal of Biological Chemistry* 270(4):1899-1907.

Salet, C. and Moreno, G., "Photodynamic action icnreases leakage of the mitochondrial electron transport chain," (Apr. 1995) *Int. J. Radiat. Biol.* 67(4):477-480.

Speck, W.T. et al., "Further observations on the photooxidation of DNA in the presence of riboflavin," (1976) *Biochimica et Biophisica Acta* 435:39-44.

Tsugita, A. et al., "Photosensitized inactivation of ribonucleic acids in the presence of riboflavin," (1965) *Biochimica et Biophisica Acta* 103:360-363.

"An acceptable circular of information for the use of human blood and blood components," (Oct. 2002) USFDA, Center for Biologics Evaluation and Research.

Chow, C.S. and Barton, J.K., "Recognition of G-U mismatches by tris(4,7-diphenyl-1, 10- phenanthroline)rhodium(III)," (1992) *Biochemistry* 31(24):5423-5429.

Ennever, J.F. and Speck, W.T., "Short Communication. Photochemical Reactions of Riboflavin: Covalent Binding to DNA and to Poly (dA) Poly (dT)," (1983) *Pediatr. Res.* 17:234-236.

Goodrich, R.P. and Platz, M.S.. "The design and development of selective, photoactivated drugs for sterilization of blood products," (1997) *Drugs of the Future* 22(2):159-171.

Joshi, P.C., "Comparison of the DNA-damaging property of photosensitized riboflavin via singler oxygen ($^1O$:) and superoxide radical ($O$;) mechanisms," (1985) *Toxicology Letters* 26:211-217.

Kabuta, H. et al. (1978), "Inactivation of viruses by dyes and visible light," Chem. Abstracts 87(1), Abstract No. 400626.

Kale, H. et al. (1992), "Assessment of the genotoxic potential of riboflavin and lumiflavin; B. Effect of light." Mutation Res. 298:17-23.

Kobayashi et al. (1983), "The molecular mechanism of mutation. Photodynamic action of flavins on the RNA-synthesizing system." Chem. Abstracts 98(1). Abstract No. 1200.

Koryeka-Dahl, M. and Richardson, T., "Photodegradation of DNA with fluorescent light in the presence of riboflavin, and photoprotection by flavin triple-state quenchers," (1980) *Biochimica et Biophysica Acta* 610:229-234.

Kovalsky, O.I. and Budowsky, E.I., "Laser (Two-Quantum) Photolysis of Polynucleotides and Nucleoproteins: Quantitative Processing of Results," 1990, *Photochemistry and Photobiology* 5(6):659-665.

Kuratomi, K. and Kobayashi, Y., "Studies on the Interactions Between DNA and Flavins." (1977) *Biochemica et Biophysica Acta* 476:207-217.

Maddox, J., "The working of vitamin K." (1991) *Nature* 353(6346):695.

Matthews, J.L. et al., "Photodynamic therapy of viral contaminants with potential for blood banking applications." (1988) *Transfusion* 28(1):81-83.

Murata, A. et al., "Effect of vitamins other than vitamin C on viruses: virus-inactivating activity of vitamin K5." (1983) *J. Nutr. Sci. Vitaminol (Tokyo)* 29(6):721-724.

Naseem, I. et al., "Effect of alkylated and intercalated DNA on the generation of superoxide anion by riboflavin." (1988) *Bioscience Reports* 8(5):485-492.

North, J. et al. (1993), "New Trends in Photobiology (Invited Review)," J. Photochem. Photobiol. B: Biol. 17:99-108.

Piette, J. et al., "Alteration of Guanine Residues During Proflaving Mediated Photosensitization of DNA." (1981) *Photochemistry and Photobiology* 33:325-333.

Pratt, R. et al., "Vitamin K; as an Antimicrobial Medicament and Preservative," (1950) *J. Am. Pharm. Ass'n* 39(3):127-134.

Tsugita, A. et al., "Photosensitized inactivation of ribonucleic acids in the presence of riboflavin," (1965) *Biochim. Biophys. Acta* 103:360-363.

Angreu, G., Boccaccio, C., Lecrubler, C. and Fretault, J. "*UV-a Irradiation of Platelet Concentrates (PC): Feasibility in Transfusion Practice,*" Blood Bank Hematology and Biophysics Laboratories, Abstract Supplement, Abstract S146, Abstract No. 42S.

Cadet, J., Decarroz, C. Want, S.Y. and Midden, W.R., "*Mechanisms and Products of Photosensitized Degradation of Nucleic Acids and Related Model Compounds*," Israel Journal of Chemistry, vol. 23 (1983) pp. 420-429.

Cole, M., Stromberg, L. Friedman, L. Benade, L. and Shumaker, J., "*Photochemical Inactivation of Virus In Red Cells*," American Red Cross, Abstract Supplement, Abstract S145, Abstract No. 42S.

Ennever, John F. and Speck, William T., "*Short Communication. Photochemical Reactions of Riboflavin: covalent Binding to DNA and to Poly (dA) Poly (dT)*," Pediatr. Res. 17: (1983) pp. 234-236.

Hoffmann, Edwiges M. and Meneghini, Rogerlo, "*DNA Strand Breaks In mammallan Cells Exposed to Light in the Presence of Riboflavin and Tryptophan*," Photochemistry and Photobiology vol. 29, pp. 299-303 (1979).

Korycka-Dahl, Malgorzata and Richardson, Thomas, "*Photodegradation of DNA with Fluorescent Light in the Presence of-Riboflavin and Photoprotection by Flavin Triplet-State Quenchers*," Biochimica at Biophysica Acta, 610 (1980) pp. 229-234.

Kuratomi, Kazuoki and Kobayashi, Yasuko "*Studies on the interactions Between DNA and Flavins*," Biochimica et Biophysica Acta, 476 (1977) pp. 207-217.

Neyndorff, H.C., Bartel, F., Tufaro, and Levy, J.G., "*Development Of A Model To Demonstrate Photosensitizer- mediated Viral Inactivation in Blood*," Quadra Logic Technologies, Inc., and the Department of Microbiology, University of British Columbia 485-490 (Feb. 6, 1990).

Peak, J.G., Peak, M.J. and MacCoss, M., "*DNA Breakage caused by 334-nm Ultraviolet Light is Enhanced by Naturally Occurring Nucleic Acid Components and Nucleotide Coenzymes*," Photochemistry and Photobiology vol. 39, (1984) pp. 713-716.

Piette, J. Calberg-Bacq, C.M., and Van De Vorst, A., "*Alteration of Guanine Residues During Proflavine Mediated Photosensitization of DNA*," Photochemistry and Photobiology vol. 33, (1981) pp. 325-333.

Piette, J. Calberg-Bacq, C.M., and Van De Vorst, A., "*Production of Breaks in Single and Double-Stranded Forms of Bacteriophage ΦX174 DNA by Proflavine and Light Treatment*," Photochemistry and Photobiology vol. 30, (1979) pp. 369-378.

Speck, William T., Rosenkranze, Samuel, Rosenkranze, Herbert S., "*Further Observations on the Photooxidation of DNA in the Presence of Riboflavin*," Biochimica et Biophysica Acta, 435 (1976) pp. 39-44.

Tsugita, Akira, Okada, Yoshiko and Uehara, Kihachiro, "*Photosensitized Inactivation Of Ribonucleic Acids In The Presence Of Ribflavin*," Biochim. Biophys. Acta. 360-363 (1965).

Friedman, L.I. et al:, (1995), "Reducing the infectivity of blood components—what we have learned", Immun. Invest. 24(1&2):49-71.

Ghiron, C.A. and Spikes, J.D., (1965), "The flavin-sensitized photoinactivation of trypsin", Photochem. and Photobio. 4:13-26.

Hanson, C.V., (Mar. 1979), "Photochemical Inactivation of Deoxyribonucleic and Ribonucleic Acid Viruses by Cholorpromazine", Antimicrob. Agent Chemother, 15(3):461-464.

Hoffman, M.E. and Meneghini, R., (1979), "DNA strand breaks in mammalian cells exposed to light in the presence of riboflavin and tryptophan", Photochem. and Photobio. 29:299-303.

Malik et al., (1990), "New trends in photobiology—bactericidal effects of photoactivated porphyrins—an alternative approach to antimicrobial drugs", J. Photochem. Photobiol. Pt. B:Biology, 5:281-293.

North et al. ((993), "Photosensitizers as Virucidal Agents", J. Photobiol, 17(2):99-108.

U.S. Appl. No. 08/924,519, filed Sep. 5, 1997, Keller et al.

Abdurashidova, G.G. et al., "Polynucleotide-protein itneractions in the translation system. Identification of proteins itneracting with tRNA in the A- and P-sites of *E. coli* ribosomes," (1979) *Nucleic Acids Res.* 6(12):3891-3909.

Budowsky, E.I. et al., "Induction of polynucleotide-protein crosslinkages by ultraviolet irradiation," (1986) *Eur. J. Biochem.* 159:95-101.

Budowsky, E.I. and Abdurashidova, G.G., "Polynucleotide-Protein Cross-Links Induced by Ultraviolet Light and Their Use for Structural Investigation of Nucleoproteins," (1989) *Progress in Nucleic Acid Res. and Mol Biol.* 37:1-65.

Budowsky, E.I., "Problems and Prospects for Preparation of Killed Antiviral Vaccines," (1991) *Adv. Virus Res.* 39:255-290.

Budowsky, E.I. et al., "Principles of selective inactivation of viral genome. VI. Inactivation of the infectivity of the influenza virus by the accion of β-propiolactone," (1991) *Vaccine* 9:398-402.

Budowsky, E.I. et al., "Principles of selective inactivation of viral genome. VII. Some peculiarities in determination of viral suspension infectivity during inactivation by chemical agents," (1991) *Vaccine* 9:473-476.

Budowsky, E.I. et al., "Principles of selective inactivation of viral genome. VIII. The influence of β-propiolactone on immunogenic and protective activities of influenza virus," (1993) *Vaccine* 11(3):343-348.

Budowsky, E.I. et al., "Preparation of cyclic 2', 3'-monophosphates of oligoadenylates (A2'p) A>p and A3'p(A2'p). ,A>p," (1994) *Eur. J. Biochem.* 220:97-104.

Goodrich, R.P. and Platz, M.S., "The design and development of selective, photoactivated drugs for sterilization of blood products," (1997) *Drugs of the Future* 22(2):159-171.

Hoffman, M.E. and Menegnini, R., "DNA Strand Breaks in Mammalian Cells Exposed to Light in the Presence of Riboflavin and Tryptophan," (1979) *Photochemistry and Photobiology* 29:299-303.

Ivanchenko, V.A. et al., "The photochemistry of purine components of nucleic acids. I. The efficiency of photolysis of adenine and guanine derivatives in aqueous solution," (1975) *Nucleic Acids Res.* 2(8):1365-1373.

Korycka-Dahl, M. and Richardson, T., "Photodegradation of DNA with Fluorescent Light in the Presence of Riboflavin, and Photoprotection by Flavin Triplet-State Quenchers," (1980) *Biochemica et Biophysica Acta* 610:229-234.

Simukova, N.A. and Budowsky, E.I., "Converstion of Non-Covalent Interactions in Nucleoproteins into Covalent Bonds: UV-Induced Formation of Polynucleotide-Protein Crosslinks in Bacteriophage Sd Virions," (1974) *FEBS Letters* 38(3):299-303.

Webb, R.B. and Malina, M.M., "Mutagenesis in *Escherichia coli* by Visible Light," (1967) *Science* 156:1104-1105.

Kabuta, H. et al., "Inactivation of viruses by dyes and visible light,"(1978) *Chemical Abstracts* 87(1), Abstract No. 400626.

Kale, H. et al., "Assessment of the genotoxic potential of riboflavin and lumiflavin; B. Effect of light," (1992) *Mutation Research* 298:17-23.

Kobayashi et al., "The molecular mechanism of mutation. Photodynamic action of flavins on the RNA-synthesizing system," (1983) *Chemical Abstracts* 98(1) Abstract No. 1200.

Product advertisement for "Ultracure 100SS Plus Specifications," EFOS USA, Inc., Williamsville, NY, USA.

North, J. et al., "Photosensitizers as virucidal agents," (1993) *J. Photochem. Photobiol 8: Biol.* 17:99-108.

Tsugita et al., "Photosentized inactivation of ribonucleic acids in the presence of riboflavin," (1965) *Biochim. Biophys. Acta* 103:360-363.

Webb, R.B. and Malina, M.M., "Mutagenesis is *Escherichia coli* by visible light," (1967) *Science* 156:1104-1105.

Brodie, A.F. and Watanabe, T., "Mode of action of vitamin K in microorganisms," (1966) *Vitam. Horm.* 24:447-463.

Chow, C.S. and Barton, J.K., "Recognition of G-U mismatches by tris(4,7-diphenyl-1,10-phenanthroline)rhodium(III),"(1992) *Biochemistry* 31(24):5423-5429.

Deutsch, E., "Vitamin K in medical practice: adults," (1966) *Vitam. Horm.* 24:665-680.

Klebanoff, M.A. et al., "The risk of childhood cancer after neonatal exposure to vitamin K," (1993) *New Eng.. J. Med.* 329(13):905-908.

Korycka-Dahl, M. and Richardson, T., "Photodegradation of DNA with fluorescent light in the presence of riboflavin, and photoprotection by flavin triplet-state quenchers," (1980) *Biochimica et Biophysica Acta* 610:229-234.

Leontis, N.B. and Westof, E., "The 5S rRNA loop E: chemical probing and phylogenetic data versus crystal structure," (1998) *RNA* 4:1134-1153.

Lim, A.C. and Barton, J.K., "Chemical probing of tDNA $^{Phe}$ with transition metal complexes: a structural comparison of RNA and DNA," (1993) *Biochemistry* 32:11029-11034.

McCord, E.F., "Chemically induced dynamic nuclear polarization studies of yeast," (1984) *Biochemistry* 23:1935-1939.

Merenstein, G.B. et al. (Vitamin K Ad Hoc Task Force), "Controversies concerning vitamin K and the newborn," (1993) *Pediatrics* 91(5):1001-1003.

Merrifield, L.S. and Yang, H.Y., "Factors affecting the antimicrobial activity of vitamin K5," (1965) *Appl. Microbiol.* 13(5):766-770.

Merrifield, L.S. and Yang, H.Y., "Vitamin K5 as a fungistatic agent," (1965) *Applied Microbiol.* 13(5):660-662.

Naseem, I. et al., "Effect of alkylated and intercalated DNA on the generation of superoxide anion by riboflavin," (1988) *Bioscience Reports* 8(5):485-492.

Pratt, R. et al., "Vitamin K$_5$ as an Antimicrobial Medicament and Preservative," (1950) *J. Am. Pharm. Ass'n* 39(3):127-134.

Shwartzman, G., "Antibacterial Properties of 4-Amino-2-Methyl-1-Naphthol Hydrochloride," (1948) *Proc. Soc. Exp. Biol. Med.* 67:376-378.

Spranger, J., "Does vitamin K cause cancer?" (1993) *Eur. J. Pediatr.* .52(2):174.

Vest, M., "Vitamin K in medical practice: pediatrics," (1966) *Vitam. Horm.* 24:649-663.

Yang, H.Y. et al., "Vitamin K$_5$ as a Food Preservative," (1958) *Food Technology* 501-504.

Friedman, L.I. et al., "Reducing the infectivity of blood components—what we have learned," (1995) *Immunological Investigations* 24(1&2):49-71.

Ghiron, C.A. and Spikes, J.D., "The flavin-sensitized photoinactivation of trypsin," (1965) *Photochemistry and Photobiology* 4:13-26.

Hoffman, M.E. and Meneghini, R., "DNA strand breaks in mammalian cells exposed to light in the presence of riboflavin and tryptophan," (1979) *Photochemistry and Photobiology* 29:299-303.

CAS Printout for Herfeld et al. Lab. Chim. Ther., Fac. Sci. Pharm. Biol. 5: 67-76, Jan. 1994.

Koziol et al., Bull. Pol. Acad. Sci. 39: 37-9, Jan. 1991.

Tyrakowska et al. J. Photochem. Photobiol. A.: Chem 72:235-241, Jan. 1993.

Schoo et al. Macromolecules 25: 1633-1638, Jan. 1992.

Herfeld et al. Anti-Cancer drug Design 13: 337-359, 1998.

CAS Printout for Herfeld et al. Anti-Cancer Drug Design 13: 337-359, 1998.

Uehara K. et al. "Effect of adenine on the riboflavin-sensitized photoreaction. II. Effect of adenine on the photodynamic inactivation of transforming deoxyribonucleic acid in the presence of riboflavin," The Journal of Biochemistry, vol. 71, No. 5, 1972, pp. 805-810.

Uehara K. et al. "Effect of adenine on the riboflavin-sensitized photoreaction. II. Effect of adenine on the photodynamic inactivation of yeast alcohol dehydrogenase in the presence of riboflavin," The Journal of Vitaminology, vol. 17, No. 3, 1971, pp. 148-154.

Reinhardt A. et al. "Virucidal activity of retinal," Antimicrobial Agents and Chemotherapy, vol. 16, No. 3, Sep. 1979 (1979-09), pp. 421-423.

Budowsky, E. I. et al., "Preparation of cyclic, 2',3'-monophosphates of oligoadenylates (A2'p)$_n$ A>p and A3'p(A2'p)$_{n-1}$ A>p," (1994) *Eur. J. Biochem.* 220:97-104.

Joshi, P.C., "Comparison of the DNA-damaging property of photosensitized riboflavin via singlet oxygen ($^1O_2$) and superoxide radical ($O_i^-$) mechanisms," (1985) *Toxicology Letters* 26:211-217.

Kobayashi et al. (1983), "The molecular mechanism of mutation. Photodynamic action of flavins on the RNA-synthesizing system," Chem. Abstracts 98(1), Abstract No. 1200.

Leontis, N.B. and Westhof, E., "The 5S rRNA loop E: chemical probing and phylogenetic data versus crystal structure," (1998) *RNA* 4:1134-1153.

Lim, A.C. and Barton, J.K., "Chemical probing of rDNA $^{Phe}$ with transition metal complexes: a structural comparison of RNA and DNA," (1993) *Biochemistry* 32:11029-11034.

Maddox, J., "The working of vitamin K," (1991) *Nature* 353(6346):695.

Matthews, U.L. et al., "Photodynamic therapy of viral contaminants with potential for blood banking applications," (1988) *Transfusion* 28(1):81-83.

Simukova, N.A. and Budowsky, E.I., "Conversion of Non-Covalent Interactions in Nucleoproteins into Covalent Bonds: UV-Induced Formation of Polynucleotide-Protein Crosslinks in Bacteriophage Sd Virions," (1974) *FEBS Letters* 38(3):299-303.

Spranger, J., "Does vitamin K cause cancer?" (1993) *Eur. J. Pediatr.* 152(2) 174.

Yang, H.Y. et al., "Vitamin K$_5$ as a Food Preservative," (1958) *Food Technology* 501-504.

Berezovskii, V.M. and Eremenko, T.V. (1961), "Studies in the Allo- and Isoalloxazine Series. IV. New Synthesis of 2'-Desoxyriboflavin and Synthesis," J. Gen. Chem. USSR 31(11):3575-3578.

Bhatia, J. et al. (1983), "Riboflavin Enhances Photo-oxidation of Amino Acids under Simulated Clinical Conditions," J. Parenteral Enteral Nutr. 7(3):277-279.

Cairns, W.L. and Metzler, D.E. (1971), "Photochemical Degradation of Flavins. VI. A New Photoproduct and Its Use in Studying the Photolytic Mechanism," J. Am. Chem. Soc. 93:2772-2777.

Cerman, I. and Hais, I.M. (1972), "Esters of 6,7-Dimethyl-9-hydroxymethylisoalloxazine as Photodegradation Products of Riboflavin and Formylmethylflavin in Media Containing Fatty Acids," J. Am. Chem. Soc. 94(5):1741-1742.

Chastain, J.L. and McCormick, D.B. (1991) in *Chemistry and Biochemistry of Flavoenzymes*, vol. I, Chapter 6, Muller, F. (ed.), CRC Press, Boston, pp. 195-200.

Chastain, J.L. and McCormick, D.B. (1987), "Clarification and Quantitation of Primary (Tissue) and Secondary (Microbial) Catabolites of Riboflavin That are Excreted in Mammalian (Rat) Urine." J. Nutr., pp. 468-475.

U.S. Appl. No. 09/119,666, filed Jul. 21, 1998, Goodrich et al.

U.S. Appl. No. 09/357,188, filed Jul. 20, 1999, Goodrich et al.

Edwards, A.M. et al. (1994), "Visible light effects on tumoral cells in a culture medium enriched with tryptophan and riboflavin," J. Photochem. Photobiol. B: Biol. 24:179-186.

Ennever, J.F. et al. (1983), "Potential for Genetic Damage from Multivitamin Solutions Exposed to Phototherapy Illumination," Pediatr. Res. 17:192-194.

Ennever, J.F. and Speck, W.T. (1983), "Short Communication. Photochemical Reactions of Riboflavin: Covalent Binding to DNA and to Poly (dA)•Poly (dT)," Pediatr. Res. 17:234-236.

Everett, J.L. et al. (1952), "Aryl-2-halogenoalkylamines. Part XII: Some Carboxylic Derivatives of NN-Di-2-chloroethylaniline," J. Chem. Soc., pp. 2386-2392.

Fritz, B.J. et al. (1987), "Photochemical Properties of Flavin Derivatives," Photochem. Photobiol. 45(1):113-117.

Fritz, B.J. et al. (1987), "Tripler Lifetimes of Some Flavins," Photochem. Photobiol. 45(4):539-541.

Galston, A.W. (1949), "Riboflavin-sensitized Photooxidation of Indole-acetic Acid and Related Compounds," Proc. Natl. Acad. Sci 35:10-17.

Gomyo, T. and Fujimaki, M. (1970), "Studies on Changes of Protein by Dye Sensitized Photooxidation. Part III. On the Photodecomposition Products of Lysozyme," Agr. Biol. Chem. 34(2):302-309.

Goodrich, R.P. and Platz, M.S. (1997), "The design and development of selective, photoactivated drugs for sterilization of blood products," Drugs of the Future 22(2):159-171.

Gordon-Walker, A. et al. (1970), "Excited States of Flavins Characterised by Absorption, Prompt and Delayed Emission Spectra," Eur. J. Biochem. 13:313-321.

Halwer, M. (1951), "The Photochemistry of Riboflavin and Related Compounds," J. Am. Chem. Soc. 73:4870-4874.

Hemmerich, V.P: (1964), "Flavosemichinon-Metallchelate: Modelle zur Erklärung der "active site" in den mitochondrialen Flavoenzymen Zum Verhalten des Riboflavins gegen Metallionen III," Helv. Chim. Acta 47(55):464-475 (In German).

Holmström (1964), "Spectral studies of the photobleaching of riboflavin phosphate," Arkiv for Kemi 22(23):281-301.

Ito, K. et al. (1993), "Hydroxydeoxyguanosine Formation at the 5' Site of 5'-GG-3' Sequences in Double-stranded DNA by UV Radiation with Riboflavin," J. Biol. Chem. 268(18):13221-13227.

Karrer, V.P. et al. (1934), "Weltere Synthesen Lactoflavin-ähnlicher Verbindungen II," Helv. Chim.. Acta 16:1516-1522 (In German).

Kasai, S. et al. (1988), "Intestinal Absorption of Riboflavin, Studied by an In Situ Circulation System Using Radioactive Analogues," J. Nutr. Sci. Vitaminol. 34:265-280.

Kasai,, H. and Yamaizumi, Z. (1992), "Photosensitized Formation of 7,8-Dihydro-8-oxo-2'-deoxyguanosine (8-Hydroxy-2'-deoxyguanosine) in DNA by Riboflavin: A Non Singlet Oxygen Mediated Reaction," J. Am. Chem. Soc. 114:9692-9694.

Kasai, S. et al: (1990), "Purification, Properties, and Function of Flavokinase from Rat Intestinal Mucosa," J. Biochem. 107:298-303.

Kawai, F. and Tanaka, K. (1970), "Riboflavin-Indoles Interaction in Acid Solution," J. Vitamin. 16:215-218.

Kimmich, G.A. and McCormick, D.B. (1963), "Paper Chromatography of Flavin Analogues," J. Chromatogr. 12:394-400.

Kindack. D.G. et al. (1991), "Separation, identification and determination of lumichrome in swine feed and kidney," Food Additives and Contaminants 8(6):737-748.

Kostenbauder, H.B. et al. (1965), "Photobinding and Photoreactivity of Riboflavin in the Presence of Macromolecules," J. Pharm. Sci. 54(9):1243-1251.

Kurl, R. and Villee, C.A. (1985), "A Metabolite of Riboflavin Binds to the 2,3,7,8-Tetrachlorodibenzo-p-dioxin (TCDD) Receptor," Pharmacology 30:241-244.

Mallesh, K. et al. (1989), "Synthesis and Biological Activities of Some New Substituted Alloxazines and Isoalloxazines: Part 1," Acta Ciencia Indica XV(2):67-74.

McCormick, D.B. (1970), "Flavin Derivatives via Bromination of the 8-Methyl Substituent (1)," J. Heter. Chem. 7:447-450.

Moonen, C.T.W. et al. (1982), "A photo CIDNP study of the active sites of Megasphaera elsdenii and Clostridium MP flavodoxins," FEBS Lett. 149(1):141-146.

Murthy, Y.V.S.N. and Massey, V. (1995), "Chemical Modification of the N-10 Ribityl Side Chain of Flavins," J. Biol. Chem. 270(48):28586-28594.

Nogami, H. et al. (1970), "Pharmacokinetic Aspects of Biliary Excretion. Dose Dependency of Riboflavin in Rat," Chem. Pharm. Bull. 18:228-234.

Ohkawa, H. et al. (1983), "New Metabolites of Riboflavin Appeared in Rat Urine," Biochem. Intl. 6(2):239-247.

Oka, M. and McCormick, D.B. (1985), "Urinary Lumichrome-Level Catabolites of Riboflavin are due to Microbial and Photochemical Events and Not Rat Tissue Enzymatic Cleavage of Ribityl Chain," J. Nutr., pp. 496-499.

Ono, S. et al. (1986), "Effects of Aging on the Formation of Ester Forms of Riboflavin in the Rat Lens," Internat. J. Vit. Nutr. Res. 56:259-262.

Parks, O.W. and Allen, C., "Photodegradation of Riboflavin to Lumichrome in Milk Exposed to Sunlight," J. Diary Sci. 60(7):1038-1041.

Radda, G.K. and Calvin, M. (1964), "Chemical and Photochemical Reductions of Flavin Nucleotides and Analogs," Biochem. 3(3):384-393.

Rivlin, R.S. (1970), "Riboflavin Metabolism," New Engl. J. Med. 283(9): 463-472.

Roughead, Z K. and McCormick, D.B. (1990), "Qualitative and Quantitative Assessment of Flavins in Cow's Milk," J Nutr., pp. 382-388.

Salim-Hanna, M. et al. (1987), "Obtention of a Photo-Induced Addust Between a Vitamin and an Essential Aminoacid. Binding of Riboflavin to Tryptophan," Internat. J. Vit. Nutr: Res. 57:155-159.

Sato, K. et al. (1995), "The Primary Cytotoxicity in Ultraviolet-A-Irradiated Riboflavin Solution is Derived from Hydrogen Peroxide," J. Investig. Dermatol. 105(4):608-612.

Scheindlin, S. et al. (1952), "The Action of Riboflavin on Folic Acid " J. Am. Pharm. Assn. XLI:420-427.

Silva, E. et al. (1994), "Riboflavin-sensitized photoprocesses of tryptophan," J. Photochem. Photobiol. B: Biol. 23:43-48.

Silva, E. and Gaule, J. (1977), "Light-Induced Binding of Riboflavin to Lysozyme," Rad. Environm. Biophys. 14:303-310.

Silva, E. et al. (1991), "A light-induced Tryptophan-riboflavin Binding: Biological Implications," in Nutritional and Toxicological Consequences of Food Processing, Friedman, M. (ed.), Plenum Press, New York, pp. 33-48.

Smith, E.C. and Metzler, D.E. (1963), "The Photochemical Degradation of Riboflavin," J. Am. Chem. Soc. 85:3285-3288.

Song, P-S. and Metzler, D.E. (1967), "Photochemical Degradation of Flavins—, V. Studies of the Anaerobic Photolysis of Riboflavin," Photochem. Photobiol. 6:691-709.

Steczko, J. and Ostrowski, W. (1975), "The Role of Tryptophan Residues and Hydrophobic Interaction in the Binding of Fiboflavin in Egg Yolk Flavoprotein." Biochim. Biophys. Acta 393:253-266.

Swinehart, J.H. and Hess, G.P. (1965), "Riboflavin-Tryptophan Complex Formation as a Criterion for "Buried" and "Exposed" Tryptophyl Residues in Proteins," Biochim. Biophys. Acta 104:205-213.

Tapia, G. and Silva, E. (1991), "Photo-induced riboflavin binding to the tryptophan residues of bovine and human serum albumins," Radiat. Environ. Biophys. 30:131-138.

Toyosaki, T. and Hayashi, A. (1993), "Structural analysis of the products of milk riboflavin photolysis," Milchwissenschaft 48(11):607-609.

Treadwell, G.E. et al. (1968), "Photochemical Degradation of Flavins. V. Chromatographic Studies of the Products of Photolysis of Riboflavin," J. Chromatog. 35:376-388.

Treadwell, G.E., Jr. and Metzler, D.E. (1972), "Photoconversion of Riboflavin to Lumichrome in Plant Tissues," Plant Physiol. 49:991-993.

Van Schagen, C.G. et al. (1982), "Photochemically Induced Dynamic Nuclear Polarization Study on Flavin Adenine Dinucleotide and Flavoproteins," Biochemistry 21:402-407.

Warburg, V.O. and Christian, W. (1932), "Über das neue Oxydationsferment," Naturewiss 20:980-981 (In German).

Woodcock, E.A. et al. (1982), "Riboflavin Photochemical Degradation in Pasta Measured by High Performance Liquid Chromatography," J. Food Sci. 47:545-549.

Yang, C.S. et al. (1964), "Microbiological and Enzymatic Assays of Riboflavin Analogues," J. Nutrition 64:167-172.

Maddox, J. (1991), "The working of vitamin K," Nature 353(6346):695.

Merrifield, L.S. and Yang, H.Y. (1965), "Factors affecting the antimicrobial activity of vitamin K5," Appl. Microbiol. 13(5):766-770.

Merrifield, L.S. and Yang, H.Y. (1965), "Vitamin K5 as a fungistatic agent," Appl. Microbiol. 13(5):660-662.

Murata, A. et al. (1983), "Effect of vitamins other than vitamin C on viruses: virus-Enactivating activity of vitamin K5," J. Nutr. Sci. Vitaminol. (Tokyo) 29(6):721-724.

* cited by examiner

METHOD FOR PREVENTING DAMAGE TO OR REJUVENATING A CELLULAR BLOOD COMPONENT USING MITOCHONDRIAL ENHANCER

CROSS-REFERENCE TO RELATED APPLICATIONS

This application is a continuation-in-part of U.S. application Ser. No. 09/586,147, filed Jun. 2, 2000 now abandoned which is a continuation-in-part of U.S. application Ser. No. 09/357,188, filed Jul. 20, 1999, now U.S. Pat. No. 6,277,337, issued Aug. 21, 2001, which is a continuation-in-part of U.S. application Ser. No. 09/119,666, filed Jul. 21, 1998, now U.S. Pat. No. 6,258,577, issued Jul. 10, 2001. This application is a continuation-in-part of U.S. application Ser. No. 09/777,727, filed Feb. 5, 2001 now U.S. Pat. No. 6,828,323, which is a continuation of U.S. application Ser. No. 09/420,652, filed Oct. 19, 1999, now U.S. Pat. No. 6,268,120, issued Jul. 31, 2001. This application claims priority to U.S. provisional application Ser. No. 60/378,374 filed May 6, 2002. The documents cited above are incorporated herein by reference to the extent not inconsistent herewith.

BACKGROUND OF THE INVENTION

Whole blood collected from volunteer donors for transfusion recipients is typically separated into its components, red blood cells, platelets, and plasma, by apheresis or other known methods. Each of these fractions are individually stored and used to treat a multiplicity of specific conditions and disease states. For example, the red blood cell component is used to treat anemia, the concentrated platelet component is used to control bleeding, and the plasma component is used frequently as a source of Clotting Factor VIII for the treatment of hemophilia.

In the United States, blood storage procedures are subject to regulation by the government. The maximum storage periods for the blood components collected in these systems are specifically prescribed. For example, whole blood components collected in an "open" (i.e., non-sterile) system must, under governmental rules, be transfused within twenty-four hours and in most cases within six to eight hours. By contrast, when whole blood components are collected in a "closed" (i.e., sterile) system the red blood cells can be stored up to forty-two days (depending upon the type of anticoagulant and storage medium used) and plasma may be frozen and stored for even longer periods. Platelets can be frozen with dimethyl sulfoxide (DMSO) and stored for years (Valeri et al. (2000) Chapter 6, Frozen Platelets, pages 105–130, in Platelet Therapy: Current Status and Future Trends, Eds. Seghatchian, J. et al., Elsevier, Amsterdam). With 6% DMSO platelets can be stored for about three years at −80° C. and with 5% DMSO for about two years at −150° C.

While red cells are stored in the cold, Murphy and Gardner, New Eng. J. Med. 280:1094 (1969), demonstrated that platelets stored as platelet-rich plasma (PRP) at 22° C. possessed a better in vivo half-life than those stored at 4° C. Thus, more acceptable platelet concentrates could be transfused after storage at room temperature. Until recently, the rules allowed for platelet concentrate storage at room temperature for up to seven days (depending upon the type of storage container). However, it was recognized that the incidence of bacterial growth and subsequent transfusion reactions in the recipient increased to unacceptable levels with a seven-day-old platelet concentrate. Platelet concentrates may currently be stored for no more than five days.

Contamination of blood supplies with infectious microorganisms such as malaria, West Nile virus, HIV, hepatitis and other viruses and bacteria presents a serious health hazard for those who must receive transfusions of whole blood or administration of various blood components such as platelets, red cells, blood plasma, Factor VIII, plasminogen, fibronectin, anti-thrombin III, cryoprecipitate, human plasma protein fraction, albumin, immune serum globulin, prothrombin complex, plasma growth hormones, and other components isolated from blood. Blood screening procedures may miss contaminants, and sterilization procedures, which do not damage cellular blood components but effectively inactivate all or reduce infectious viruses and other microorganisms, are needed in the art. Systems that use the same chemistry to inactivate or reduce microorganisms in different fluids, for example separate blood components, are desired for many reasons, including ease of use in a blood bank setting. It is also desired that the inactivation or reduction treatment be easily implemented in a blood bank setting, and produce inactivation or reduction in a short period of time.

Bacteria can easily be introduced to blood components by at least two different means. First, if the donor is experiencing a mild bacteremia, a condition comprising bacteria in the blood, the blood will be contaminated, regardless of the collection or storage method. Adequate donor histories and physicals will decrease but not eliminate this problem. See B. J. Grossman et al., Transfusion 31:500 (1991).

A second, more pervasive source of contamination is the venepuncture employed when drawing blood. Even when "sterile" methods of skin preparation are employed, it is extremely difficult to sterilize the crypts around the sweat glands and hair follicles. During venepuncture, this contaminated skin is often cut out in a small "core" by a sharp needle. This core can serve to "seed" the blood bag with bacteria that may grow and become a risk to the recipient.

Indeed, many patients requiring platelet transfusions lack host-defense mechanisms for normal clearing and destruction of bacteria because of either chemotherapy or basic hematologic disease. The growth of even seemingly innocuous organisms in stored platelets can, upon transfusion, result in recipient reaction and death. See e.g., B. A. Myhre, JAMA 244:1333 (1980) and J. M. Heal et al., Transfusion 27:2 (1987).

It has been found that platelets which have been treated with a photosensitizer and light to inactivate or reduce pathogens which may be present may show re-activation of pathogens during long-term storage after such a treatment. In addition to platelet aggregation, platelets may show high activation and low extended shape change response by day 5 of storage, both of which may be indications of cytoskeletal changes in the platelets. Such changes may be indications of platelet damage due to the storage conditions. It is therefore necessary to improve the quality of stored photoradiated platelets.

There is a need for methods allowing for better pathogen reduction and/or inactivation while maintaining cell quality above acceptable limits and for methods allowing for improved cell quality while maintaining pathogen reduction and/or inactivation. Large quantities of blood and blood products are discarded by blood banks after certain periods of storage due to expiration of the blood and blood products. By improving the cell quality of blood components during storage and after pathogen reduction and/or inactivation, the shelf life blood components is increased.

In cells, food is oxidized to produce high-energy electrons that are converted to stored energy. This energy is stored in high-energy phosphate bonds in ATP. Ingested sugars are broken down by enzymes that split them into a six-carbon molecule called glucose. Glucose may also be provided to cells in media or storage solutions. The breakdown of glucose to provide energy to cells is an important mechanism in cellular metabolism. This mechanism, known as glycolysis, produces ATP (adenosine triphosphate) in the presence or absence of oxygen. The production of ATP is essential for cellular energy metabolism. Glucose enters the cell by special molecules in the membrane called "glucose transporters." Once inside the cell, glucose is broken down to make ATP in two pathways. The first pathway requires no oxygen and is called anaerobic metabolism. Anaerobic metabolism or glycolysis occurs in the cytoplasm outside the mitochondria. During glycolysis, glucose is broken down into pyruvate, a three-carbon molecule. This conversion involves a sequence of nine enzymatic steps that create phosphate-containing intermediates. Each reaction is designed to produce hydrogen ions (electrons) that can be used to make energy in the form of ATP. Only two ATP molecules can be made by one molecule of glucose run through this pathway. This pathway is also used to produce two lactate molecules from every one glucose molecule.

For most animal cells, glycolysis is merely the first stage in the breakdown of sugar into cellular energy, since the pyruvic acid that is formed at the last step quickly enters the cell's mitochondria to be completely oxidized to $CO_2$ and $H_2O$ in the citric acid cycle. The citric acid cycle is also known in the art as the Kreb's cycle or the tricarboxylic acid (TCA) cycle. The citric acid cycle occurs in the mitochondria and is the common pathway to completely oxidize fuel molecules, which are mostly acetyl CoA, the product from the oxidative decarboxylation of pyruvate. Acetyl CoA enters the cycle and passes through ten steps of reactions that yield energy (ATP) and $CO_2$.

In the case of organisms which are anaerobic (those that do not use molecular oxygen) and for tissues like skeletal muscle that can function under anaerobic conditions, glycolysis is a major source of the cell's ATP. This also occurs in an aerobic cell if the mitochondria of the cell are damaged in some way, thereby preventing the cell from entering the citric acid cycle.

Since ATP is essential to continued cell function, when aerobic metabolism is slowed or prevented by lack of oxygen, anaerobic pathways for producing ATP are stimulated and become critical for maintaining cell viability. Here, instead of being degraded in the mitochondria, the pyruvate molecules stay in the cytosol and can be converted into ethanol and $CO_2$ (as in yeast) or into lactate (as in muscle).

Lactate accumulation in cells causes an increased concentration of hydrogen ions and a decrease in pH. Blood cells in storage that experience a decrease in pH may be only undergoing glycolysis. Such a drop in pH indicates as well as contributes to a decrease in cell quality during cell storage.

Factors which cause cells to enter glycolysis and thereby accumulate lactic acid or lactate include events which occur internally in a body such as strokes or infarctions, as well as external events such as treatment of the cells after removal from a body. One example of an external treatment which might cause cells to accumulate lactate is a procedure to inactivate or reduce pathogens which might be contained in cells or fluids containing cells to be transfused into a recipient. Currently used methods to sterilize pathogenic contaminants which may be present in blood or blood components can cause damage to the mitochondria of the cells being treated. If this occurs, the cells can only make ATP through the glycolysis pathway, causing a buildup of lactic acid in the cell and a subsequent drop in pH during storage.

Mitochondria are critical subcellular organelles of blood components. They are involved in aerobic energy metabolism and the oxidative reactions therein. Mitochondria are sensitive to endogenous and exogenous influences and may be easily damaged or destroyed. Dysfunctional energy metabolism and, more severely, damaged mitochondria, lead to a decline in platelet quality and eventual cell death.

Possible causes of damage to blood components may be storage, pathogen inactivation, and pathogen reduction processes. A reason for changes in platelet viability after pathogen reduction or inactivation may be that irradiation of the platelets to kill pathogens may be causing damage to the platelet mitochondria (Chavez et al. (September 1998) Biochem. Mol. Biol. Int. 46(1):207–214; Masaki et al. (March 1997) J. Dermatol. Sci. 14(3):207–216; and Salet et al. (April 1995) Int. J. Radiat. Biol. 67(4):477–80). It has been observed that a side effect of a pathogen reduction process is that when platelets are subjected to UV light, the mitochondria of the platelets have a greater chance of suffering at least some damage than when they have been subjected to visible light. Mitochondria are present in all oxygen-utilizing organisms in which energy in the form of adenosine triphosphate (ATP) is generated and oxygen is reduced to water. Ninety percent of the oxygen taken in by the organism is consumed by the mitochondria. A substantial byproduct of ATP generation is the formation of potentially toxic oxygen radicals. For example, it is estimated that 1–2% of all reduced oxygen yields superoxide ($O_2$.) and hydrogen peroxide ($H_2O_2$). Other reactive oxygen species (ROS) that form are singlet oxygen ($O_2$) and hydroxyl radicals (.OH). Under stress conditions in the cell this can rise to 10% of all consumed oxygen. Mitochondrial membranes are sensitive to lipid peroxidation and depolarization resulting from these ROS.

Furthermore, photochemical methods for pathogen inactivation and reduction of blood products which generate singlet oxygen species in the process of photolysis of the photosensitizer cause further damage to mitochondrial membranes. It is therefore necessary to protect platelet mitochondria of platelets and other blood cells from ROS generated by both photochemical decontamination and stress conditions of storage.

There is a need in the art for methods to prevent damage to mitochondria, to reduce damage to and degradation of blood components during storage and before, during, and after pathogen inactivation and reduction procedures.

All references cited are incorporated herein by reference in their entirety to the extent that they are not inconsistent with the disclosure herein. Citation of the above documents is not intended as an admission that any of the foregoing is pertinent prior art. All statements as to the date or representation as to the contents of these documents is based on subjective characterization of the information available to the applicant, and does not constitute any admission as to the accuracy of the dates or contents of these documents.

SUMMARY OF THE INVENTION

This invention provides a method for treating a fluid comprising a cellular blood component to improve a vital quality of said cellular blood component, said method comprising adding an effective, substantially non-toxic amount of a mitochondrial enhancer to said fluid wherein said mitochondrial enhancer is selected from the group consisting of alloxazines, endogenous alloxazines, non-endogenous alloxazines, endogenously-based derivative alloxazines, endogenous photosensitizers, and non-endogenous photosensitizers. The concentration of mitochondrial enhancer in the fluid can be from any amount sufficient to provide measurable enhancement of a vital quality of a cell in the fluid up to a toxic amount. Preferably the mitochondrial enhancer is present at a final concentration from about one to about 200 micromolar.

This invention also provides methods for increasing the storage life of cellular blood components, extending platelet storage life, treating a cell comprising a mitochondrion, treating a fluid comprising cells containing mitochondria to improve a quality of said fluid, said methods comprising adding an effective, substantially non-toxic amount of a mitochondrial enhancer to said fluid wherein said mitochondrial enhancer is selected from the group consisting of alloxazines, endogenous alloxazines, non-endogenous alloxazines, endogenously-based derivative alloxazines, endogenous photosensitizers, and non-endogenous photosensitizers. Fluids treatable by the methods of this invention include fluids containing living cells with mitochondria or fluids that come into contact with living cells such as peritoneal solutions, blood, and fluids comprising a blood product. Cells treatable by the methods of this invention include plant cells, animal cells, yeast cells, cellular blood components, platelets, and cells in a wound surface.

In the practice of this invention, the fluid is optionally exposed to photoradiation greater than ambient light. When the fluid is exposed to photoradiation greater than ambient light, the photoradiation may be of sufficient energy to activate a photosensitizer in the fluid. When the fluid is exposed to photoradiation, the wavelength of the light can be in the visible or ultraviolet spectrum. When the fluid is exposed to photoradiation, it can be performed at a time selected from the group consisting of before, after, and simultaneously with treating the fluid with mitochondrial enhancer. When the fluid is exposed to photoradiation, it can be of energy between about 5 J/cm² and about 150 J/cm².

When the fluid is exposed to photoradiation of sufficient energy to activate a photosensitizer which is also in the fluid, the photoradiation can also be of sufficient energy to substantially reduce pathogens which may be present in the fluid. Pathogens which can be reduced by the methods of this invention include extracellular and intracellular viruses, bacteria, bacteriophages, fungi, blood-transmitted parasites, and protozoa, and mixtures of any two or more of the foregoing.

When photosensitizer is added to the fluid, the photosensitizer can be the same as the mitochondrial enhancer that is added to the fluid. The concentration of photosensitizer can be any amount sufficient to provide a measurable reduction of pathogens in the fluid up to an amount which would be toxic to the cells. Preferably the photosensitizer is present at a concentration from about 1 to about 200 micromolar. In one embodiment of this invention, the cellular blood component is not stored prior to said treating. In another embodiment of this invention, the cellular blood component is stored prior to said treating. When the cellular blood component is stored prior to treating, it is stored for an amount of time between about 1 hour and about 7 days prior to said treating. Alternatively the cellular blood component is stored for more than about one hour prior to said treating.

Mitochondrial enhancers useful in the practice of this invention, which may simultaneously act as photosensitizers, include 7,8-dimethyl-10-ribityl isoalloxazine, 7,8-dimethylalloxazine, 7,8,10-trimethylisoalloxazine, alloxazine mononucleotide, isoalloxazine-adenosine dinucleotide, vitamin K1, vitamin K1 oxide, vitamin K2, vitamin K5, vitamin K6, vitamin K7, vitamin K-S(II), and vitamin L. When the mitochondrial enhancer is 7,8-dimethyl-10-ribityl isoalloxazine it is in the fluid at a concentration of about one to about 200 micromolar.

Additional mitochondrial enhancers useful in the practice of this invention include molecules of the formula:

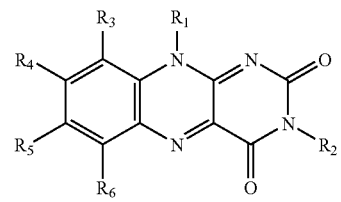

wherein R1, R2, R3, R4, R5 and R6 are, independently from one another, selected from the group consisting of hydrogen, optionally substituted hydrocarbyl, alcohol, amine, polyamine, sulfate, phosphate, halogen selected from the group consisting of chlorine, bromine and iodine, salts of the foregoing; and $-NR^a-(CR^bR^c)_n-X$ wherein X is a halogen selected from the group consisting of chlorine, bromine and iodine, $R^a$, $R^b$ and $R^c$ are, independently of each other, selected from the group consisting of hydrogen, optionally substituted hydrocarbyl, and halogen selected from the group consisting of chlorine, bromine and iodine, and n is an integer from 0 to 20; provided that R1 is not —OH or a straight chain alkyl group where the second carbon of the chain is substituted with —OH or =O and R1, R4, R5 are not all methyl groups when R2, R3 and R6 are hydrogen. R1, R2, R3, R4, R5 and R6 can be, independently from one another, selected from the group consisting of hydrogen, optionally substituted alcohol, straight chain or cyclic saccharide, amino acid, amine, polyamine, polyether, polyalcohol, sulfate, phosphate, carbonyl, glycol, halogen selected from the group consisting of chlorine, bromine and iodine, aldehyde, ketone, carboxylic acid and ascorbate. These compounds may also act as photosensitizers.

An example of a cellular blood component treatable by the methods of this invention is platelets. In an embodiment of this invention, the cellular blood component is stored for more than about one hour after said mitochondrial enhancer is added.

The methods of this invention can also include adding nitric oxide to the fluid, adding quencher to the fluid, adding process enhancer to the fluid, adding oxygen to the fluid, and/or adding glycolysis inhibitor to the fluid.

Vital qualities that are improved by the methods of this invention include oxygen consumption, rate of oxygen consumption, lactate production, rate of lactate production, pH, rate of pH change, activation, hypotonic shock response, glucose consumption, rate of glucose consumption, platelet swirl, platelet aggregation, carbon dioxide production, rate of carbon dioxide production, cell count, and extent of shape change.

In an embodiment of this invention, the oxygen consumption is increased by at least about 5%. In an embodiment of this invention, the rate of lactate production is decreased by at least about 25%. In an embodiment of this invention, the pH is increased by at least about 0.1 units. In an embodiment of this invention, the hypotonic shock response is increased by at least about 5%. In an embodiment of this invention, the glucose consumption is decreased by at least about 10%. In an embodiment of this invention, the platelet swirl is increased by at least about 5%. In an embodiment of this invention, the platelet aggregation is decreased by at least about 5%. In an embodiment of this invention, the carbon dioxide production is increased by at least about 5%. In an embodiment of this invention, the cell count is increased by at least about 5%. In an embodiment of this invention, the extent of shape change is increased by at least about 5%. In an embodiment of this invention, the activation is decreased by at least about 5%.

DETAILED DESCRIPTION OF THE INVENTION

Definitions

Figure 1:
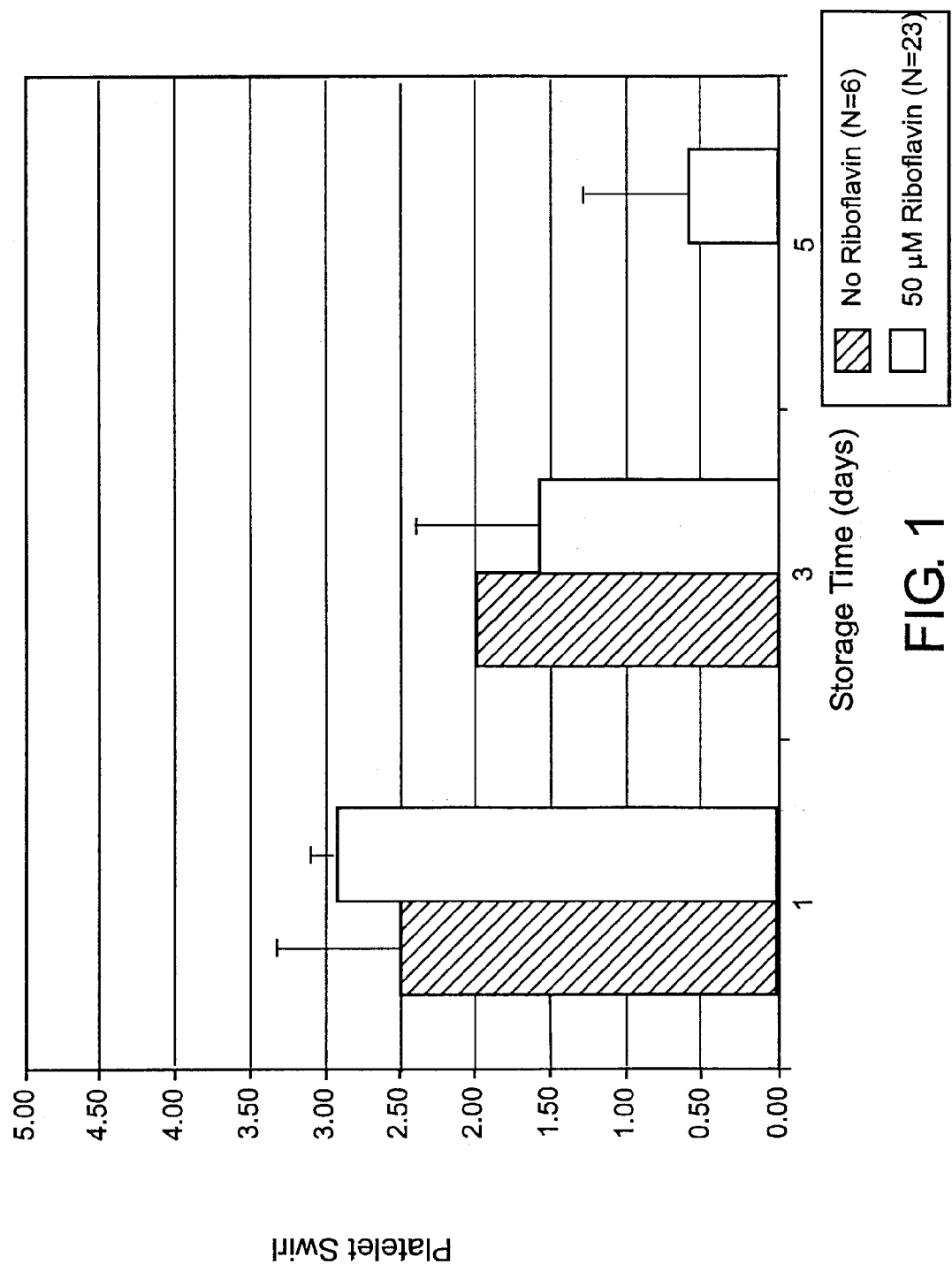
FIG. 1 is a graph showing the effect of mitochondrial enhancer on platelet swirl (0–4 units) of cellular blood components as a function of storage time (days).

As used herein, "mitochondrial enhancer" refers to a composition which enhances a vital quality of mitochondria or of cells containing mitochondria. Mitochondrial enhancers useful in the practice of this invention include, but are not limited to alloxazines, endogenous alloxazines, non-endogenous alloxazines, endogenously based derivative alloxazines, endogenous photosensitizers, and non-endogenous photosensitizers.

As used herein, "ambient light" refers to natural light such as sunlight, including sunlight through glass or plastic, or overhead room light, such as from incandescent, fluorescent, and/or halogen bulbs. Ambient light is generally not of enough energy and/or of the appropriate wavelengths to sufficiently activate a photosensitizer in a solution to substantially reduce pathogens therein.

As used herein, "substantially inactivate pathogens" refers to reducing the ability of pathogens to reproduce, preferably by killing them. When the treated fluid comprises a cellular blood component, the level of pathogens in the fluid can be decreased such that the cellular blood component may be safely administered to a patient.

As used herein, "substantially reduce pathogens" refers to reducing the ability of pathogens to reproduce, preferably by killing them. When the treated fluid comprises a cellular blood component, the level of pathogens in the fluid can be decreased such that the cellular blood component may be safely administered to a patient.

As used herein, "storage" refers to the amount of time after formulation or collection before a fluid is utilized for its intended purpose. As used herein, storage of blood or blood product refers to time between the collection of the blood or blood product and the utilization of the blood or blood product for its intended purpose, such as the administration of that blood product to a patient.

As used herein, "an amount of mitochondrial enhancer sufficient to improve storage life" refers to an amount that measurably increases a vital cell quality.

As used herein, "glycolysis inhibitor" refers to compositions that interfere with the biochemical pathway of glycolysis. 2-deoxy-D-glucose is an example of a glycolysis inhibitor.

As used herein, "adding nitric oxide to a fluid" refers to increasing the amount of nitric oxide within a fluid. In the practice of this invention nitric oxide may be added to a fluid by any method known in the art. Methods for adding nitric oxide to a fluid include, but are not limited to, adding liquids, solids, or gases containing nitric oxide and adding nitric oxide generators. Nitric oxide generators are chemicals that are able to react, directly or indirectly, to produce nitric oxide. Nitric oxide generators may react with components already in a fluid to produce nitric oxide, or they may require the addition of one or more different nitric oxide generators to the fluid, with which they may react to produce nitric oxide. Nitric oxide generators that do not require the addition of one or more different nitric oxide generators are nitric oxide donors. Nitric oxide donors are well known in the art (Bauer et al., (1995) Advances in Pharmacology 34:361 and U.S. Pat. No. 6,232,434) and are available for purchase from companies such as Cayman Chemical, Ann Arbor, Mich. Nitric oxide donors include, but are not limited to L-arginine, N-acetyl-L-cysteine, DEA-NO, DETA-NO, DETA-NONOate, PAPA-NO, sodium nitroprusside, and nitroglycerine. Liquids containing nitric oxide include, but are not limited to liquids comprising two nitric oxide generators combined in a fluid to produce nitric oxide, saline in which nitric oxide gas has been bubbled, and nitric oxide-saturated water.

As used herein, "adding oxygen" refers to adding oxygen to a fluid to increase the dissolved oxygen in the fluid to an amount greater than would be present in the fluid when the fluid is under an air atmosphere at ambient conditions without mixing.

As used herein, "process enhancer" refers to a composition that enhances a pathogen reduction process. Process enhancers can be included in photoradiation processes of this invention. Such enhancers include antioxidants or other agents to prevent damage to desired fluid components or to improve the rate of reduction of microorganisms and are exemplified by adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, trolox, glycerol, vitamin E, alpha tocopherol acetate, and mixtures thereof. These process enhancers may be added in dried medium form (including powder or pill) or in the form of liquids.

As used herein, "agitator" refers to an apparatus which can agitate, e.g. shake or rotate, the container containing the product to be irradiated, such as the Helmer platelet incubator/agitator (Helmer Company, Noblesville, Ind.).

As used herein with respect to platelet compositions, "100% plasma carryover" and "100% PCO" refer to plasma to which about 20% by volume of anticoagulant has been added. 100% PCO is therefore about 80% plasma. By a similar calculation, 90% PCO is about 72% plasma. The balance of the platelet composition which is neither plasma nor anticoagulant can contain additional ingredients such as mitochondrial enhancer and/or photosensitizer. Anticoagulants known to the art are useful in the practice of this invention, including ACD-A (anticoagulant citrate dextrose formula A) and CPD (citrate phosphate dextrose).

As used herein, "vital quality" refers to an indicator of cellular blood component quality, i.e., a parameter of a fluid containing cells or a cellular blood component that can be measured to assess its quality. Indicators of cellular blood component quality (vital qualities) are described below and include but are not limited to activation, hypotonic shock response, amount and rate of lactate production, amount and rate of glucose consumption, pH and rate of pH change, platelet swirl, platelet aggregation, amount and rate of oxygen consumption, amount and rate of carbon dioxide production, cell count (cell survival), and extent of shape change (ESC). As used herein, to "improve a vital quality of a cellular blood component" refers to improving a parameter of a cellular blood component that can be measured to assess quality, including the previously mentioned parameters. An improved cellular blood component provides better results when utilized, for example, to treat patients. Measurement of these vital qualities provides information on the status of mitochondria health. Additional qualities which provide information on the status of mitochondria health include activation, hypotonic shock response, glucose consumption, platelet swirl, platelet aggregation, carbon dioxide production, cell count, and ESC.

As used herein, "amount of mitochondrial enhancer effective to improve a vital quality" refers to enough mitochondrial enhancer to cause a measurable improvement in a vital cell quality, but not so much as to be toxic to cells containing mitochondria. When the mitochondrial enhancer is naturally present in the cell or its environment, the mitochondrial enhancer of this invention is added in an amount sufficient to cause a measurable improvement in a vital quality. When the mitochondrial enhancer riboflavin is added to blood cells, between about 0.1 micromolar and about 1 millimolar, between about 1 micromolar and about 200 micromolar, and between about 5 micromolar and about 75 micromolar final concentrations are effective.

The term "biologically active" means capable of effecting a change in a living organism or component thereof.

The terms "blood product" and "blood component" as used herein include blood, plasma, blood constituents, and therapeutic protein compositions containing proteins derived from blood.

As used herein, "cellular blood component" refers to blood components that contain a substantial amount of or are cellular components of blood. Cellular blood components include platelets, erythrocytes (red blood cells), eosinophils, neutrophils, leukocytes (white blood cells), monocytes, lymphocytes, basophils, and blood stem cells. If a sample of plasma contains a substantial amount a cellular blood component, i.e. enough so that the cells therein are useful, such as platelets or white blood cells, it is a cellular blood component. As used herein, a "blood component comprising platelets" includes platelets in plasma and platelets in media.

As used herein, "cells in a wound surface" refers to cells at or near the surface of a wound. Wounds towards the surface of a mammalian body can include white blood cells, red blood cells, fibroblasts, epidermal cells, and endothelial cells. Cells in a wound surface can include cells of ectodermal, mesodermal, and endodermal origin. "Substantially non-toxic" amounts of elements of this invention are those which do not destroy the biological activity of such fluid components other than microorganisms.

As used herein, "pathogen" refers to an individual pathogenic organism of one species, a plurality of such organisms of one species, or a plurality of pathogenic organisms of two or more species. As used herein, "increase pathogen inactivation" with respect to the effects of a procedure described herein refers to reduction of a greater quantity of pathogens after using the procedure than in the absence of the procedure. As used herein, "increase pathogen reduction" with respect to the effects of a procedure described herein refers to reduction of a greater quantity of pathogens after using the procedure than in the absence of the procedure.

The pathogens which may be present in fluid and decontaminated by the processes of this invention typically include those selected from the group consisting of extracellular and intracellular viruses, bacteria, bacteriophages, fungi, blood-transmitted parasites, and protozoa, and mixtures of any two or more of the foregoing. If one of the pathogens is a virus, it may be selected from the group consisting of human immunodeficiency virus (HIV), hepatitis A, B and C viruses, sindbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, and Epstein-Barr virus, bovine viral diarrhea virus, pseudorabies, West Nile virus, and mixtures of any two or more of the foregoing. If one of the pathogens is a bacteriophage, it may be selected from the group consisting of ΦX174, Φ6, λ, R17, T4, and T2, and mixtures of any two or more of the foregoing. If one of the pathogens is a bacterium, it may be selected from the group consisting of *P. aeruginosa, S. aureus, S. epidermidis, E. coli, K. pneumoniae, E. faecalis, B. subtilis, S. pneumoniae, S. pyrogenes, S. viridans, B. cereus, E. aerogenes, propionabacter, C. perfringes, E. cloacae, P. mirabilis, S. cholerasuis, S. liquifaciens, S. mitis, Y. entercolitica, P. fluorescens, S. enteritidis, C. freundii,* and *S. marcescens,* and mixtures of any two or more of the foregoing. In an embodiment of this invention, if one of the pathogens is a protozoon, it may be *P. falciparum*.

As used herein "photosensitizer" refers to any compound which absorbs radiation of one or more defined wavelengths and subsequently utilizes the absorbed energy to carry out a chemical process. The photosensitizers useful in this invention include any photosensitizers known to the art to be useful for reducing microorganisms. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones. Photosensitizers of this invention may include compounds which preferentially adsorb to nucleic acids, thus focusing their photodynamic effect upon microorganisms and viruses with little or no effect upon accompanying cells or proteins. Other photosensitizers of this invention are also useful, such as those using singlet oxygen-dependent mechanisms. Photosensitizers useful in the practice of this invention include endogenous photosensitizers.

As used herein, "activate a photosensitizer" refers to altering a photosensitizer to make it capable of substantially reducing pathogens. An activated photosensitizer is capable of reducing microorganisms in a fluid, such as by interfering to prevent their replication. Specificity of action of the photosensitizer can be conferred by the close proximity of the photosensitizer to nucleic acid of the microorganism and this may result from binding of the photosensitizer to the nucleic acid. "Nucleic acid" includes ribonucleic acid (RNA) and deoxyribonucleic acid (DNA). Photosensitizers can also act by binding to cell membranes or by other mechanisms.

The term "endogenous" means naturally found in a human or mammalian body, either as a result of synthesis by the body or because of ingestion as an essential foodstuff (e.g. vitamins) or formation of metabolites and/or byproducts in vivo. The term "non-endogenous" means not naturally found in a human or mammalian body, either as a result of synthesis by the body or because of ingestion of an essential foodstuff or formation of metabolites and/or byproducts in vivo.

Examples of endogenous photosensitizers include alloxazines. Alloxazines are molecules comprising an alloxazine backbone. The term "alloxazine" includes isoalloxazines. Examples of endogenous photosensitizers include 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. Endogenously based derivative photosensitizers include synthetically derived analogs and homologs of endogenous photosensitizers which may have or lack lower (1–5) alkyl or halogen substituents of the photosensitizers from which they are derived, and which preserve the function and substantial non-toxicity thereof. When endogenous photosensitizers or endogenously based derivative photosensitizers are used in the practice of this invention, particularly when such photosensitizers are not inherently toxic or do not yield toxic photoproducts after photoradiation, no removal or purification step is required after decontamination, and treated product can be directly returned to a patient's body or administered to a patient in need of its therapeutic effect.

Non-endogenous photosensitizers that are mitochondrial enhancers and are based on endogenous structures, such as those described in U.S. patent application Ser. No. 09/420,652 are useful in the practice of this invention. These non-endogenous mitochondrial enhancers and endogenously based derivative mitochondrial enhancers are referred to herein as endogenously based derivative mitochondrial enhancers. The include molecules of the formula:

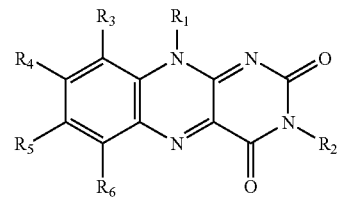

wherein R1, R2, R3, R4, R5 and R6 are, independently from one another, selected from the group consisting of hydrogen, optionally substituted hydrocarbyl, alcohol, amine, polyamine, sulfate, phosphate, halogen selected from the group consisting of chlorine, bromine and iodine, salts of the foregoing, and $-NR^a-(CR^bR^c)_n-X$ wherein X is a halogen selected from the group consisting of chlorine, bromine and iodine, $R^a$, $R^b$ and $R^c$ are, independently of each other, selected from the group consisting of hydrogen, optionally substituted hydrocarbyl, and halogen selected from the group consisting of chlorine, bromine and iodine, and n is an integer from 0 to 20; provided that R1 is not —OH or a straight chain alkyl group where the second carbon of the chain is substituted with —OH or =O and R1, R4 and R5 are not all methyl groups when R2, R3 and R6 are all hydrogen.

In one group of compounds, n is an integer between 0 and 5. In another group of compounds, n is an integer from 0 to 10. In another group of compounds, n is an integer from 0 to 20.

In another group of compounds, R1 is not —OH or a straight chain alkyl group where the second carbon of the chain is substituted with —OH or =O; and R1 is not a 2-, 3-, 4- or 5-carbon straight chain alkyl that terminates in —OH, —COH, or —H when R2, R3 and R6 are H, and R4 and R5 are CH$_3$; R1 is not —CH$_2$CH$_2$—(CHOH)$_2$—CH$_3$ or —CH$_2$CH$_2$—(CHOH)$_2$—CH$_2$SO$_4$ or 1'-D-sorbityl or 1'-D-dulcityl or 1'-D-rhamnityl or 1'-D,L-glyceryl or —CH$_2$—O—C(O)—CH$_3$ or —CH$_2$—O—C(O)—CH$_2$CH$_3$ or 2', 3', 4', 5'-di-O-isopropyridene-riboflavin or 8-aminooctyl when R2, R3 and R6 are H and R4 and R5 are CH$_3$; R1 is not 1'-D-sorbityl or 1'-D-dulcityl when R4 and R5 are both chlorines and when R2, R3 and R6 are all hydrogens; R5 is not ethyl or chloro when R1 and R4 are methyl and R2, R3 and R6 are all hydrogens; R4 and R5 are not both methoxy or both tetramethylene when R1 is methyl and R2, R3 and R6 are all hydrogens; R2 is not —CH$_2$CH$_2$NH when R1, R4 and R5 are CH$_3$ and R3 and R6 are H; R2 is not

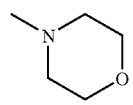

when R1, R4 and R5 are CH$_3$ and R3 and R6 are H; R5 is not chloro when R4 is methoxy and R1 is ethyl-2'N-pyrrolidino and R2, R3, and R6 are hydrogen; R1 is not N,N-dimethylaminopropyl or N,N-diethylaminoethyl when R5 is chloro or methyl and R2, R3, R4 and R6 are hydrogen; R3 is not —NH(CH$_2$CH$_2$)Cl when R6 is —NH$_2$ and R1, R2, R4 and R5 are H; R1, R4, R5 are not all methyl groups when all of R2, R3 and R6 are hydrogens; R1, R4, R5 and R2 are not all methyl groups when R3 and R6 are hydrogens; R2 is not carboxymethyl when R1, R4 and R5 are methyl and R3 and R6 are hydrogen; R4 is not —NH$_2$ when R1 and R5 are methyl and R2, R3 and R6 are all hydrogen; R1 is not a phenyl group when R4 and R5 are methyl and R2, R3 and R6 are all H; R1 is not methyl or N,N-dimethylaminoethyl when all of R2, R3, R4, R5 and R6 are hydrogens; R2, R4, R5 are not all methyl when R1 is acetoxyethyl and R3 and R are hydrogen; R5 is not methyl when R1 is N,N-diethylaminoethyl and R2, R3, R4 and R6 are all hydrogen; R4 and R5 are not both chlorine when R1 is methyl and R2, R3 and R6 are all hydrogen; R1 is not ethyl, β-chloroethyl, n-butyl, anilino, benzyl, phenyl, p-tolyl or p-anisyl when R5 is NH$_2$ and R2, R3, R4 and R6 are all hydrogen; and R4 is not chlorine when R1 is N,N-dimethylaminopropyl and R2, R3, R5 and R6 are all hydrogen.

Compounds containing any combination of substituents or members of the Markush groups specified above are useful in the practice of this invention. All compounds useful in the practice of this invention have the ability to enhance mitochondrial function. All substituents of the compounds of the invention may be the same, all substituents may be different, or any combination of substituents may be the same or different. Substituents with a specified function, for example those that impart water solubility to the compound, may be included at any of R1–26.

Compounds useful in the practice of this invention include all those compounds with the isoalloxazine backbone (shown below):

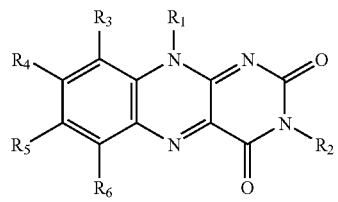

where R1–R6 are substituted with various substituents, as described elsewhere, except those previously known to the art. The substituents included in the compounds and used in the methods of the invention may be any substituent not having structures or reactivity which would substantially interfere with the desired microorganism neutralization of the microorganism neutralizer, as may readily be determined without undue experimentation by those skilled in the art. The foregoing isoalloxazine-related photosensitizers also function as enhancers of mitochondrial function.

This invention provides methods for treating cell-containing fluids to improve a vital quality of the fluid by enhancing the vital quality and/or preventing damage to mitochondria within the cells. Compositions useful for treating fluids to enhance mitochondrial function and/or prevent damage to mitochondria comprise mitochondrial enhancers. Mitochondrial enhancers provided by this invention include alloxazines such as endogenous alloxazines, non-endogenous alloxazines, and endogenously based derivative alloxazines, and photosensitizers such as endogenous photosensitizers, non-endogenous photosensitizers, and endogenously based derivative photosensitizers. Molecules with alloxazine backbones are alloxazines. The methods provided by this invention comprise adding a substantially non-toxic amount of mitochondrial enhancer to a fluid, whereby the function of a mitochondrion within a cell in the fluid is enhanced. Mitochondria are enhanced when they are prevented from being damaged, when they are rejuvenated, and/or when a vital cell quality of a cell containing mitochondria is improved. When a method step is performed on the fluid which damages mitochondria within cells in the fluid, such as storing or photoradiating to reduce pathogens which may be present within the fluid, the mitochondrial enhancer prevents damage to or rejuvenates mitochondria within the cells. Mitochondrial enhancer may be added before, during, or after the damaging method step. The methods of this invention include the use of mitochondrial enhancer to prevent damage to and/or rejuvenate non-lymphocytic blood components before, during, and after a lymphocytic population reduction process.

Any fluid comprising a cell containing a mitochondrion is treatable by the methods of this invention. Mitochondrial enhancer is used in an amount which is effective at preventing damage to and/or rejuvenating mitochondria and which is also non-toxic to the mitochondria, to the cells containing the mitochondria, and to the recipient of the treated fluid. Fluids treatable by the methods of this invention include blood, fluids comprising a cellular blood product or a cellular blood component, and bodily fluids. Cellular blood components treatable by the methods of this invention include platelets, blood, and plasma containing platelets or other cellular blood components. When the fluid to be treated by the methods of this invention is to be consumed by a human or an animal, the mitochondrial enhancer must also be non-toxic to the human or animal, or be removed from the fluid before consumption. This invention also provides methods for using mitochondrial enhancer to treat cells having mitochondria. Cells treatable by the methods of this invention include cells known in the art to contain mitochondria, including plant cells, animal cells, and yeast cells. This invention also provides methods for using mitochondrial enhancer to treat a wound surface. Cells at or near a wound surface can include white blood cells, red blood cells, fibroblasts, epidermal cells, and endothelial cells. Cells in a wound surface can include cells of ectodermal, mesodermal, and endodermal origin. Treating mitochondria-containing cells in a wound surface with mitochondrial enhancer improves the health of the cells, prevents infection, and speeds healing.

Any fluid that will be in contact with a cell containing a mitochondrion (e.g. peritoneal fluid and saliva) is treatable by the methods of this invention. Peritoneal fluid is the fluid within the peritoneal space that houses the gastrointestinal organs of the mammalian body. Peritoneal fluid can contain cells and can be treated by the methods of this invention. Additionally, peritoneal fluid can be removed from a body, mitochondrial enhancer added, and the treated fluid administered back to a body. Alternatively mitochondrial enhancer can be directly administered to peritoneal fluid inside a body, without removing peritoneal fluid. The mitochondrial enhancer in the peritoneal fluid inside the body enhances the mitochondrial function of cells within the fluid and/or lining the peritoneal space. Adding mitochondrial enhancer to saliva enhances the mitochondrial function of cells lining the digestive tract.

When blood or blood components are collected from an individual and the blood or blood components are to be transfused into the same or another individual, the processes of collection and transfusion, the passage of time between collection and transfusion, and processes performed on blood and blood components between collection and transfusion may decrease the quality of the blood or the blood components. Change in the quality of blood or blood component is detectable as a change in a vital quality of the blood or blood component and can be assayed by any method known to the art. Indicators of cellular blood component quality (vital qualities) include but are not limited to activation, hypotonic shock response, amount and rate of lactate production, amount and rate of glucose consumption, pH and rate of pH change, platelet swirl, platelet aggregation, amount and rate of oxygen consumption, amount and rate of carbon dioxide production, cell count, and extent of shape change (ESC).

The processes of collection and transfusion, the passage of time between collection and transfusion, and processes performed on blood and blood components between collection and transfusion may decrease the quality of blood or cellular blood components by damaging mitochondria or mitochondrial processes that occur within the blood or cellular blood components. As previously described, when mitochondria or mitochondrial processes are damaged, the energy-producing metabolism of a cell switches to favor anaerobic glycolysis over oxidative phosphorylation in combination with the citric acid cycle and electron transport chain process, which occurs within the mitochondria, optionally in combination with glycolysis in the cytoplasm. As a result, less oxygen is consumed by the fluid comprising the blood or blood product, lactate production is increased (lactate is a product of glycolysis), and the resulting increase in lactic acid causes a decrease in the pH of the fluid. Therefore, indicators of cell quality that are also indicators of mitochondrial health include amount and rate of oxygen consumption, amount and rate of lactate production, pH and rate of pH change. Other indicators of cell quality, including, but not limited to, activation, hypotonic shock response, amount, and rate of glucose consumption, platelet swirl, platelet aggregation, amount and rate of carbon dioxide production, cell count, and ESC, also provide information on mitochondrial health.

Processes that can decrease the quality of blood or cellular blood components include, but are not limited to, the passage of time between collection and transfusion and photoradiation to reduce pathogens. The passage of time between collection and transfusion, or other use for collected blood or blood product, may be as short as a few minutes to a few hours, to days, or as long as several weeks. As described above, whole blood components collected in an "open" (i.e., non-sterile) system must, under governmental rules, be transfused within twenty-four hours and in most cases within six to eight hours. When whole blood components are collected in a "closed" (i.e., sterile) system, the red blood cells can be stored up to forty-two days (depending upon the type of anticoagulant and storage medium used), and plasma may be frozen and stored for even longer periods. Currently, platelet concentrate may be stored at room temperature for up to no more than five days.

This invention provides a method for treating a fluid comprising a cellular blood component to improve a vital quality of said blood component, said method comprising adding a substantially non-toxic amount of a mitochondrial enhancer to said fluid wherein said mitochondrial enhancer is selected from the group consisting of endogenous alloxazines, non-endogenous alloxazines, endogenously-based derivative alloxazines, photosensitizers, endogenous photosensitizers, non-endogenous photosensitizers, and endogenously-based derivative photosensitizers. In one embodiment of this invention, the fluid is not exposed, before, after, or during addition of a mitochondrial enhancer, to photoradiation greater than ambient light. Adding mitochondrial enhancer to a fluid comprising blood or a cellular blood component improves the quality of the blood or cellular blood component thereby increasing the allowed storage life of the blood or cellular blood component, allowing the blood or cellular blood component to be stored for a longer amount of time before it is administered to a patient. The FDA provides Guidance for Industry: An Acceptable Circular of Information for the Use of Human Blood and Blood Components, which may be found on the fda.gov website at /cber/gdlns/circbld.pdf and allowed storage times of blood and blood components are known in the art. In one embodiment of this invention involving platelets, the vital cell qualities of platelets treated with mitochondrial enhancer are improved such that the treated platelets can be administered to a patient after seven days of storage.

Mitochondrial enhancer may be added to a fluid before, after, and/or during storage. In the practice of this invention, if a fluid is utilized for its intended purpose immediately after creation or acquisition, it is considered to have not been stored. If time passes between creation or acquisition, including processing time, this is storage time. In one embodiment of this invention, mitochondrial enhancer is added at the beginning of storage. The beginning of storage is about the first 10% of total storage time. In another embodiment mitochondrial enhancer is added during the middle of storage. The middle of storage is about the central 80% of total storage time. In another embodiment, mitochondrial enhancer is added towards the end of storage. The end of storage is about the last 10% of total storage time. In an embodiment of this invention, a fluid comprising blood or a cellular blood component has been stored for an amount of time between about one minute and about forty-five days before adding mitochondrial enhancer. In an embodiment of this invention, a fluid comprising blood or a cellular blood component has been stored for an amount of time between about one hour and about seven days before adding mitochondrial enhancer. In an embodiment of this invention, the fluid comprises platelets that have been stored for six days before mitochondrial enhancer is added to the fluid. In an embodiment of this invention, a fluid comprising blood or a cellular blood component is stored for an amount of time between about one hour and about five days after adding mitochondrial enhancer. In another embodiment of this invention, a fluid comprising blood or a cellular blood component is stored for an amount of time between about one minute and about forty-five days before adding mitochondrial enhancer, and the fluid to which mitochondrial enhancer had been added is subsequently stored for an amount of time between about one minute and about forty-five days. In another embodiment of this invention, a fluid comprising platelets is stored for an amount of time up to about three years after adding mitochondrial enhancer. In yet another embodiment of this invention, a fluid comprising a cellular blood component is stored for an amount of time up to about three years before adding mitochondrial enhancer.

Additional methods steps may be performed on a fluid in the practice of this invention. In one embodiment of this invention, the method also comprises exposing the fluid to photoradiation of energy greater than ambient light. In one embodiment, the method also comprises performing a pathogen reduction process on the fluid. In one embodiment of this invention, the pathogen reduction process comprises exposing the fluid to photoradiation of sufficient energy to substantially reduce pathogens which may be present in the fluid. In one embodiment, a pathogen reduction process is performed before adding mitochondrial enhancer to the fluid. In another embodiment, mitochondrial enhancer is added during a pathogen reduction process. In another embodiment a pathogen reduction process is performed after adding mitochondrial enhancer. In one embodiment, mitochondrial enhancer is added during a pathogen reduction process, resulting in a pathogen reduction process being performed before, during, and after adding mitochondrial enhancer. As known in the art, pathogen reduction processes utilizing photoradiation also typically utilize a photosensitizer. In one embodiment of this invention, the method also comprises adding a photosensitizer to the fluid. A mitochondrial enhancer may also be a photosensitizer and vice versa. In one embodiment of this invention, the photosensitizer is the same as the mitochondrial enhancer utilized. In one embodiment, the step of adding photosensitizer to the fluid is performed by adding mitochondrial enhancer to the fluid. Pathogens that are substantially reduced by the methods of this invention include extracellular and intracellular viruses, bacteria, bacteriophages, fungi, blood-transmitted parasites, protozoa, and mixtures of any two or more of the foregoing.

When performing a pathogen reduction process utilizing photoradiation on a fluid, an amount of photoradiation is chosen that substantially reduces pathogens without destroying desired biological activities within the fluid. Preferably an amount of photoradiation is chosen that minimally damages or decreases desired biological activities within the fluid. In an embodiment of this invention, visible photoradiation is of about 419 nM. In an embodiment of this invention, ultraviolet radiation is of about 320 nM. This invention provides methods for adding mitochondrial enhancer to a fluid, wherein addition of mitochondrial enhancer protects or rejuvenates fluid components from damage caused by photoradiation steps of a pathogen reduction process performed on the fluid, enabling the use of more photoradiation energy which in turn enables better pathogen reduction. In an embodiment of this invention, mitochondrial enhancer is added to a fluid comprising platelets before a pathogen reduction process utilizing between about 5 $J/cm^2$ and about 360 $J/cm^2$ ultraviolet photoradiation is performed on the fluid. In another embodiment of this invention, the pathogen reduction process utilizes more than about 5 $J/cm^2$, more than about 30 $J/cm^2$, more than about 50 $J/cm^2$, more than about 80 $J/cm^2$, more than about 100 $J/cm^2$, more than about 120 $J/cm^2$, more than 120 $J/cm^2$, more than about 180 $J/cm^2$, more than 180 $J/cm^2$, more than 200 $J/cm^2$, between about 5 $J/cm^2$ and about 360 $J/cm^2$, between about 25 $J/cm^2$ and about 180 $J/cm^2$, between about 75 $J/cm^2$ and about 120 $J/cm^2$, or between about 120 $J/cm^2$ and about 180 $J/cm^2$ ultraviolet radiation.

In one embodiment of this invention, more than one mitochondrial enhancer is added. In one embodiment, mitochondrial enhancer is added more than once.

In one embodiment of this invention, the mitochondrial enhancer is riboflavin, also known as 7,8-dimethyl-10-ribityl isoalloxazine. In one embodiment, riboflavin is added to a final concentration in the fluid of about 1 micromolar to about 200 micromolar. In one embodiment about ten micromolar is added. In another embodiment about 50 micromolar is added. Riboflavin can be a photosensitizer and a mitochondrial enhancer. In one embodiment, riboflavin is added in an amount between about five micromolar and about 100 micromolar.

In the practice of this invention, at least one vital quality of the fluid being treated, e.g. a fluid comprising blood or cellular blood component, is improved after adding mitochondrial enhancer to the fluid. Any indicator of cell quality known in the art may be measured. During cell metabolism, cells consume glucose and make two lactate molecules, which lowers the pH. In the U.S. the specified lower limit for pH of the surrounding fluid is about 6.2 as measured at 22° C. Limits can be different in different countries. A fixed amount of glucose is provided to cells in storage. If the cells use up the glucose too quickly, they will die. A slower consumption of glucose is better, resulting in less lactose production and maintenance of a pH above 6.2. Glucose consumption, lactose production, and pH indicators of cell quality are measured in rate as well as absolute change. Three activity parameters that can be measured to determine whether platelets and other cellular blood components have retained their functional ability after storage are: cell count, hypotonic stress response, and aggregation, as induced by collagen in combination with adenosine diphosphate (ADP). In an embodiment of this invention, indicators of cell quality measured in the practice of this invention include activation, hypotonic shock response, amount and rate of lactate production, amount and rate of glucose consumption, pH, rate of pH change, platelet swirl, platelet aggregation, amount and rate of oxygen consumption, amount and rate of carbon dioxide production, cell count, and/or ESC. Indicators of cell quality are typically measured periodically, e.g., cell quality for platelets is typically measured each hour or on Days 1, 3, 5, and/or 7 after adding mitochondrial enhancer. All methods known in the art for measuring indicators of cell quality are useful in the practice of this invention. Oxygen concentration, carbon dioxide concentration, and pH may be measured using a blood gas analyzer.

P-selectin, also known as GMP-140, measures activation. When cells are activated, p-selectin is expressed and appears on the surface of the cells. Platelet cells must retain the ability to activate when they are taken out of long-term storage to function normally for transfusion purposes. Cells need to be activated in vivo, so premature activation in vitro needs to be prevented. There is improved recovery and survival of platelets in vivo when p-selectin is kept low (Transfusion 2002;42:847–854 and Transfusion 2002;42: 1333–1339). Limits for values of certain vital qualities of blood components for use in treating patients are set by the Food and Drug Administration (FDA) of the United States (See Circular of Information for the Use of Human Blood and Blood Components or the FDA website (supra). Expression of p-selectin is optionally measured before adding mitochondrial enhancer and then at one or more time points after adding mitochondrial enhancer. At a selected time point, the percentage of cells expressing p-selectin is measured for both treated and untreated samples. The percentage of cells expressing p-selectin is the percent of cells activated (percent activation). The amount of change in activation due to the addition of mitochondrial enhancer is calculated by ((percent activation of treated−percent activation of untreated)/percent activation of untreated))*100=percent change in activation. If the percent change in activation is negative: absolute value of the percent change in activation=amount of decrease in activation, in percent, at that time point. In the practice of this invention, cellular activation is decreased as compared to cellular activation in a fluid to which mitochondrial enhancer has not been added.

Preferably activation is measured by detecting alpha granule release, such as by the presence of p-selectin expression, but any method known in the art may be used. Activation can be decreased by at least about 3%, by at least about 10%, and up to at least about 15%. In an embodiment of this invention, activation can be decreased by an amount between about 5% and about 50%.

Hypotonic stress response (HSR) is an assay used to determine if platelets have retained metabolic viability. It measures the ability of the cells to respond to osmotic shock after about a ten-minute recovery period. Percent HSR measures the percentage of cells that are able to recover in about ten minutes. The percentage of cells that are able to recover is the percent of reversal. The specified lower limit for HSR is about 36%. This assay is a photometric measurement of the platelets' ability to overcome the addition of a hypotonic solution. This activity reflects cell function (i.e., ability to maintain a functional membrane water pump) and is indicative of platelet recovery following storage. Hypotonic stress response has been demonstrated to be an important indicator of platelets' ability to survive in circulation following transfusion. Consequently, hypotonic stress response represents an important parameter for evaluating platelet biochemistry following storage. HSR is optionally measured before adding mitochondrial enhancer and then at one or more time points after adding mitochondrial enhancer. At a selected time point, HSR is measured for both treated and untreated samples. The amount of change in HSR due to the addition of mitochondrial enhancer is calculated by ((HSR of treated−HSR of untreated)/HSR of untreated))*100=percent change in HSR. If the percent change in HSR is not negative, the percent change in HSR is the amount of increase in HSR, in percent, at that time point. In the practice of this invention, hypotonic shock response (HSR) is increased, as compared to hypotonic shock response in a fluid to which mitochondrial enhancer has not been added. HSR can be increased by at least about 5%, by at least about 20%, and up to at least about 50%. In an embodiment of this invention, HSR can be increased by an amount between about 5% and about 25% as measured on Day 5 after adding mitochondrial enhancer.

Platelet swirl is a subjective, qualitative indicator of cell quality. When a blood bag is squeezed, healthy cells will swirl, creating a pattern which can be observed by the light reflecting off and through the cells. Platelet swirl is scored on a scale of from zero to three or four, with three or four being the healthiest. The quantity of cells swirling and the strength of the swirl are two characteristics that are considered. Platelet swirl is optionally measured before adding mitochondrial enhancer and then at one or more time points after adding mitochondrial enhancer. At a selected time point, platelet swirl is measured for both treated and untreated samples. The amount of change in platelet swirl due to the addition of mitochondrial enhancer is calculated by ((platelet swirl of treated−platelet swirl of untreated)/platelet swirl of untreated))*100=percent change in platelet swirl. If the percent change in platelet swirl is not negative, the percent change in platelet swirl is the amount of increase in platelet swirl, in percent, at that time point. In the practice of this invention, platelet swirl is increased, as compared to platelet swirl in a fluid to which mitochondrial enhancer has not been added. Platelet swirl can be increased by at least about 5% and by at least about 20%. In an embodiment of this invention, platelet swirl can be increased by an amount between about 5% and about 1000% as measured on Day 5 after adding mitochondrial enhancer.

In the practice of this invention, the pH of the fluid is increased and the rate of pH decrease can be decreased, as compared to pH and rate of pH decrease in a fluid to which mitochondrial enhancer has not been added. The increased rate of pH increase can also be measured, if pH increases. pH is optionally measured before adding mitochondrial enhancer and then at one or more time points after adding mitochondrial enhancer. At a selected time point, pH is measured for both treated and untreated samples. The amount of change in pH in pH units is the pH of treated samples−pH of untreated samples. To calculate the change in the rate of pH, pH is measured at two or more selected time points, wherein at least one of the time points occurs after adding mitochondrial enhancer. Time point 2 is measured after time point 1. The rate of pH change is calculated by (pH at time point 2−pH at time point 1)/(time point 2−time point 1)=rate of pH change in pH units per unit of time (such as hours or days). If the rate of pH change is negative, the pH is decreasing with time. pH of a fluid comprising a cellular blood component can decrease after photoradiation. The rate of pH change is calculated for both treated and untreated samples. The percent change in rate of pH change is ((rate of change of pH of treated−rate of change of pH of untreated)/rate of change of pH of untreated)*100. If the rate of pH change of treated, the rate of change of untreated, and the percent change in rate of pH change are negative, the rate of pH change is decreased by adding mitochondrial enhancer. The rate of pH decrease is the absolute value of the percent change in rate of pH change. The rate of pH decrease can be decreased by at least about 2%, by at least about 20%, and up to at least about 40%. In an embodiment of this invention, the rate of pH decrease can be decreased by an amount between about 2% and about 50%. The pH can be increased by at least about 0.1 units, by at least about 0.2, by at least about 0.35, and up to at least about 0.5. In an embodiment of this invention, the pH can be increased by an amount between about 0.1 and about 0.75. In an embodiment of this invention, the rate of pH decrease can be decreased by an amount between about 15% and about 50% on Day 5. In an embodiment of this invention, the pH is increased by an amount between about 0.1 and about 0.5 pH units, about twenty-four hours after mitochondrial enhancer is added to platelets that were stored for six days after apheresis.

In the practice of this invention, the rate of lactate production by cells in the fluid being treated and the amount of lactate produced are decreased, as compared to rate of lactate production and amount of lactate produced in a fluid to which mitochondrial enhancer has not been added. Amount of lactate in a fluid can be measured by any method known in the art. Amount of lactate is optionally measured before adding mitochondrial enhancer and then at one or more time points after adding mitochondrial enhancer. Amount of lactate can be measured as the concentration of lactate in the fluid. At a selected time point, amount of lactate is measured for both treated and untreated samples. The percent change of lactate production is the ((amount of lactate in treated samples−amount of lactate in untreated samples)/amount of lactate in untreated samples)*100. If the percent change of lactate production is negative, the percent decrease in lactate production due to adding mitochondrial enhancer is the absolute value of the percent change of lactate production. To calculate the rate of lactate production, amount of lactate is measured at two or more selected time points, wherein at least one of the time points occurs after adding mitochondrial enhancer. Time point 2 is measured after time point 1. The rate of lactate production is calculated by (amount of lactate at time point 2−amount of lactate at time point 1)/(time point 2−time point 1)=rate of lactate production in units in which lactate was measured (e.g. concentration) per unit of time (e.g. hours or days). The rate of change of lactate production is calculated for both treated and untreated samples. The percent change in the rate of lactate production is ((rate of change of lactate production of treated−rate of change of lactate production of untreated)/rate of change of lactate production of untreated)*100. If the rate of lactate production of treated and the rate of lactate production of untreated are positive, and the percent change in rate of lactate production is negative, the rate of lactate production is decreased by adding mitochondrial enhancer. The decrease in the rate of lactate production is the absolute value of the percent change in rate of lactate production. The rate of lactate production (micromoles per hour) can be decreased by at least about 5%, by at least about 50%, by at least about 80% and up to at least about 125%. In an embodiment of this invention, the rate of lactate production can be decreased by an amount between about 25% and about 100%. In an embodiment of this invention, the amount of lactate produced can be decreased by an amount between about 15% and about 100%. In an embodiment of this invention, the amount of lactate produced can be decreased by about 75%. In an embodiment of this invention, the rate of lactate production can be decreased by an amount between about 75% and about 100% about twenty-four hours after mitochondrial enhancer is added to platelets.

In the practice of this invention, the rate of glucose consumption by cells in the fluid, such as cellular blood components, and the amount of glucose consumed are decreased, as compared to rate of glucose consumption and amount of glucose consumed in a fluid to which mitochondrial enhancer has not been added. Glucose consumption is decreased by adding mitochondrial enhancer because adding mitochondrial enhancer enables a cell to better utilize mitochondrial biochemical pathways (citric acid cycle and electron transport chain) to generate energy, which generate more energy per glucose molecule compared to cytoplasmic biochemical pathways (glycolysis). Additionally, in platelets, mitochondrial biochemical pathways for generating energy don't require glucose. Glucose consumption can be measured by measuring the amount of glucose remaining in the fluid at a selected time point. The decrease in glucose consumption can be measured as the increase in the amount of glucose remaining in the fluid. The amount of glucose remaining in a fluid can be measured by any method known in the art. The amount of glucose remaining is optionally measured before adding mitochondrial enhancer and then at one or more time points after adding mitochondrial enhancer. The amount of glucose can be measured as the concentration of glucose (e.g. molecules/volume or molecules/cells) in the fluid. At a selected time point, amount of glucose is measured for both treated and untreated samples. The percent change of glucose consumption is the ((amount of glucose in treated samples−amount of glucose in untreated samples)/amount of glucose in untreated samples)*100. By this calculation, the percent change of glucose remaining in the fluid is the percent change of glucose consumption due to adding mitochondrial enhancer. To calculate the rate of glucose consumption, the amount of glucose remaining in the fluid is measured at two or more selected time points, wherein at least one of the time points occurs after adding mitochondrial enhancer. Time point 2 is measured after time point 1. The rate of glucose consumption is calculated by (amount of glucose remaining at time point 2−amount of glucose remaining at time point 1)/(time point 2−time point 1)=rate of glucose consumption in units in which glucose was measured (e.g. concentration) per unit of time (e.g. hours or days). The rate of glucose consumption, as calculated using amount of glucose remaining (FIG. 8) can be negative. The change in the rate of glucose consumption is calculated for both treated and untreated samples. The percent change in the rate of glucose consumption is ((rate of glucose consumption of treated−rate of glucose consumption of untreated)/rate glucose consumption of untreated)*100. If the rate of glucose consumption of treated and the rate of glucose consumption of untreated are negative, and the percent change in rate of glucose consumption is positive, the rate of glucose consumption is decreased by adding mitochondrial enhancer. The decrease in the rate of glucose consumption is the percent change in rate of glucose consumption. When the rate of glucose consumption is decreased, more glucose is left in the fluid at a selected time point. The rate of glucose consumption can be preferably decreased by at least about 5%, by at least about 25%, at least about 75%, and up to at least about 100%. In an embodiment of this invention, the rate of glucose consumption can be decreased by an amount between about 25% and about 150%. The amount of glucose consumed, as measured by the amount of glucose remaining, can be decreased by at least about 10%, by at least about 25%, and up to at least about 80%. In an embodiment of this invention, the amount of glucose consumed, as measured by the amount of glucose remaining, can be decreased by an amount between about 10% and about 150%, or between about 25% and about 100% on Day 3.

The extent of shape change (ESC) is the extent to which cellular blood component cells are able to change shape when contacted with an agonist. Healthy cells are able to change shape. Percent ESC measures the percent of cells able to change shape. The specified lower limit for ESC is 10%. ESC is optionally measured before adding mitochondrial enhancer and then at one or more time points after adding mitochondrial enhancer. At a selected time point, ESC is measured for both treated and untreated samples. The amount of change in ESC due to the addition of mitochondrial enhancer is calculated by ((ESC of treated−ESC of untreated)/ESC of untreated))*100=percent change in ESC. If the percent change in ESC is not negative, the percent change in ESC is the amount of increase in ESC, in percent, at that time point. In the practice of this invention, when the cellular blood component comprises platelets, the extent of cell shape change (ESC) is increased, as compared to the ESC of a fluid containing platelets to which mitochondrial enhancer has not been added. In an embodiment of this invention, the ESC can be increased by an amount between about 5% and about 125%. In an embodiment of this invention, the ESC can be increased by at least about 5%, by at least about 25%, by at least about 75%, and up to at least about 100%. In an embodiment of this invention, the ESC can be increased by at least about 75% on Day 5.

In the practice of this invention, the amount and/or the rate of oxygen consumption of the cellular blood component are/is increased, as compared to the amount and/or rate of oxygen consumption of a cellular blood component in a fluid to which mitochondrial enhancer has not been added. Amount of oxygen present in a gas above a fluid can be measured by any method known in the art. Glycolysis does not require oxygen, but the citric acid cycle does, therefore, when cells are utilizing mitochondrial biochemistry to generate energy (citric acid cycle), more oxygen is consumed and consequently less is left in the gas above the fluid containing the cells. Amount of oxygen is optionally measured before adding mitochondrial enhancer and then at one or more time points after adding mitochondrial enhancer. At a selected time point, amount of oxygen is measured for both treated and untreated samples. The percent change of oxygen consumption is also the percent change in oxygen remaining in the gas above the fluid. The percent change of oxygen consumption is the ((amount of oxygen in treated samples−amount of oxygen in untreated samples)/amount of oxygen in untreated samples)*100. If the percent change of oxygen consumption is negative, the percent increase in oxygen consumption due to adding mitochondrial enhancer is the absolute value of the percent change of oxygen consumption. To calculate the rate of oxygen consumption, amount of oxygen is measured at two or more selected time points, wherein at least one of the time points occurs after adding mitochondrial enhancer. Time point 2 is measured after time point 1. The rate of oxygen consumption is calculated by (amount of oxygen at time point 2−amount of oxygen at time point 1)/(time point 2−time point 1)=rate of oxygen consumption in units in which oxygen was measured (e.g. partial pressure) per unit of time (e.g. hours or days). The rate of oxygen consumption is calculated for both treated and untreated samples. The percent change in the rate of oxygen consumption is ((rate of oxygen consumption of treated−rate of oxygen consumption of untreated)/rate of oxygen consumption of untreated)*100. If the rate of oxygen consumption of treated and the rate of oxygen consumption of untreated are positive, and the percent change in rate of lactate production is negative, the rate of oxygen consumption is increased by adding mitochondrial enhancer. The increase in the rate of oxygen consumption is the absolute value of the percent change in rate of oxygen consumption. In an embodiment of this invention, the oxygen consumption can be increased by an amount between about 5% and about 125%. In an embodiment of this invention, the oxygen consumption can be increased by at least about 5%, by at least about 15%, by at least about 75%, by at least about 100%, and up to at least about 175%. In an embodiment of this invention, the oxygen consumption can be increased by at least about 50% at twenty-four hours after adding mitochondrial enhancer. In an embodiment of this invention, the rate of oxygen consumption can be increased by at least about 10% or between about 10% and about 50%.

In the practice of this invention, the rate of carbon dioxide production by cells in the gas above a fluid being treated and the amount of carbon dioxide produced are increased, as compared to the rate of carbon dioxide production and amount of carbon dioxide produced by a cell-containing fluid to which mitochondrial enhancer has not been added. Carbon dioxide is produced during mitochondrial biochemical pathways (citric acid cycle) for producing energy. Amount of carbon dioxide in the gas above a fluid can be measured by any method known in the art. Amount of carbon dioxide is optionally measured before adding mitochondrial enhancer and then at one or more time points after adding mitochondrial enhancer. Amount of carbon dioxide can be measured as the concentration (e.g. partial pressure) of carbon dioxide in the fluid. At a selected time point, amount of carbon dioxide is measured for both treated and untreated samples. The percent change of carbon dioxide production is percent change of carbon dioxide in the gas above a treated sample compared to an untreated sample. The percent change of carbon dioxide production is the ((amount of carbon dioxide in treated samples−amount of carbon dioxide in untreated samples)/amount of carbon dioxide in untreated samples)*100. If the percent change of carbon dioxide production is positive, it is the percent increase in carbon dioxide production due to adding mitochondrial enhancer. To calculate the rate of carbon dioxide production, amount of carbon dioxide is measured at two or more selected time points, wherein at least one of the time points occurs after adding mitochondrial enhancer. Time point 2 is measured after time point 1. The rate of carbon dioxide production is calculated by (amount of carbon dioxide at time point 2−amount of carbon dioxide at time point 1)/(time point 2−time point 1)=rate of carbon dioxide production in units in which carbon dioxide was measured (e.g. concentration) per unit of time (e.g. hours or days). The rate of change of carbon dioxide production is calculated for both treated and untreated samples. The percent change in the rate of carbon dioxide production is ((rate of change of carbon dioxide production of treated−rate of change of carbon dioxide production of untreated)/rate of change of carbon dioxide production of untreated)*100. If the rate of carbon dioxide production of treated and the rate of carbon dioxide production of untreated are positive, and the percent change in rate of carbon dioxide production is positive, the rate of carbon dioxide production is increased by adding mitochondrial enhancer.

Potential for aggregation is another vital quality that indicates whether blood platelets have maintained their functional integrity during storage. This potential is measured by using ADP and collagen to induce aggregation. An agonist is an agent that binds to a receptor and initiates a certain response. In an agonist-induced aggregation, aggregation or clumping is the response to the agonist. The agonists ADP and collagen are used to induce aggregation to determine if platelets have retained their ability to aggregate. In addition, when performing aggregation response tests, one can detect the presence of spontaneous aggregation, that is the platelets adhering to each other without the addition of an agonist. The occurrence of spontaneous aggregation has been correlated with removal of platelets from circulation, indicating the platelets have short survival times. Aggregation can be measured by any method known in the art. Aggregation is optionally measured before adding mitochondrial enhancer and then at one or more time points after adding mitochondrial enhancer. At a selected time point, aggregation is measured for both treated and untreated samples. The amount of change in aggregation due to the addition of mitochondrial enhancer is calculated by ((aggregation of treated−aggregation of untreated)/aggregation of untreated))*100=percent change in aggregation. If the percent change in aggregation is negative, the absolute value of the percent change in aggregation is the amount of decrease in aggregation, in percent, at that time point.

Vital cell qualities that determine allowed storage life of blood components are determined by the U.S. FDA (See Circular of Information for the Use of Human Blood and Blood Components or the FDA website, supra http). To increase storage life of a blood component, the vital cell quality that is limiting the storage life of that blood component must be improved. Additional vital cell qualities can be improved as well. In the practice of this invention, when 10 to 50 micromolar riboflavin is added to platelets, the vital quality of cellular blood component activation can be decreased by at least about 3%, and/or the vital quality of HSR can be increased by at least about 5%, and/or the vital quality of platelet swirl can be increased by at least about 5%, and/or the vital quality of pH of the fluid containing the cellular blood component can be increased by at least about 0.1 pH units, and/or the vital quality of rate of lactate production can be decreased by at least about 5%, and/or the vital quality of rate of glucose consumption can be decreased by at least about 5%, and/or the vital quality of rate of oxygen consumption can be increased by at least about 5%, and/or the vital quality of carbon dioxide production can be increased by about 5%. In an embodiment of this invention, the cellular blood component is platelets and they can be stored, e.g. for a period greater than five days, for between about five days and about seven days.

Collected platelets can be concentrated before treating using the methods of this invention. Platelets can be concentrated by any method known in the art, such as using apheresis devices while collecting blood or from previously collected samples of whole blood. In an embodiment of this invention, platelets are hyperconcentrated to form hyperconcentrated platelets (HCP) by centrifugation at 3000 times gravity (3000×G) for fifteen minutes and allowed to rest for one hour. In an embodiment of this invention, HCP are resuspended in autologous plasma, resulting in approximately five trillion platelets per milliliter. Fluid can consist essentially of platelets in plasma or cell culture media, e.g. comprising platelets and between about 5% and about 95% plasma or media.

The methods provided by this invention optionally further comprise photoradiating, adding photoactivator, adding nitric oxide, adding quencher, adding glycolysis inhibitor, adding oxygen, and/or adding process enhancers to the fluid being treated.

Pathogen reduction using photoradiation requires mixing a photosensitizer with the material to be decontaminated. Mixing may be done by simply adding the photosensitizer or a solution containing the photosensitizer to the fluid to be decontaminated. In one system, the material to be decontaminated to which the photosensitizer has been added is flowed past a photoradiation source, and the flow of the material provides sufficient turbulence to distribute the photosensitizer throughout the fluid to be decontaminated. In another system, the fluid and photosensitizer are placed in a photopermeable container and irradiated in batch mode, preferably while agitating the container to fully distribute the photosensitizer and expose all the fluid to the radiation.

The amount of photosensitizer to be mixed with the fluid will be an amount sufficient to adequately reduce microorganisms therein, but less than a toxic (to humans or other mammals) or insoluble amount. Optimal concentrations of desired photosensitizers may be readily determined by those skilled in the art without undue experimentation.

The fluid containing the photosensitizer is exposed to photoradiation of the appropriate wavelength to activate the photosensitizer, using an amount of photoradiation of sufficient energy to activate the photosensitizer as described above, but less than that which would cause non-specific damage to the biological components or substantially interfere with biological activity of other proteins present in the fluid. The wavelength used will depend on the photosensitizer selected, as is known in the art or readily determinable without undue experimentation following the teachings hereof. After exposure to the light energy, the pathogen reduced cellular blood component may be kept in the pathogen reduction solution, or may be transferred to a storage solution.

Photoradiation to reduce pathogens is performed by methods known in the art or by methods described in references included herein. An amount of energy is supplied to the fluid using photoradiation. Preferably the amount of energy supplied is sufficient to reduce pathogens which may exist in the fluid, but also does not substantially interfere with the biological activity of the blood component(s) contained in the fluid. The biological activity of blood component(s) in the fluid at least meets minimum standards for medical and veterinary use for standard storage times for the specific blood component, e.g., five or preferably seven days for platelets. Pathogen reduction methods of this invention are described as using flux (energy) in units of joules (J) per unit area ($cm^2$) per unit time (min). A time length of photoradiation is selected to accomplish delivering a total amount of energy selected to substantially reduce pathogens in the fluid being treated. Some lamps useful for providing the required energy are VHO lights with a mercron ballast, T8 lights with an icecap ballast, or T8 lights with an icecap ballast and quartz attenuator. Photoradiation can be delivered continuously or in a segmented (interrupted) fashion. The photoradiation is preferably within the ultraviolet range or the visible range. A photoradiation light source can be selected that is capable of providing light of about 300 nm to about 700 nm, or between about 340 nm to about 650 nm of radiation. The energy delivered to the fluid is an amount sufficient to activate a photosensitizer, e.g., between about 5 $J/cm^2$ and about 360 $J/cm^2$. In an embodiment of this invention, the total time of photoradiation is sufficient to substantially reduce pathogens, e.g., between about three and about thirty minutes. To "substantially inactive pathogens" means to reduce their ability to reproduce, preferably by killing them, to levels in a blood component such that the blood component may be safely administered to a patient. Ultraviolet wavelength of 320 nm is useful in the practice of this invention.

This invention provides methods for improved pathogen reduction. Pathogen reduction processes using photoradiation are improved by the addition of mitochondrial enhancer. Addition of mitochondrial enhancer to a fluid containing a blood product containing mitochondria prevents damage to the blood product from photoradiation, which allows the use of high photoradiation energies, which are more effective at reducing pathogens. Prevention of damage to the blood product is indicated by improvement to vital cell qualities in fluids treated with mitochondrial enhancer compared to fluids treated at equivalent energies without addition of mitochondrial enhancer, before, after, or during photoradiation. High energies useful in the practice of this invention include more than about 30 $J/cm^2$, more than about 50 $J/cm^2$, more than about 80 $J/cm^2$, more than about 100 $J/cm^2$, more than about 120 $J/cm^2$, more than 120 $J/cm^2$, more than about 180 $J/cm^2$, more than 180 $J/cm^2$, between about 5 $J/cm^2$ and about 360 $J/cm^2$, between about 25 $J/cm^2$ and about 180 $J/cm^2$, between about 75 $J/cm^2$ and about 120 $J/cm^2$, and between about 120 $J/cm^2$ and about 180 $J/cm^2$ ultraviolet photoradiation. This invention provides an improved method for treating a fluid comprising a cellular blood component to reduce pathogens which may be present therein, comprising the steps of:

(a) adding an reduction-effective, substantially non-toxic amount of a photosensitizer to said fluid;

(b) adding an effective amount of mitochondrial enhancer to said fluid and in an amount sufficient to improve a vital quality of said cellular blood component; and (c) exposing said fluid to photoradiation of sufficient energy to activate said photosensitizer, for a sufficient time to substantially reduce said pathogens.

In the practice of this invention the photoradiation is preferably applied at an energy more than about 25 $J/cm^2$, wherein the photoradiation is substantially non-toxic to the cellular blood component. Amounts of photoradiation energy and mitochondrial enhancer are selected such that extent of pathogen reduction and vital cell quality immediately after photoradiation and at about 24 hours after photoradiation are about the same or better than an equivalent process without mitochondrial enhancer at a lower energy. Examples of lower energies are about five to about 15 J/cm². In the practice of this invention, photoradiation is preferably delivered at more than about 25 J/cm² or more than about 40 J/cm². In the practice of this invention, photoradiation is delivered at an energy between about 25 J/cm² and about 120 J/cm², between about 25 J/cm² and about 180 J/cm², or between about 25 J/cm² and about 360 J/cm².

Fluids may optionally be mixed before or during photoradiation. Mixing may enhance dissolution of components. Before or during photoradiation, the fluid may be mixed by mixing and/or shaking at a speed between about 70 cpm and about 150 cpm, or between about 120 cpm and about 135 cpm. When performed before photoradiation, mixing can be performed for about one to about ten minutes. The mixing and shaking may be performed in any motion known to the art, including mixing and shaking using a to-and-fro motion. One or more of the light sources may move in a coordinated manner with the movement of the mixing. Mixing enables the majority of the photosensitizer and fluid contained within the container to be exposed to the light emitted from each of the discrete radiation sources by continually replacing the exposed fluid at the light-fluid interface with fluid from other parts of the bag not yet exposed to the light. Such mixing continually brings to the surface new fluid to be exposed to light. Photoradiation can be performed at a temperature that allows for reduction of pathogens and does not interfere with the biological activity of cellular blood components. Photoradiated fluids containing cellular blood components can be stored at temperatures known in the art for storing blood products.

Materials which may be treated by methods of this invention that involve photoradiation greater than ambient light include any materials which are adequately permeable to photoradiation to provide sufficient light to achieve pathogen reduction, or which can be suspended or dissolved in fluids which have such permeability to photoradiation. Plasma and cell culture media containing cellular blood components are permeable to photoradiation.

Decontamination methods of this invention do not destroy the biological activity of fluid components other than microorganisms. As much biological activity of these components as possible is retained, although in certain instances, when the methods are optimized, some loss of biological activity, e.g., denaturization of protein components, must be balanced against effective decontamination of the fluid.

In addition to treating whole blood, fluids containing cellular blood products and cell-containing bodily fluids, this method is useful for treating other cell-containing fluids including fluids which are meant for nourishment of humans or animals such as fruit and vegetable juices.

EXAMPLES

Example 1

Treatment of Platelets with Riboflavin

Platelets were collected using standard collection methods using a COBE® Spectra™ apheresis machine (manufactured by Gambro BCT, Lakewood, Colo., USA). Fresh platelets were less than 24 hours old after collection via apheresis. Other apheresis machines useful for collecting transfusion-quality platelets are useful in the practice of this invention. Collected platelets were diluted in a solution containing 0.9% sodium chloride with either 0 or 10 μM riboflavin. Samples were saturated with air via vigorous mixing. Platelets were exposed to no photoradiation greater than ambient light. Results are shown in Table 1.

TABLE 1

| Riboflavin Concentration (μM) | Photoradiation $E_{UV}$ J/cm² | Photoradiation $E_{VIS}$ J/cm² | Lactate Production Rate (μM/hr) | Glucose Consumption Rate (μM/hr) | $O_2$ Consumption (μM/hr/10¹² plts) Day 0 | $O_2$ Consumption (μM/hr/10¹² plts) 24 hrs | pH Day 0 |
|---|---|---|---|---|---|---|---|
| 0 | 0 | 0 | 31 | 18 | 92 | 114 | |
| 10 | 0 | 0 | 29 | 19 | 136 | 124 | |
| 0 | 0 | 0 | 50 | | | 87 | 6.92 |
| 10 | 0 | 0 | 68 | | | 186 | 6.91 |

Cell quality indicators were improved or unaffected by the addition of riboflavin.

Example 2

Treatment of Platelets with Riboflavin and Visible Light

Platelets were collected using standard collection methods using a COBE® Spectra™ apheresis system (manufactured by Gambro BCT, Lakewood, Colo., USA) and TRIMA® apheresis system (available from Gambro BCT, Lakewood, Colo., USA). Fresh platelets were less than 24 hours old after collection via apheresis. Other apheresis machines useful for collecting transfusion-quality platelets are useful in the practice of this invention. Collected platelets were diluted in a solution containing 0.9% sodium chloride with either 0 or 10 μM riboflavin. Samples were saturated with air via vigorous mixing. The samples were irradiated with a Dymax light source using one bulb at 15.5 mW/cm² for varying times. The UV component of the light was filtered out using a polycarbonate filter. Exposure time was 31 minutes. Results are shown in Table 2.

TABLE 2

| Riboflavin Concentration (μM) | Photoradiation E_UV (J/cm²) | Photoradiation E_VIS (J/cm²) | Lactate Production Rate (μM/hr) | Glucose Consumption Rate (μM/hr) | O₂ Consumption (μM/hr/10¹²plts) Day 0 | O₂ Consumption (μM/hr/10¹²plts) 24 hrs | pH Day 0 |
|---|---|---|---|---|---|---|---|
| 0 | 0 | 40 | 83 | 42 | 80 | 63 | |
| 10 | 0 | 40 | 30 | 13 | 117 | 94 | |
| 0 | 0 | 40 | 237 | | | 91 | 6.89 |
| 10 | 0 | 40 | 239 | | | 140 | 6.84 |

Cell quality indicators were improved or unaffected by addition of riboflavin.

Example 3

Treatment of Platelets with Riboflavin and Ultraviolet and Visible Light

Platelets were collected using standard collection methods using a COBE® Spectra™ apheresis machine (manufactured by Gambro BCT, Lakewood, Colo., USA). Fresh platelets were less than 24 hours old after collection via apheresis. Other apheresis machines useful for collecting transfusion-quality platelets are useful in the practice of this invention. Collected platelets were diluted in a solution containing 0.9% sodium chloride with either 0 or 10 μM riboflavin. Samples were saturated with air via vigorous mixing. The samples were irradiated with a Dymax light source using one bulb at 15.5 mW/cm² for varying times. Results are shown in Tables 3 and 4.

TABLE 3

| Riboflavin Concentration (μM) | Photoradiation E_UV (J/cm²) | Photoradiation E_VIS (J/cm²) | Lactate Production Rate (μM/hr) | Glucose Consumption Rate (μM/hr) | O₂ Consumption (μM/hr/10¹²plts) Day 0 | O₂ Consumption (μM/hr/10¹²plts) 24 hrs | pH Day 0 |
|---|---|---|---|---|---|---|---|
| 0 | 29 | 40 | 327 | 115 | 20 | 0 | |
| 10 | 29 | 40 | 60 | 39 | 55 | 111 | |

When riboflavin was added, lactate production rate was decreased by about 82%, glucose consumption rate was decreased by about 66%, and oxygen consumption rate was increased by about 175%. Other cell quality indicators were improved as well. The energy of both ultraviolet and visible light combined was 40 J/cm².

TABLE 4

| Riboflavin Concentration (μM) | Wavelength | Exposure Time (min) | Oxygen Consumption (μM/hr/10¹² plts) Day 0 | Oxygen Consumption (μM/hr/10¹² plts) 24 hrs | pH Day 0 | pH 24 hrs |
|---|---|---|---|---|---|---|
| 0 | UV + VIS | 16 | | 22 | 6.87 | |
| 10 | UV + VIS | 16 | | 86 | 6.86 | |

When riboflavin was added, oxygen consumption was increased by about 13%. Other cell quality indicators were improved as well.

Figure 5:
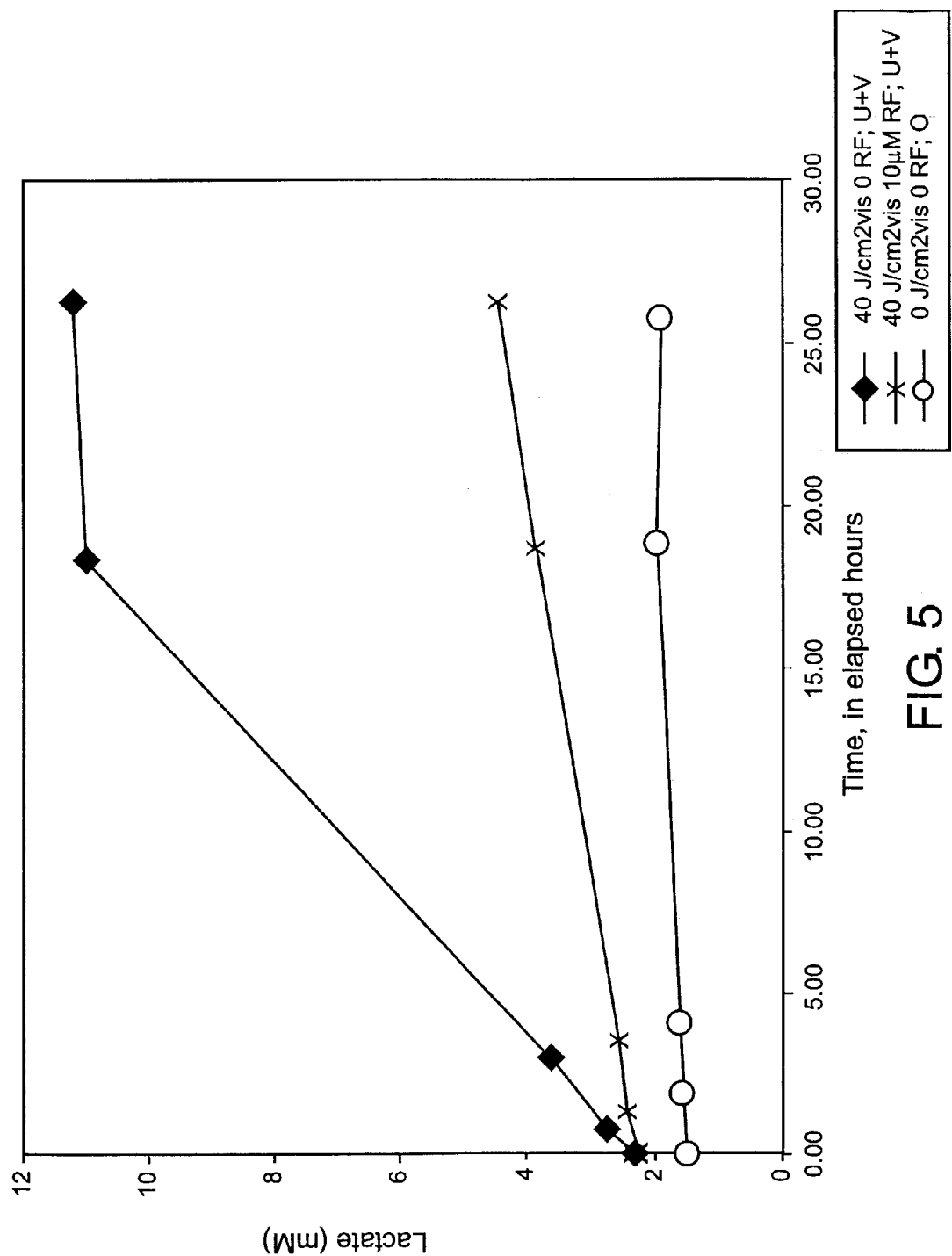
FIG. 5 is a graph showing the effect of mitochondrial enhancer on lactate production by platelets as a function of storage time (days).
Figure 6:
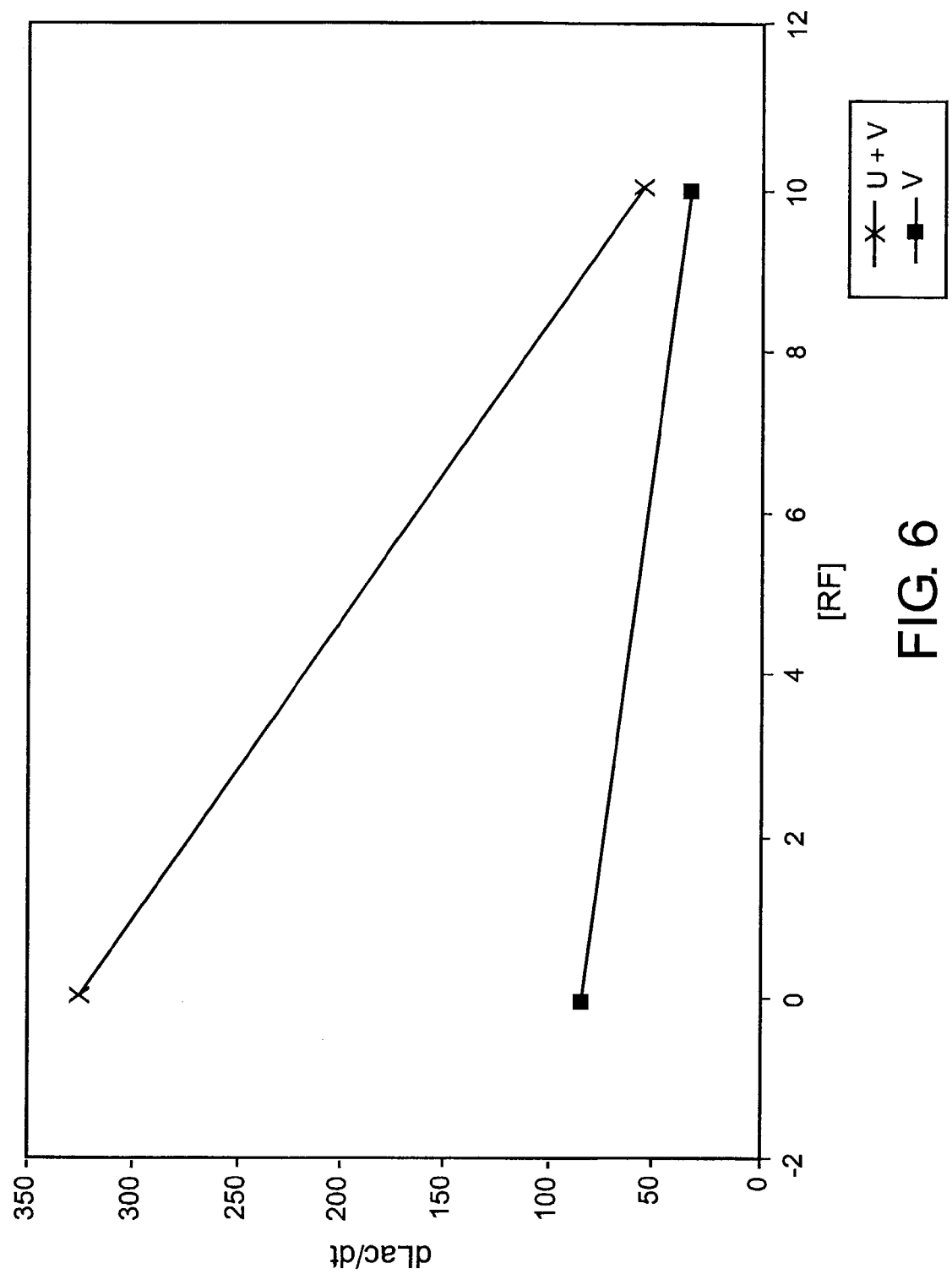
FIG. 6 is a graph showing the effect of mitochondrial enhancer on the rate of lactate production by platelets as a function of mitochondrial enhancer concentration.

In a related experiment, 30 ml aliquots of concentrated platelets, with varying amounts of riboflavin from 0 to 10 micromolar, were photoradiated with 365 nm UV to 29 J/cm² and 419 nm visible light to 40 J/cm². Cell quality indicators were measured for about 25 hours following photoradiation. FIG. 5 is a graph showing the effect of mitochondrial enhancer on lactate production (lactate concentration mM/1000 cells) by platelets as a function of storage time (days). The amount of lactate produced decreased about 70% with riboflavin. FIG. 6 is a graph showing the effect of mitochondrial enhancer on the rate of lactate production by platelets as a function of mitochondrial enhancer concentration. The rate of lactate production decreased about 80% when 10 micromolar riboflavin was added compared to no riboflavin. The rate of lactate production decreased with increasing amounts of riboflavin.

Example 4

Treatments of Platelets with NaCN to Simulate Electron Transport Chain Damage

Sodium cyanide was used as a control to simulate damage to the electron transport chain. Results are shown in Table 5.

TABLE 5

| Sodium Cyanide | Riboflavin Concentration (μM) | Exposure Wavelength | Time (min) | Oxygen Consumption (μM/hr/10$^{12}$ plts) Day 0 | 24 hrs | Lactate Production (μM/hr) 24 hrs | pH Day 0 | 24 hrs |
|---|---|---|---|---|---|---|---|---|
| absent | 0 | 0 | 0 | 87 | 50 | | 6.92 | |
| present | 0 | 0 | 0 | 14 | | | 6.92 | |

Example 5

Treatment of Stored Platelets with Riboflavin

The platelets were 6-day-old apheresis platelets which had been stored under standard conditions at a local blood bank. Products were placed into 30 mL bags for irradiation and 24 hour storage. Results are shown in Table 6.

TABLE 6

| Platelet Storage (days) | Riboflavin Concentration (μM) | Exposure Wavelength | Time (min) | Oxygen Consumption (μM/hr/10$^{12}$ plts) Day 0 | 24 hrs | Lactate Production (μM/hr) 24 hrs | pH Day 0 | 24 hrs |
|---|---|---|---|---|---|---|---|---|
| 6 | 0 | 0 | 0 | 118 | 63 | 444 | 7.10 | 6.97 |
| 6 | 10 | 0 | 0 | 116 | 168 | 40 | 7.08 | 6.71 |

When riboflavin was added to stored platelets, lactate production decreased by about 91%. Other cell quality indicators were improved as well.

Example 6

Treatment of Stored Platelets with Riboflavin and Visible Light

The platelets were 6-day-old apheresis platelets which had been stored under standard conditions at a local blood bank. Products were placed into 30 mL bags for irradiation and 24 hour storage. The light source used was a Dymax light source with a single bulb. UV light was filtered out using a polycarbonate sheet. Exposure time was adjusted to deliver 40 J/cm$^2$. Results are shown in Table 7.

TABLE 7

| Platelet Storage (days) | Conc. B$_2$ (μM) | Wavelength | Exposure Time (min) | Lactate Production (μM/hr) 24 hrs | pH Day 0 | 24 hrs |
|---|---|---|---|---|---|---|
| 6 | 0 | VIS | 31 | 404 | 7.09 | 6.48 |
| 6 | 10 | VIS | 31 | | 7.07 | 6.84 |

Example 7

Treatment of Stored Platelets with Riboflavin and Visible and Ultraviolet Light

The platelets were 6-day-old apheresis platelets which had been stored under standard conditions at a local blood bank. Products were placed into 30 mL bags for irradiation and 24 hour storage. The light source used was a Dymax light source with a single bulb. UV light was filtered out using a polycarbonate sheet. Exposure time was adjusted to deliver 40 J/cm$^2$ combined visible light and ultraviolet light. Results are shown in Table 8.

TABLE 8

| Platelet Storage (days) | Conc. B$_2$ (μM) | Wavelength | Exposure Time (min) | Lactate Production (μM/hr) 24 hrs | pH Day 0 | 24 hrs |
|---|---|---|---|---|---|---|
| 6 | 0 | UV + VIS | 16 | 545 | 7.08 | 6 |
| 6 | 10 | UV + VIS | 16 | 177 | 7.07 | 6.12 |

Example 8

Figure 2:
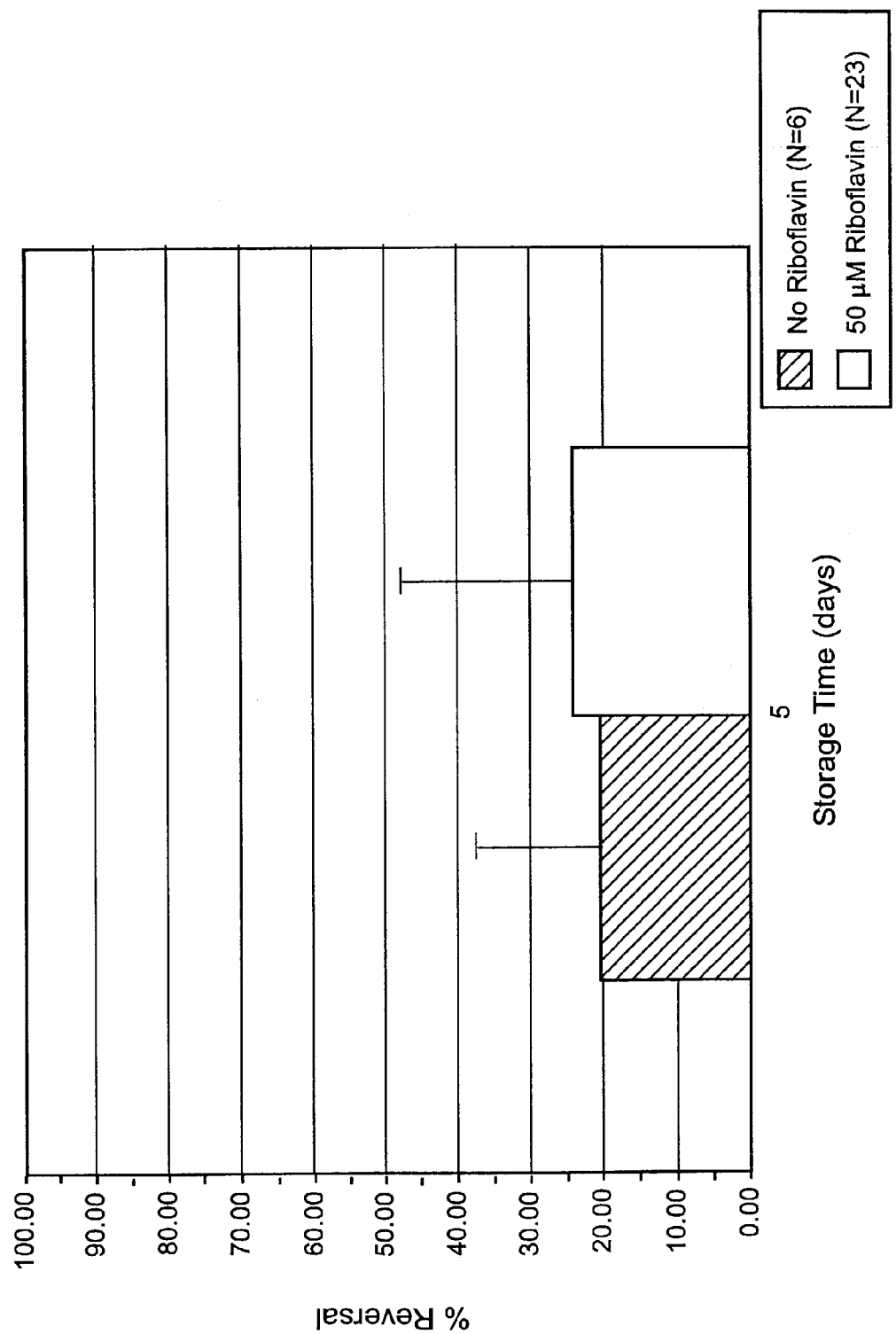
FIG. 2 is a graph showing the effect of mitochondrial enhancer on hypotonic shock response (HSR), % reversal, of platelets as a function of storage time (days).
Figure 3:
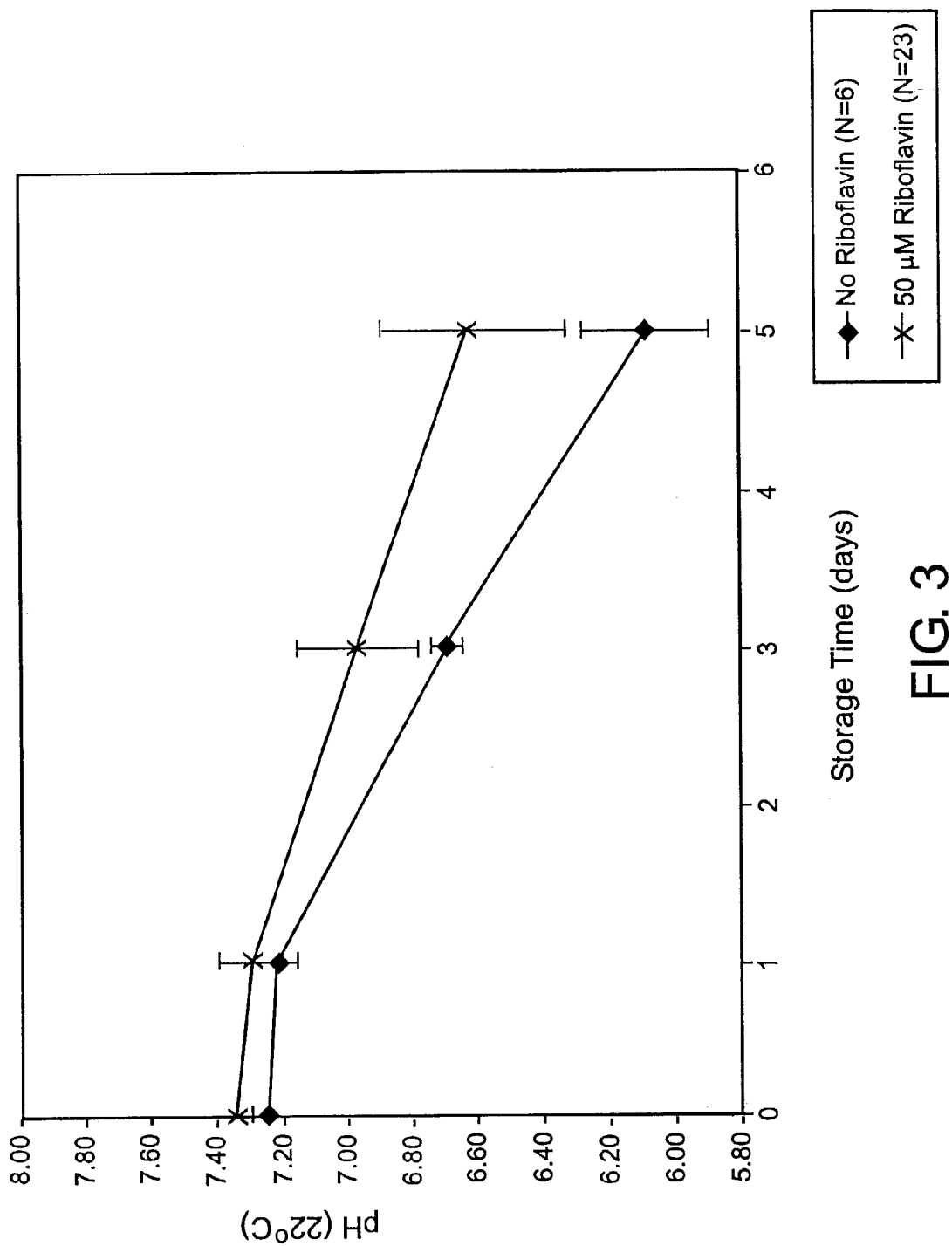
FIG. 3 is a graph showing the effect of mitochondrial enhancer on pH of the stored fluid as a function of storage time (days).
Figure 4:
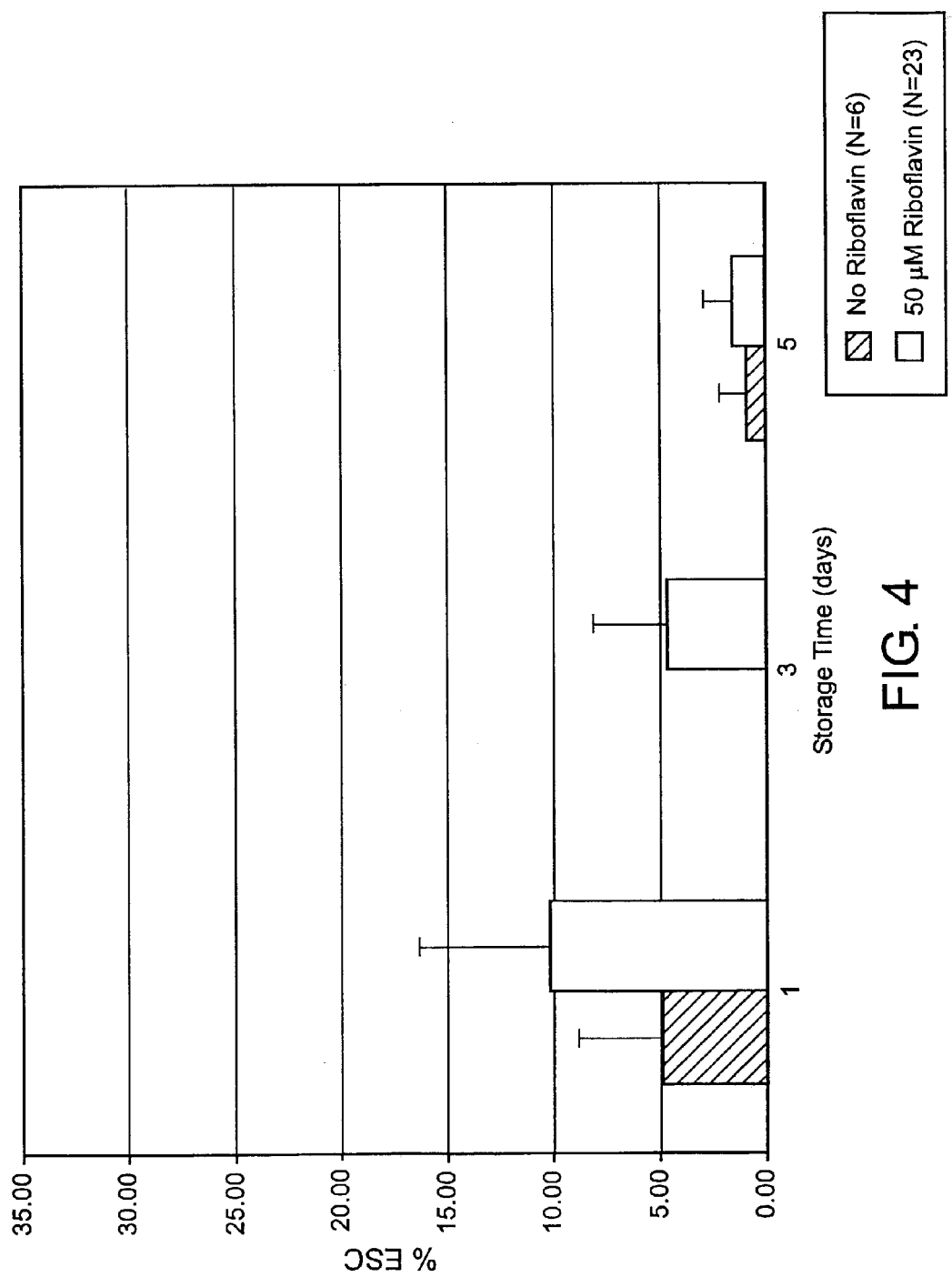
FIG. 4 is a graph showing the effect of mitochondrial enhancer on % extent of shape change (ESC) of platelets as a function of storage time (days).
Figure 8:
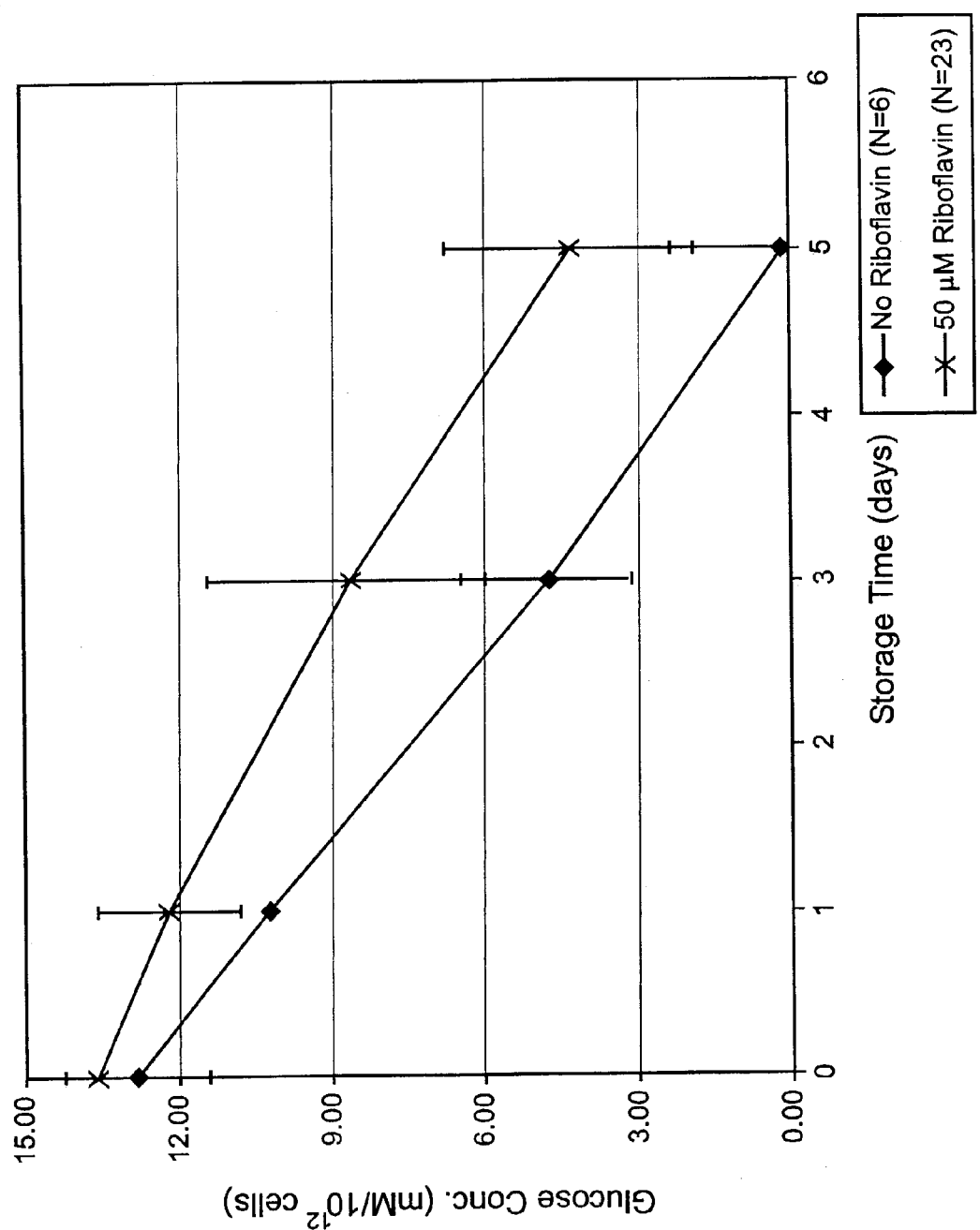
FIG. 8 is a graph showing the effect of mitochondrial enhancer on glucose consumption by platelets as a function of storage time (days).
Figure 9:
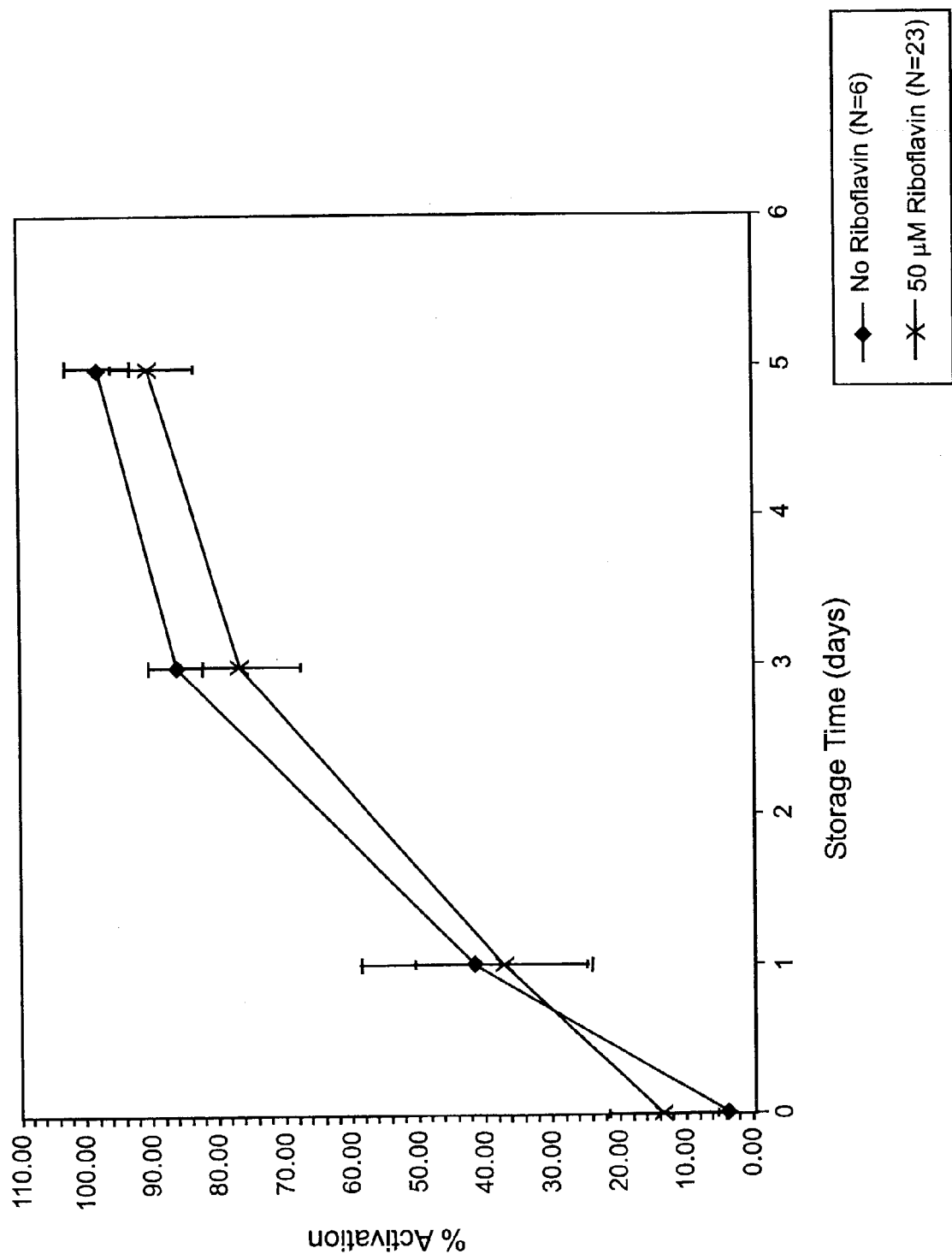
FIG. 9 is a graph showing the effect of mitochondrial enhancer on p-selectin expression (% activation), by platelets as a function of storage time (days).

Treatment of Platelets with Riboflavin and Ultraviolet Light 278 ml of 90% PCO in Sengewald bags, with 50 micromolar riboflavin (23 samples) and without riboflavin (6 samples), while stirring at 120 cpm (adding oxygen), were irradiated with 320 nm UV photoradiation to a total of 7 J/cm$^2$. Vital cell quality indicators were measured at various storage times after photoradiation. FIG. 8 is a graph showing the effect of mitochondrial enhancer on glucose consumption (glucose concentration mM/10$^{12}$ cells) by platelets as a function of storage time (days). The amount and rate of glucose consumption decreased with the addition of riboflavin. FIG. 1 is a graph showing the effect of mitochondrial enhancer on platelet swirl (0–4 units) of cellular blood components as a function of storage time (days). Platelet swirl increased on Day 1 with the addition of riboflavin. FIG. 2 is a graph showing the effect of mitochondrial enhancer on hypotonic shock response (HSR), % reversal, of platelets as a function of storage time (days). HSR increased with the addition of riboflavin. FIG. 3 is a graph showing the effect of mitochondrial enhancer on pH of the stored fluid as a function of storage time (days). pH was higher with riboflavin. pH decreased after photoradiation at a slower rate with riboflavin, compared to without riboflavin. FIG. 9 is a graph showing the effect of mitochondrial enhancer on p-selectin expression (GMP-140 (granule membrane protein-140) expression, also called % activation, by platelets as a function of storage time (days). Percent activation is the percentage of cells expressing p-selectin. P-selectin expression was decreased with riboflavin. FIG. 4 is a graph showing the effect of mitochondrial enhancer on percent extent of shape change (ESC) of platelets as a function of storage time (days). ESC % was increased with riboflavin.

Example 9

Figure 7:
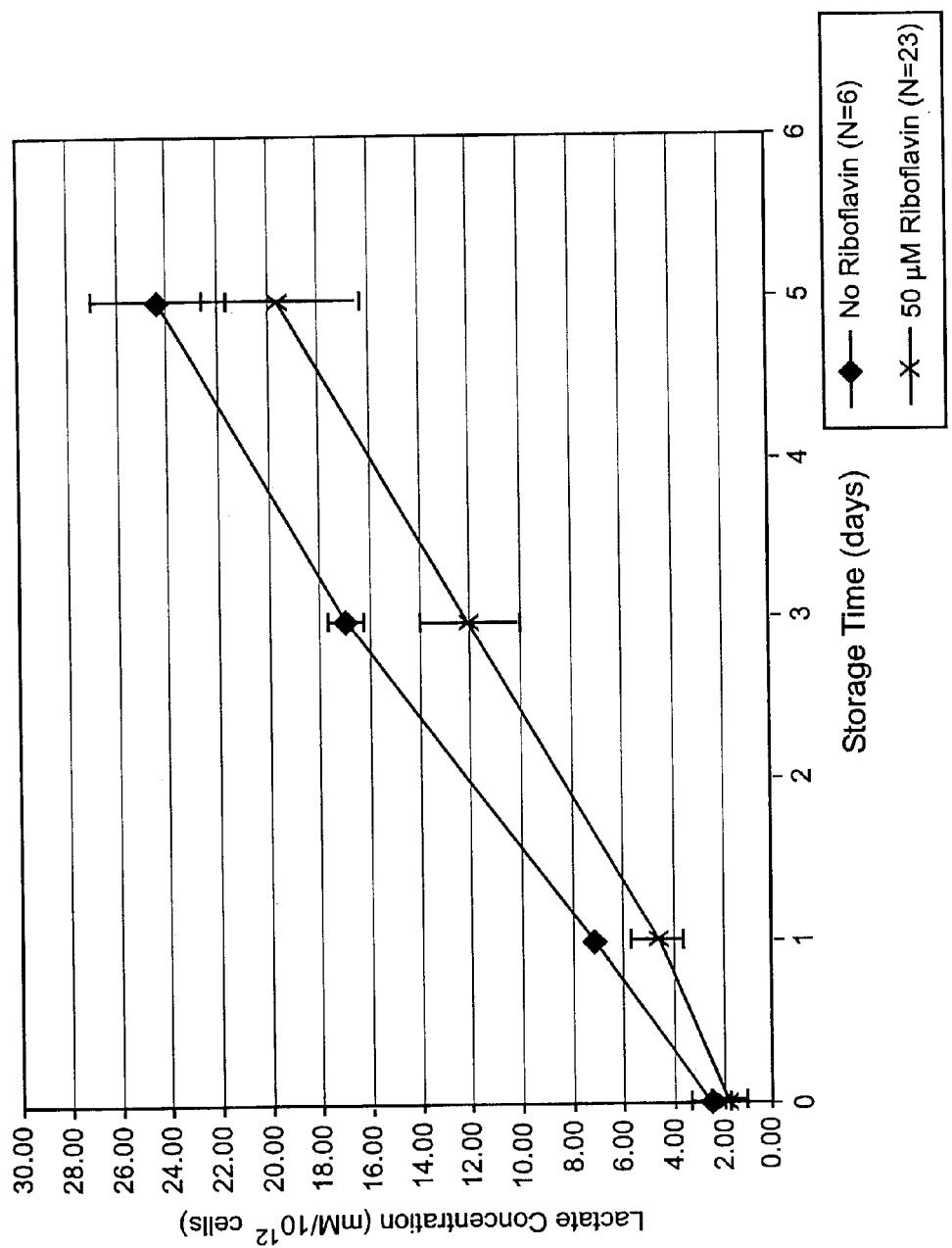
FIG. 7 is a graph showing the effect of mitochondrial enhancer on lactate production by platelets as a function of storage time (days).
Figure 10:
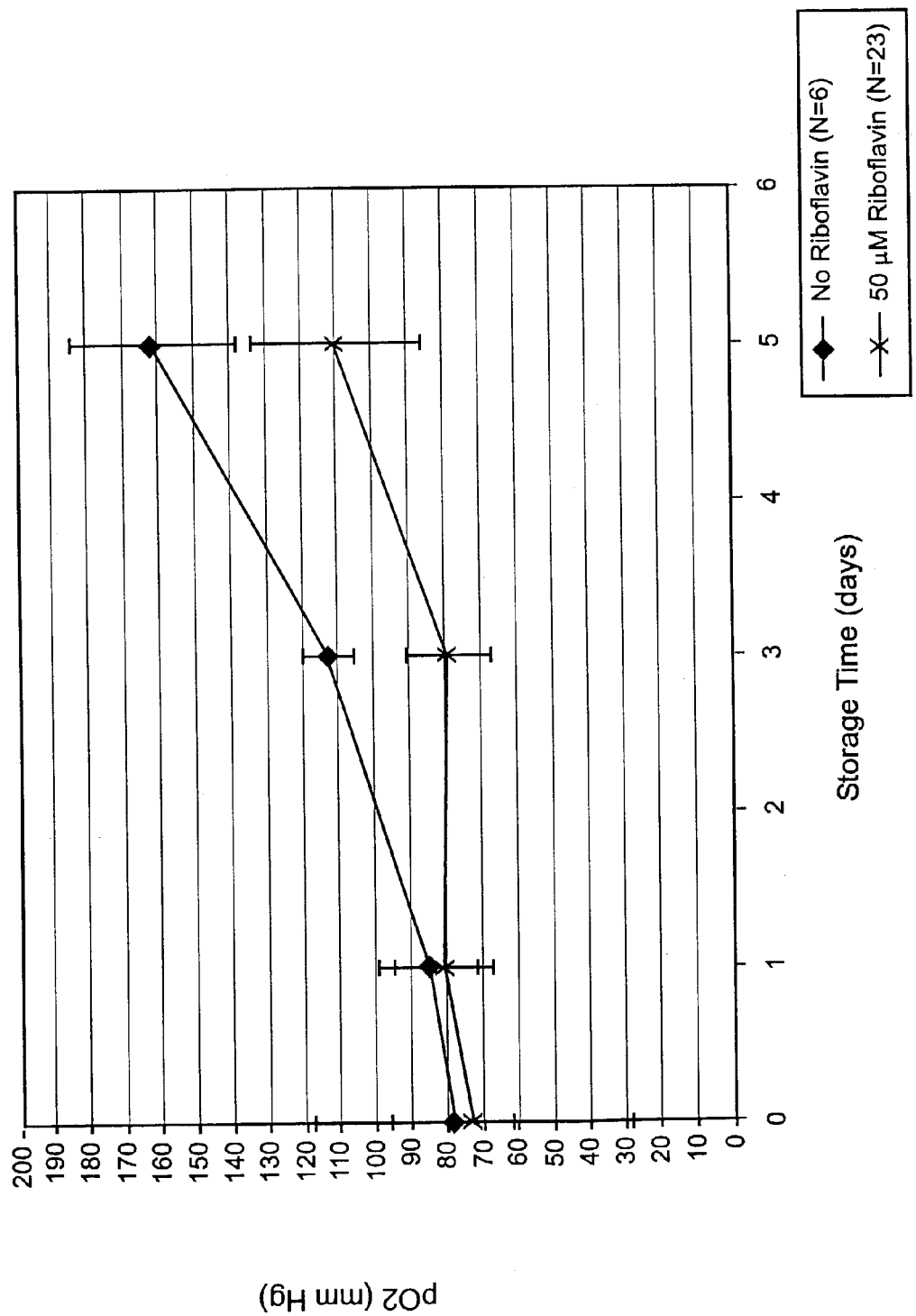
FIG. 10 is a graph showing the effect of mitochondrial enhancer on oxygen consumption by platelets as a function of storage time (days).

Treatment of Platelets with Riboflavin and Ultraviolet Light 278 ml of 90% PCO in Sengewald bags, with 50 micromolar riboflavin (23 samples) and without riboflavin (6 samples), while stirring at 120 cpm (adding oxygen), were irradiated with 320 nm UV photoradiation to a total of 7 J/cm$^2$. Vital cell quality indicators were measured at various storage times after photoradiation. FIG. 7 is a graph showing the effect of mitochondrial enhancer on lactate production by platelets as a function of storage time (days). Lactate production was decreased with riboflavin by between about 20% and about 30%. The rate of lactate production was decreased by about 25%. FIG. 8 is a graph showing the effect of mitochondrial enhancer on glucose consumption by platelets as a function of storage time (days). Glucose consumption was decreased by riboflavin by between about 15% and about 85%. Rate of glucose consumption was decreased by about 36%. FIG. 9 is a graph showing the effect of mitochondrial enhancer on p-selectin expression (% activation), by platelets as a function of storage time (days). Activation was reduced by riboflavin by about 10%. FIG. 10 is a graph showing the effect of mitochondrial enhancer on oxygen consumption by platelets as a function of storage time (days). FIG. 10 is alternatively labeled as a graph of oxygen concentration which is indicative of consumption because the lower the oxygen concentration, the higher the oxygen consumption. Oxygen consumption was increased by about 30%. The rate of oxygen consumption was increased by about 37.5%.

Example 10

Effect of Riboflavin on Reduction of Vaccinia Virus at Various Energy Levels

Figure 11:
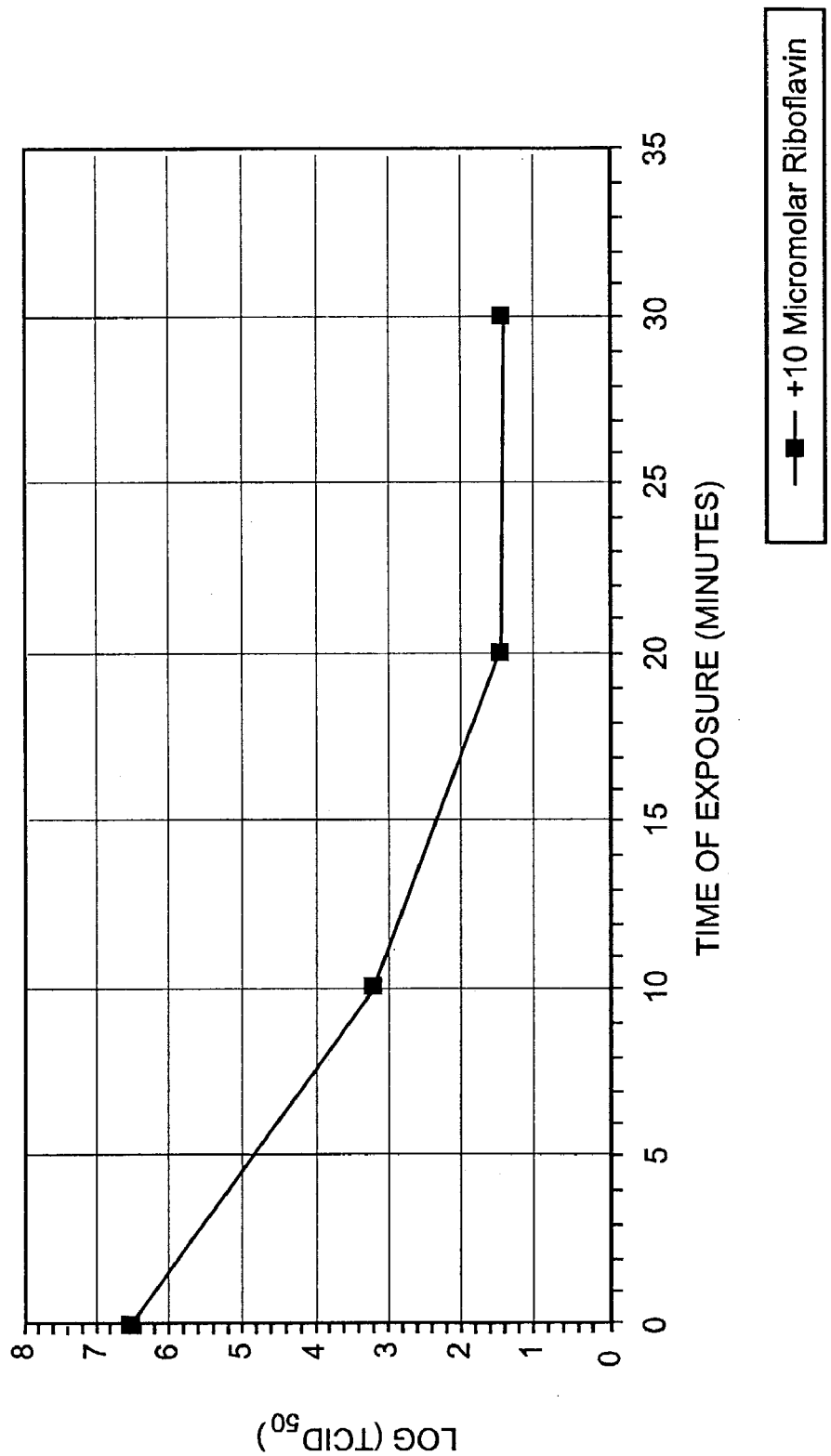
FIG. 11 is a graph showing the effect of mitochondrial enhancer on reduction kinetics of vaccinia virus as a function of photoradiation exposure time (delivered energy).

Vaccinia virus was used to innoculate Isolyte S media (Halpern, et al. (1997) Crit Care Med. 25(12):2031–8). Samples also contained 10 micromolar riboflavin. Vaccinia virus was titered before and after exposure and measured as TCID$_{50}$ (tissue culture infection dose for 50% of the tissue culture cells). UV photoradiation was continued for a total of 30 minutes (40 J/cm$^2$), with vaccinia virus titered at ten minute intervals. More energy was delivered with longer exposure times. FIG. 11 is a graph showing the effect of mitochondrial enhancer on reduction kinetics of vaccinia virus as a function of photoradiation exposure time (delivered energy). Vaccinia virus reduction increased with increasing exposure time (energy). There was no reduction without riboflavin. Results are shown in Table 9.

TABLE 9

| TIME | Log Reduction in the presence of 10 μM Riboflavine |
|---|---|
| 0 | 6.56 |
| 10 | 3.22 |
| 20 | 1.5 |
| 30 | 1.5 |

Example 11

Figure 12:
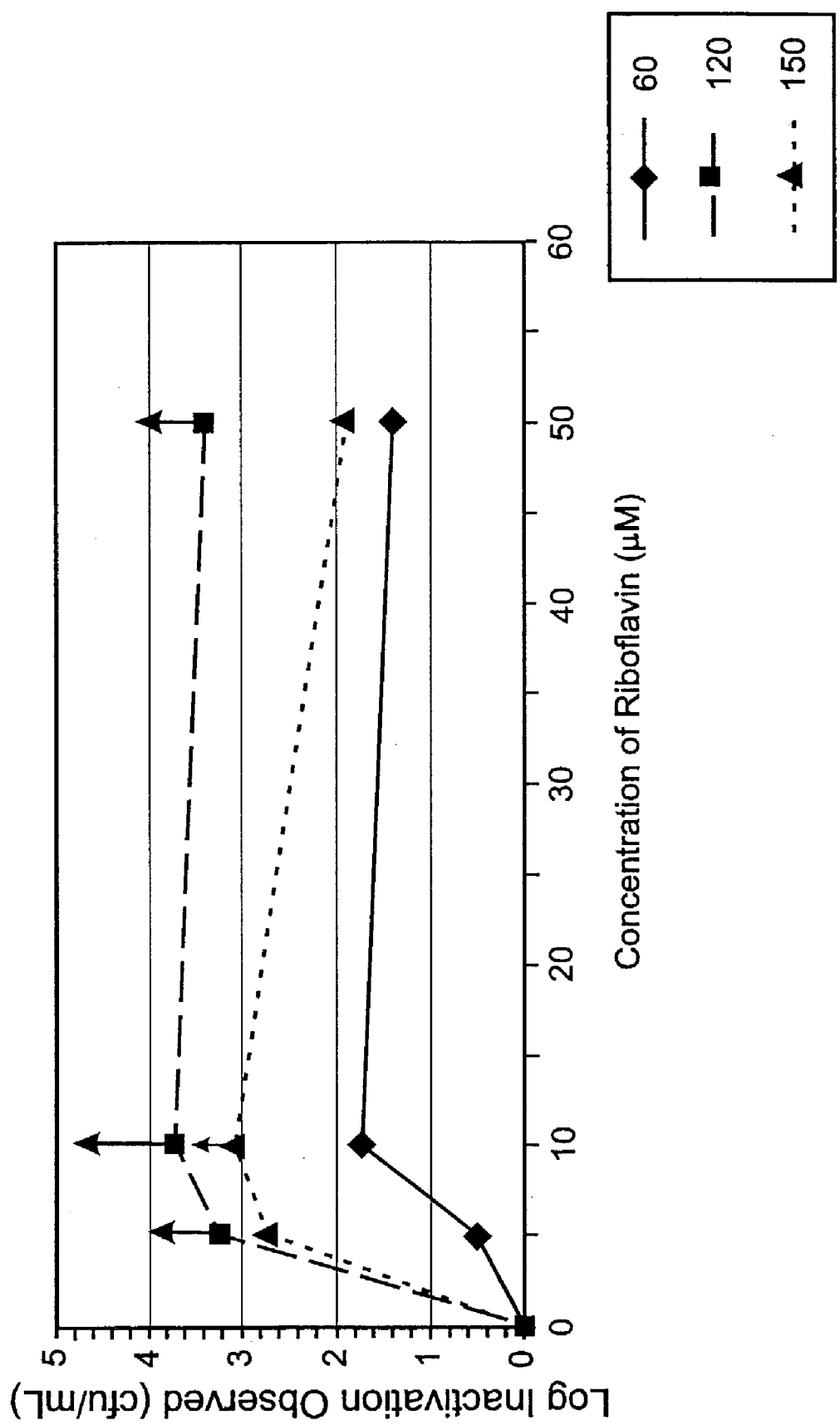
FIG. 12 is a graph showing the effect of various concentrations of mitochondrial enhancer on reduction of Herpes Virus 2 (HSV-2) as a function of photoradiation exposure time (delivered energy).

Effect of Riboflavin on Reduction of HSV-2 at Various Energy Levels and Riboflavin Concentrations HSV-2 was used to innoculate 90% PCO, wherein the balance was Isolyte S media. HSV-2 was titered before and after exposure to photoradiation from a DYMAX 2000 irradiator. FIG. 12 is a graph showing the effect of various concentrations of mitochondrial enhancer on reduction of Herpes Virus 2 as a function of photoradiation exposure time (delivered energy). Photoradiation included both visible and ultraviolet wavelengths. The four arrows on FIG. 12 indicate that the actual log inactivation data points might be higher than those shown because these samples were at the detection limit of the assay. Log reduction observed, in cfu/ml, is calculated by measuring an initial titer before treatment, measuring a titer after treatment, and subtracting the latter titer from the initial titer. Reduction was greatest with 10 micromolar riboflavin. Results are shown in Table 10.

TABLE 10

| Riboflavin Concentration (micromolar) | 60 J/cm$^2$ | 120 J/cm$^2$ | 150 J/cm$^2$ |
|---|---|---|---|
| 0 | 0 | 0 | 0 |
| 5 | 0.5 | 3.25 | 2.75 |
| 10 | 1.75 | 3.75 | 3.1 |
| 50 | 1.5 | 3.5 | 2 |

Example 12

Effect of Riboflavin on Reduction of *S. epidermidis* at Various Energy Levels and Riboflavin Concentration

Figure 13:
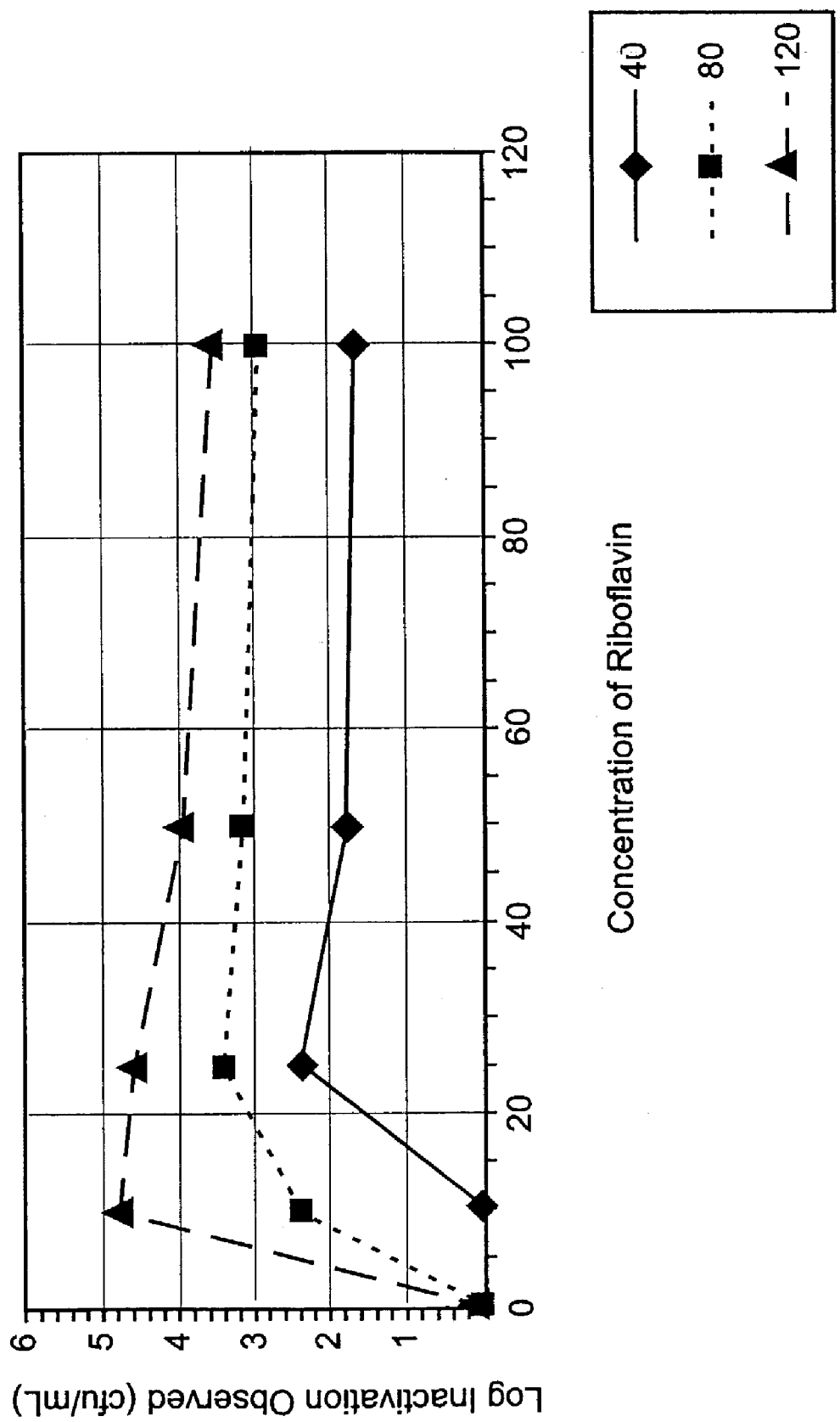
FIG. 13 is a graph showing the effect of various energy doses on reduction of *S. epidermidis* as a function of concentration of mitochondrial enhancer (micromoles).

*S. epidermidis* was used to innoculate 90% PCO, wherein the balance was Isolyte S media. *S. epidermidis* was titered before and after exposure to photoradiation from a DYMAX 2000 irradiator. Photoradiation was delivered at 40 J/cm$^2$, 80 J/cm$^2$, and 120 J/cm$^2$. Photoradiation included both visible and ultraviolet wavelengths. Riboflavin concentration was 0, 10, 25, 50, and 100 micromolar. FIG. 13 is a graph showing the effect of various energy doses on reduction of *S. epidermidis* as a function of concentration of mitochondrial enhancer. Reduction was greatest with higher energy delivery and with 10 micromolar riboflavin. Results are shown in Table 11.

TABLE 11

| Riboflavin Concentration (micromolar) | Energy Dose 40 J/cm$^2$ | Energy Dose 80 J/cm$^2$ | Energy Dose 120 J/cm$^2$ |
|---|---|---|---|
| 0 | 0 | 0 | 0 |
| 10 | 0 | 2.4 | 4.8 |
| 25 | 2.4 | 3.4 | 4.6 |
| 50 | 1.8 | 3.2 | 4 |
| 100 | 1.7 | 3 | 3.6 |

Example 13

Figure 14:
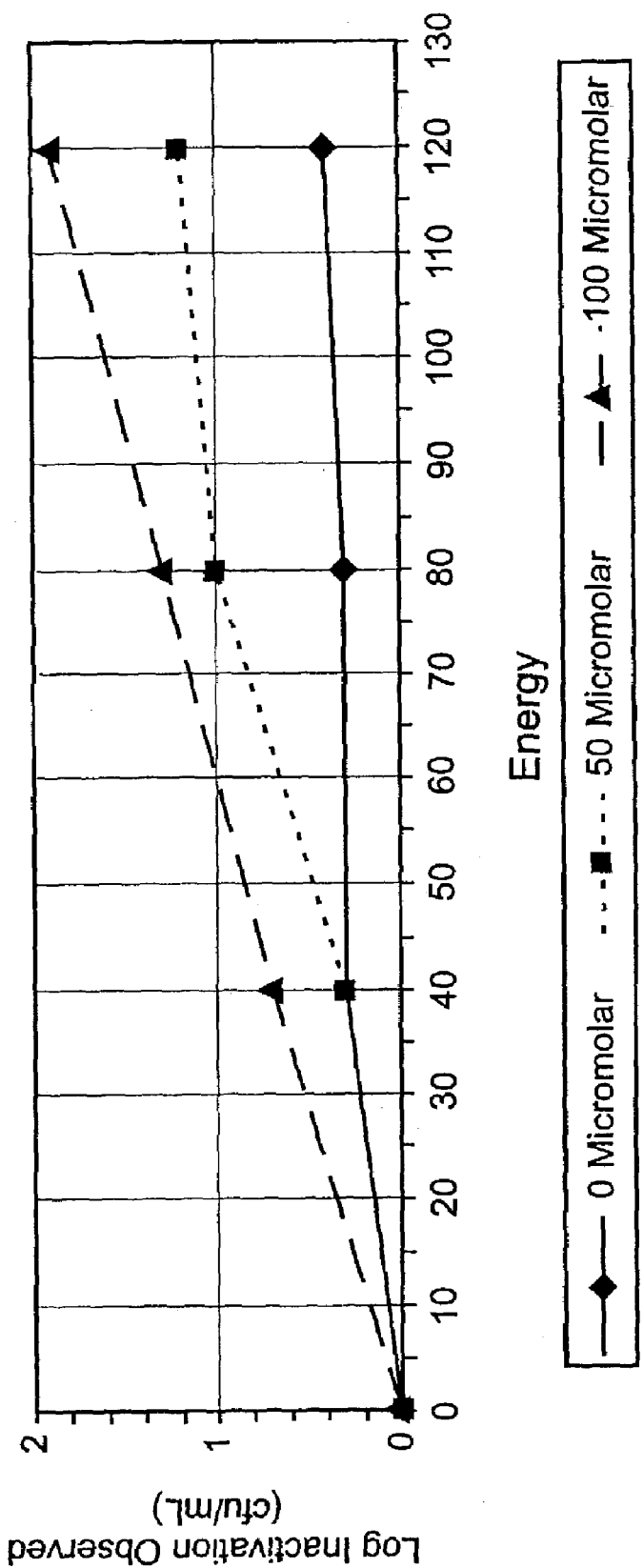
FIG. 14 is a graph showing the effect of various concentrations of mitochondrial enhancer on reduction of ΦX174 as a function of delivered photoradiation energy.

Effect of Riboflavin on Reduction of ΦX174 at Various Energy Levels and Riboflavin Concentration ΦX174 was used to innoculate 90% PCO, wherein the balance was Isolyte S media. Photoradiation was delivered at 40 J/cm$^2$, 80 J/cm$^2$, and 120 J/cm$^2$. Photoradiation included both visible and ultraviolet wavelengths. Riboflavin was at 0, 50, or 100 micromolar. FIG. 14 is a graph showing the effect of various concentrations of mitochondrial enhancer on reduction of ΦX174 as a function of delivered photoradiation energy. Reduction was greatest at higher riboflavin concentrations (100 micromolar) and higher energies (120 J/cm$^2$). Results are shown in Table 12.

TABLE 12

| Energy | 0 Micromolar | 50 Micromolar | 100 Micromolar |
|---|---|---|---|
| 0 | 0 | 0 | 0 |
| 40 | 0.3 | 0.3 | 0.7 |
| 80 | 0.3 | 1 | 1.3 |
| 120 | 0.4 | 1.2 | 1.9 |

Example 14

Treatment of Platelets with Non-Endogenous Alloxazine and Ultraviolet Light

Non-endogenous alloxazine is added to a fluid containing platelets and photosensitizer. The fluid is exposed to about 30 J/cm$^2$ ultraviolet light. After five days of storage, cell quality indicators are improved compared to an equivalent process not using non-endogenous alloxazine.

Example 15

Treatment of Platelets with Endogenously Based Derivative Alloxazine and Ultraviolet Light Endogenously based derivative alloxazine is added to a fluid containing platelets and photosensitizer. The fluid is exposed to about 30 J/cm$^2$ ultraviolet light. After five days of storage, cell quality indicators are improved compared to an equivalent process not using endogenously based derivative alloxazine.

Example 16

Treatment of Platelets with Vitamin K and Ultraviolet Light

Vitamin K is added to a fluid containing platelets and photosensitizer. The fluid is exposed to about 30 J/cm$^2$ ultraviolet light. After five days of storage, cell quality indicators are improved compared to an equivalent process not using vitamin K.

Example 17

Treatment of Platelets with Vitamin L and Ultraviolet Light

Vitamin L is added to a fluid containing platelets and photosensitizer. The fluid is exposed to about 30 J/cm$^2$ ultraviolet light. After five days of storage, cell quality indicators are improved compared to an equivalent process not using vitamin L.

Example 18

Treatment of a Peritoneal Solution with Mitochondrial Enhancer

Peritoneal solution is removed from a body, mitochondrial enhancer is added, and the peritoneal solution with mitochondrial enhancer is administered to the peritoneal space of a body. The body may be the same body from which the peritoneal solution was removed. Alternatively, mitochondrial enhancer is administered directly to the peritoneal space of a body. Cells within the peritoneal solution and/or cells that are in contact with the mitochondrial enhancer containing peritoneal space are mitochondrially enhanced.

Example 19

Treatment of a Wound Surface with Mitochondrial Enhancer

A wound is treated by administration of mitochondrial enhancer. Cells on and near the surface of the wound, including but not limited to white blood cells, red blood cells, and fibroblasts, are mitochondrially enhanced.

It will be appreciated by those of ordinary skill in the art that blood collection apheresis systems, cellular blood components, mitochondrial enhancers, alloxazines, pathogen reduction processes, photoradiation methods, storage times, cell quality indicators, and pathogens other than those specifically disclosed herein are available in the art and can be employed in the practice of this invention. All art-known functional equivalents are intended to be encompassed within the scope of this invention.

We claim:

1. A method for increasing the storage life of platelets, said method comprising adding an amount of a mitochondrial enhancer to a fluid comprising said platelets, wherein said amount is effective to increase amount and/or rate of oxygen consumption of said platelets compared to amount and/or rate of oxygen consumption of platelets in a fluid to which mitochondrial enhancer has not been added, and wherein said amount is substantially non-toxic; wherein said mitochondrial enhancer is selected from the group consisting of endogenous alloxazines and non-endogenous alloxazines, and vitamin K1, vitamin K1 oxide, vitamin K2, vitamin K5, vitamin K6, vitamin K7, vitamin K-S (II) and vitamin L, whereby the storage life of the platelets is increased such that said platelets can be administered to a patient after seven days of storage.

2. The method of claim 1 wherein the concentration of said mitochondrial enhancer in said fluid is about one to about 200 micromolar.

3. The method of claim 1 wherein said platelets have not been exposed to photoradiation greater than ambient light.

4. The method of claim 1 also comprising exposing said fluid comprising said platelets to photoradiation of sufficient energy to activate a photosensitizer in said fluid.

5. The method of claim 4 wherein said photoradiation is performed using light in the ultraviolet spectrum.

6. The method of claim 4 wherein exposing said fluid to photoradiation is performed at a time selected from the group consisting of before, after, and simultaneously with treating said platelets with said mitochondrial enhancer.

7. The method of claim 4 wherein said photoradiation is of sufficient energy to substantially reduce pathogens which may be present in said fluid.

8. The method of claim 7 wherein said pathogens are selected from the group consisting of extracellular and intracellular viruses, bacteria, bacteriophages, fungi, blood-transmitted parasites, and protozoa, and mixtures of any two or more of the foregoing.

9. The method of claim 6 wherein said photoradiation is between about 5 J/cm² and about 50 J/cm².

10. The method of claim 4 wherein said photosensitizer is said mitochondrial enhancer.

11. The method of claim 10 wherein the concentration of said photosensitizer is about 1 to about 200 micromolar.

12. The method of claim 1 wherein said platelets are not stored prior to adding said mitochondrial enhancer.

13. The method of claim 1 wherein said platelets are stored prior to adding said mitochondrial enhancer.

14. The method of claim 13 wherein said platelets are stored for more than about one hour prior to adding said mitochondrial enhancer.

15. The method of claim 13 wherein said platelets are stored for an amount of time between about 1 hour and about 7 days prior to adding said mitochondrial enhancer.

16. The method of claim 1 wherein said mitochondrial enhancer is selected from the group consisting of 7,8-dimethyl-10-ribityl isoalloxazine, 7,8-dimethylalloxazine, 7,8,10-trimethylisoalloxazine, alloxazine mononucleotide, isoalloxazine-adenosine dinucleotide, vitamin K1, vitamin K1 oxide, vitamin K2, vitamin K5, vitamin K6, vitamin K7, vitamin K-S(II), and vitamin L.

17. The method of claim 1 wherein said mitochondrial enhancer is 7,8-dimethyl-10-ribityl isoalloxazine.

18. The method of claim 1 wherein the concentration of said 7,8-dimethyl-10-ribityl isoalloxazine in said fluid is about one to about 200 micro molar.

19. The method of claim 1 wherein said mitochondrial enhancer is of the formula:

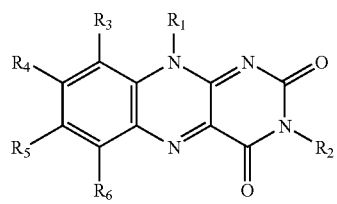

wherein R1, R2, R3, R4, R5 and R6 are, independently from one another, selected from the group consisting of hydrogen, optionally substituted hydrocarbyl, alcohol, amine, polyamine, sulfate, phosphate, halogen selected from the group consisting of chlorine, bromine and iodine, salts of the foregoing;

and —NR$^a$—(CR$^b$R$^c$)$_n$—X wherein X is a halogen selected from the group consisting of chlorine, bromine and iodine, R$^a$, R$^b$ and R$^c$ are, independently of each other, selected from the group consisting of hydrogen, optionally substituted hydrocarbyl, and halogen selected from the group consisting of chlorine, bromine and iodine, and n is an integer from 0 to 20;

provided that R1 is not —OH or a straight chain alkyl group where the second carbon of the chain is substituted with —OH or =O and R1, R4, R5 are not all methyl groups when R2, R3 and R6 are hydrogen.

20. The method of claim 19, wherein R1, R2, R3, R4, R5 and R6 are, independently from one another, selected from the group consisting of hydrogen, optionally substituted alcohol, straight chain or cyclic saccharide, amino acid, amine, polyamine, polyether, polyalcohol, sulfate, phosphate, carbonyl, glycol, halogen selected from the group consisting of chlorine, bromine and iodine, aldehyde, ketone, carboxylic acid and ascorbate.

21. The method of claim 1 wherein said oxygen consumption is increased by at least about 5%.

22. The method of claim 1 wherein rate of lactate production of said platelets is decreased by at least about 5%.

23. The method of claim 1 wherein pH of said fluid is increased by at least about 0.1 units.

24. The method of claim 1 wherein hypotonic shock response of said platelets is increased by at least about 5%.

25. The method of claim 1 wherein glucose consumption of said platelets is decreased by at least about 10%.

26. The method of claim 1 wherein platelet swirl of said platelets is increased by at least about 5%.

27. The method of claim 1 wherein platelet aggregation of said platelets is decreased by at least about 5%.

28. The method of claim 1 wherein carbon dioxide production of said platelets is increased by at least about 5%.

29. The method of claim 1 wherein cell count of said platelets is increased by at least about 5%.

30. The method of claim 1 wherein extent of shape change of said platelets is increased by at least about 5%.

31. The method of claim 1 wherein activation of said platelets is decreased by at least about 5%.

32. The method of claim 1 wherein said platelets are stored for more than about one hour after said treating.

33. The method of claim 1 also comprising a step selected from the group consisting of adding nitric oxide to said fluid, adding quencher to said fluid, adding process enhancer to said fluid, adding oxygen to said fluid, and adding glycolysis inhibitor to said fluid.

34. A method for treating a fluid comprising platelets to reduce pathogens which may be present therein and to allow said platelets to be administered to a patient after being stored for seven days, said method comprising the steps of:
(a) adding a reduction-effective, substantially non-toxic amount of a photosensitizer to said fluid;
(b) adding an amount of a mitochondrial enhancer different from said photosensitizer to said fluid; wherein said amount is effective to increase amount and/or rate of oxygen consumption of said platelets compared to the amount and/or rate of oxygen consumption of platelets in a fluid to which mitochondrial enhancer has not been added, and wherein said amount is substantially non-toxic; and
(c) exposing said fluid to photoradiation of sufficient energy to activate said photosensitizer, for a sufficient time to substantially reduce said pathogens;

wherein said mitochondrial enhancer is selected from the group consisting of endogenous alloxazines and non-endogenous alloxazines, vitamin K1, vitamin K1 oxide, vitamin K2, vitamin K5, vitamin K6, vitamin K7, vitamin K-S (II) and vitamin L and said platelets can be administered to a patient after seven days of storage.

35. The method of claim 34 wherein said energy is greater than an amount selected from the group consisting of 30 $J/cm^2$, 50 $J/cm^2$, 80 $J/cm^2$, 100 $J/cm^2$, 120 $J/cm^2$, and 180 $J/cm^2$.

36. The method of claim 34 wherein said energy is between about 5 $J/cm^2$ and about 360 $J/cm^2$.

37. The method of claim 34 wherein said energy is between about 25 $J/cm^2$ and about 180 $J/cm^2$.

38. The method of claim 34 wherein said energy is between about 75 $J/cm^2$ and about 120 $J/cm^2$.

39. The method of claim 34 wherein said energy is between about 120 $J/cm^2$ and about 180 $J/cm^2$.

* * * * *